US009783582B2

(12) United States Patent
Torres et al.

(10) Patent No.: US 9,783,582 B2
(45) Date of Patent: Oct. 10, 2017

(54) *STAPHYLOCOCCUS AUREUS* LEUKOCIDINS, THERAPEUTIC COMPOSITIONS, AND USES THEREOF

(75) Inventors: Victor J. Torres, New York, NY (US); Ashley L. Dumont, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 13/696,245

(22) PCT Filed: May 5, 2011

(86) PCT No.: PCT/US2011/035354
§ 371 (c)(1),
(2), (4) Date: Jan. 3, 2013

(87) PCT Pub. No.: WO2011/140337
PCT Pub. Date: Nov. 10, 2011

(65) Prior Publication Data
US 2013/0095115 A1 Apr. 18, 2013

Related U.S. Application Data

(60) Provisional application No. 61/331,550, filed on May 5, 2010.

(51) Int. Cl.
| C07K 14/31 | (2006.01) |
| C12Q 1/25 | (2006.01) |
| C07K 16/12 | (2006.01) |
| G01N 33/50 | (2006.01) |
| G01N 33/569 | (2006.01) |
| C12Q 1/02 | (2006.01) |
| G01N 33/68 | (2006.01) |
| A61K 39/00 | (2006.01) |

(52) U.S. Cl.
CPC .......... *C07K 14/31* (2013.01); *C07K 16/1271* (2013.01); *C12Q 1/025* (2013.01); *G01N 33/5035* (2013.01); *G01N 33/56938* (2013.01); *G01N 33/68* (2013.01); *A61K 39/00* (2013.01); *C07K 2317/76* (2013.01); *G01N 2333/31* (2013.01)

(58) Field of Classification Search
None
See application file for complete search history.

(56) References Cited

U.S. PATENT DOCUMENTS

| 7,771,728 B2 | 8/2010 | Meinke et al. |
| 8,431,687 B2 | 4/2013 | Torres et al. |
| 2011/0059085 A1 | 3/2011 | Kim |

FOREIGN PATENT DOCUMENTS

| CN | 101218252 A | 7/2007 |
| CN | 101535811 A | 9/2009 |
| WO | 02/059148 A2 | 8/2002 |
| WO | 02/094868 A2 | 11/2002 |
| WO | 2006/135912 A2 | 12/2006 |
| WO | 2009/140236 A2 | 11/2009 |

OTHER PUBLICATIONS

Bowie et al (Science, 1990, 257:1306-1310).*
Greenspan et al, (Nature Biotechnology 17:936-937, 1999).*
Harlow et al (Antibodies a Laboratory Manual, Cold Spring Harbor Laboratory Press Inc., 1988).*
Colman et al. (Research in Immunology 145: 33-36, 1994).*
Houghten et al. (New Approaches to Immunization, Vaccines 86, Cold Spring Harbor Laboratory, p. 21-25, 1986).*
Bork (Genome Research, 2000,10:398-400).*
Gladstone, "An Improved Leucocidin Toxoid," Br. J. Exp. Pathol. 54(3):255-259 (1973).
Davis et al., "A Selective Neutorphil Dysfunction Syndrome: Impaired Killing of Staphylococci," Ann. Intern. Med. 69(6):1237-1244 (1968) (abstract only).
Brown et al., "The Panton-Valentine Leukocidin Vaccine Protects Mice Against Lung and Skin Infections Caused by *Staphylococcus aureus* USA300," Clin. Microbiol. Infect. 15:156-164 (2009).
Corbin et al., "Metal Chelation and Inhibition of Bacterial Growth in Tissue Abscesses," Science 319:962-965 (2008).
Diep et al., "Polymorphonuclear Leukocytes Mediate *Staphylococcus aureus* Panton-Valentine Leukocidin-Induced Lung Inflammation and Injury," Proc. Nat'l. Acad. Sci. U.S.A. 107:5587-5592 (2010).
Foster, "Immune Evasion by Staphylococci," Nat. Rev. Microbiol. 3:948-958 (2005).
Gramberg et al., "Evidence for an Activation Domain at the Amino Terminus of Simian Immunodeficiency Virus Vpx," J. Virol. 84:1387-1396 (2010).
Fridkin et al., "Methicillin-Resistant *Staphylococcus aureus* Disease in Three Communities," N. Engl. J. Med. 352:1436-1444 (2005).
Graves et al., "Community-Associated Methicillin-Resistant *Staphylococcus aureus* Immune Evasion and Virulence," J. Mol. Med. 88:109-114 (2010).
Gresham et al., "Survival of *Staphylococcus aureus* Inside Neutrophils Contributes to Infection," J. Immunol. 164: 3713-3722 (2000).
Hongo et al., "Phenol-Soluble Modulin Alpha 3 Enhances the Human Neutrophil Lysis Mediated by Panton-Valentine Leukocidin," J. Infect. Dis. 200:715-723 (2009).
Labandeira-Rey et al., "*Staphylococcus aureus* Panton Valentine Leukocidin Causes Necrotizing Pneumonia," Science 315:1130-1133 (2007).
Lekstrom-Himes et al., "Immunodeficiency Diseases Caused by Defects in Phagocytes," N. Engl. J. Med. 343:1703-1714 (2000).
(Continued)

*Primary Examiner* — Robert A Zeman
(74) *Attorney, Agent, or Firm* — LeClairRyan, a Professional Corporation

(57) ABSTRACT

Disclosed herein are isolated and purified *Staphylococcus aureus* bi-component leukocidin, referred to herein as LukAB, and its components LukA and LukB, antibodies specific to LukA, antibodies specific to LukB, therapeutic compositions containing LukA and/or LukB, or anti-LukA and/or anti-LukB antibodies, uses of the compositions to treat acute inflammatory conditions or *S. aureus* infection, methods for identifying inhibitors of LukAB-mediated cytotoxicity of human phagocytes, and methods for using LukAB as a marker to predict severity of *S. aureus* infection.

3 Claims, 21 Drawing Sheets

(56) References Cited

OTHER PUBLICATIONS

Loffler et al., "*Staphylococcus aureus* Panton-Valentine Leukocidin is a Very Potent Cytotoxic Factor for Human Neutrophils," PLos Pathog. 6:e1000715 (2010).
Menestrina et al., "Mode of Action of Beta-Barrel Pore-Forming Toxins of the Staphylococcal Alpha-Hemolysin Family," Toxicon 39:1661-1672 (2001).
Menestrina et al., "Ion Channels and Bacterial Infection: The Case of Beta-Barrel Pore-Forming Protein Toxins of *Staphylococcus aureus*," FEBS Lett. 552:54-60 (2003).
Nizet, "Understanding How Leading Bacterial Pathogens Subvert Innate Immunity to Reveal Novel Therapeutic Targets," J. Allergy Clin. Immunol. 120:13-22 (2007).
Ogston, "Micrococcus Poisoning," J. Anat. Physiol. 17:24-58 (1882).
Patel et al., "Virulence of Protein A-Deficient and Alpha-Toxin Deficient Mutants of *Staphylococcus aureus* Isolated by Allele Replacement," Infect. Immun. 55:3103-3110 (1987).
Tseng et al., "*Staphylococcus aureus* Panton-Valentine Leukocidin Contributes to Inflammation and Muscle Tissue Injury," PLoS One 4:e6387 (2009).
Varshney et al., "Augmented Production of Panton-Valentine Leukocidin Toxin in Methicillin-Resistant and Methicillin-Susceptible *Staphylococcus aureus* is Associated With Worse Outcome in a Murine Skin Infection Model," J. Infect. Dis. 201:92-96 (2010).
Ventura et al., "Identification of a Novel *Staphylococcus aureus* Two-Component Leukotoxin Using Cell Surface Proteomics," PLoS One 5:e11634 (2010).
Verdrengh & Tarkowski, "Role of Neutrophils in Experimental Septicemia and Septic Arthritis Induced by *Staphylococcus aureus*," Infect. Immun. 65:2517-2521 (1997).
Voyich et al., "Insights Into Mechanisms Used by *Staphylococcus aureus* to Avoid Destruction by Human Neutrophils," J. Immunol. 175:3907-3919 (2005).
Wang et al., "Identification of Novel Cytolytic Peptides as Key Virulence Determinants for Community-Associated MRSA," Nat. Med. 13:1510-1514 (2007).
Wardenburg & Schneewind, "Vaccine Protection Against *Staphylococcus aureus* Pneumonia," J. Exp. Med. 205:287-294 (2008).
Dumont et al., "Characterization of a New Cytotoxin That Contributes to *Staphylococcus aureus* Pathogenesis," Mol. Microbiol. 79(3):814-825 (2011).
Yamashita et al., "Crystal Structure of the Octameric Pore of Staphylococcal Gamma-Hemolysis Reveals the Beta-Barrel Pore Formation Mechanism by Two Components," Proc. Nat'l. Acad. Sci. U.S.A. 108(42):17314-17319 (2011).
Wardenburg et al., "Poring Over Pores: Alpha-Hemolysin and Panton-Valentine Leukocidin in *Staphylococcus aureus* Pneumonia," Nat. Med. 13(12):1405-1407 (2007).
Eiff et al., "Prevalence of Genes Encoding for Members of the Staphylococcal Leukotoxin Family Among Clinical Isolates of *Staphylococcus aureus*," Diag. Microbiol. Infect. Dis. 49:157-162 (2004).
Gauduchon et al., "Neutralization of *Staphylococcus aureus* Panton Valentine Leukocidin by Intravenous Immunoglobulin in Vitro," J. Infect. Dis. 189:346-353 (2004).
International Search Report for PCT/US2011/035354 (Jan. 19, 2012).
Jaysihghe et al., "The Leukocidin Pore: Evidence for an Octamer With Four LukF Subunits and Four LukS Subunits Alternating Around a Central Axis," Protein Sci. 14:2550-2561 (2005).
Meyer et al., "Analysis of the Specificity of Panton-Valentine Leucocidin and Gamma-Hemolysin F Component Binding," Infect. Immun. 77(1):266-273 (2009).
Miles et al., "The Staphylococcal Leukocidin Biocomponent Toxin Forms Large Ionic Channels," Biochem. 40:8514-8522 (2001).
Rainard et al., "Leucotoxic Activities of *Staphylococcus aureus* Strains Isolated From Cows, Ewes, and Goats With Mastitis: Importance of LukM/LukF-PV Leukotoxin," Clin. Diagn. Lab. Immunol. 10(2):272-277 (2003).
Rottini et al., "Identification and Partial Characterization of a Cytolytic Toxin Produced by Gardnerella vaginalis," Infect. Immun. 58(11):3751-3758 (1990).
Third Party Observation for EP 11778343.1 (Sep. 6, 2013).
Baba et al., "Genome Sequence of *Staphylococcus aureus* Strain Newman and Comparative Analysis of Staphylococcal Genomes: Polymorphism and Evolution of Two Major Pathogenicity Islands," J. Bacteriol. 190(1):300-310 (2008).
NCBI Ref. Seq. Protein Accession No. YP 001332961 for Leukocidin/Hemolysin Toxin Subunit F (2007).
NCBI Ref. Seq. Protein Accession No. YP 001332962 for Leukocidin/Hemolysin Toxin Subunit S (2007).
Australian Examination Report for corresponding Australian Patent Application No. 2011247989 (Sep. 5, 2014).
Translation of and Second Office Action for corresponding Chinese Patent Application No. 201180033386.0 (Aug. 28, 2014).
European Search Report for corresponding European Patent Application No. 11778343.1 (Oct. 7, 2014).
Supplementary European Search Report for corresponding European Patent Application No. 11778343.1 (Jan. 9, 2014).
O'Brien et al., "Immunization with *Staphylococcus aureus* Lysate Incorporated into Microspheres," J. Dairy Sci. 84:1791-1799 (2001).
Office Action and Search Report for corresponding Chinese Patent Application No. 201180033386.0 (Dec. 2, 2013).
European Search Report for corresponding European Patent Application No. 11778343.1 (Dec. 17, 2013).
Database Accession No. AAU37509 (Feb. 14, 2002).
Database Accession No. A6QIL8 (Mar. 2, 2010).
Database Accession No. D1GPS9 (Mar. 23, 2010).
Pedelacq et al., "The Structure of a *Staphylococcus aureus* Leucidin Component (LukF-PV) Reveals the Fold of the Water-Soluble Species of a Family of Transmembrane Pore-Forming Toxins," Structure 7(3):277-287 (1999).
Katsumi et al., "Vitronectin and Its Fragments Purified as Serum Inhibitors of *Staphylococcus aureus* Gamma-Hemolysin and Leukocidin, and Their Specific Binding to the Hlg2 and the LukS Components of the Toxins," FEBS Letters 460:451-456 (1999).
Database Accession No. ABM70852 (Nov. 20, 2003).
Examination Report for corresponding Australian Patent Application No. 2011247989 (Oct. 22, 2013).
Rainard et al. "Leucotoxic Activities of *Staphylococcus aureus* Strains Isolated from Cows, Ewes, and Goats with Mastitis: Importance of LukM/LukF'-PV Leukotoxin," Clinical and Diagnostic Laboratory Immunology 10(2):272-277 (2003).
Gauduchon et al. "Neutralization of *Staphylococcus aureus* Panton Valentine Leukocidin by Intraveneous Immunoglobulin In Vitro," The Journal of Infectious Diseases 189:346-353 (2004).
Eiff et al. "Prevalence of Genes Encoding for Members of the Stapylococcal Leukutoxin Family Among Clinical Isolates of *Staphylococcus aureus*," Diagnostic Microbiology and Infectious Disease 49:157-162 (2004).
PCT International Search Report and Written Opinion for PCT/US2011/035354, mailed Jan. 19, 2012.
Attia et al., "Membrane Damage Elicits an Immunomodulatory Program in *Staphylococcus aureus*," PLoS Pathog. 6(3):e1000802 (2010).
International Preliminary Report on Patentability for corresponding PCT/US2011/035354 (Nov. 6, 2012).
Torres et al., "*Staphylococcus aureus* Fur Regulates the Expression of Virulence Factors That Contribute to the Pathogenesis of Pneumonia," Infect. Immun. 78(4):1618-1628 (2010).
Schafer et al., "A Point Mutation in the Sensor Histidine Kinase SaeS of *Staphylococcus aureus* Strain Newman Alters the Response to Biocide Exposure," J. Bacteriol. 191(23):7306-7314 (2009).
Examination Report for corresponding European Patent Application No. 11778343.1 (May 28, 2015).
Notice of Reasons for Rejection and English Translation for corresponding Japanese Patent Application No. 2013-509265 (Apr. 16, 2015).
Office Action and Translation for corresponding Israel Patent Application No. 95093/2.2 (Jun. 11, 2015).

(56) References Cited

OTHER PUBLICATIONS

Holden et al., "Genome Sequence of a Recently Emerged, Highly Transmissible, Multi-Antibiotic- and Antiseptic-Resistant Variant of Methicillin-Resistant *Staphylococcus aureus*, Sequence Type 239 (TW)," J. Bacteriol. 192(3):888-892 (2010).
Russia Official Action and English Translation for Patent Application No. 2012152086/10 (Oct. 29, 2015).
Russia Official Action and English Translation for Patent Application No. 2012152086/10 (Jun. 9, 2016).
Office Action and English Translation for corresponding Chinese Patent Application No. 201180033386.0 (Mar. 16, 2016).
Second Notice of Reasons for Rejection and English Translation for corresponding Japanese Patent Application No. 2013-509265 (Jan. 28, 2016).
Holtfreter et al., "Towards the Immune Proteome of *Staphylococcus aureus*—The anti-*S. aureus* antibody response," Int. J. Med. Microbiol. 300:176-192 (2010).
Russia Official Action for Patent Application No. 2012152086/10(083042) (Jul. 23, 2015).
Australia Examination Report for Patent Application No. 2015200901 (Nov. 23, 2015).
Extended Search Report for EP 16187485.4 (Nov. 18, 2016).
English Translation and Office Action for CN 201180033386.0 (Oct. 21, 2016).
Official Action for Canadian Patent Application No. 2,798,355 (Dec. 2, 2016).

\* cited by examiner

FIG. 1-1

| | | | | | | | | |
|---|---|---|---|---|---|---|---|---|
| | 10 | 20 | 30 | 40 | 50 | 60 | 70 | 80 |

Majority    MKNKKRVLIASSLSCAILLLSAATTQANSAHKDSQDQNKKEHVDKSQQKEKRNVTNKDKNSTXPDDIGKNGKITKRTETV LukA (Newman).pro                    MKNKKRVLIASSLSCAILLLSAATTQANSCAHKDSQDQNKKEHVDKSQQKDKRNVTNKDKNSTAPDDIGKNGKITKRTETV    80
HMPREF0772_0044(TCH60).pro           MKNKKRVFIASSLSCALLLLSAANTEANSANKDSQDQTKKEHVDKAQQKEKRNVNDKDKNTPGPDDIGKNGKVTKRTVSE    80
HMPREF0774_2356(TCH130).pro          MKNKKRVLIASSLSCAILLLSAATTQANSAHKDSQDQNKKEHVDKSQQKEKRNVTNKDKNSTVPDDIGKNGKITKRTETV    80
HMPREF0776_0173(USA300_TCH959).pro   MKNKKRVLIASSLSCAILLLSAATTQANSAHKDSQDQNKKEHVDKSQQKDKRNVTNKDKNSTAPDDIGKNGKITKRTETV    80
MW1942(MW2).pro                      MKNKKRVLIASSLSCAILLLSAATTQANSAHKDSQDQNKKEHVDKSQQKEKRNVTNKDKNSTVPDDIGKNGKITKRTETV    80
SA1813 (N315).pro                    MKNKKRVLIASSLSCAILLLSAATTQANSAHKDSQDQNKKEHVDKSQQKDKRNVTNKDKNSTVPDDIGKNGKITKRTETV    80
SAB1876c(RF122).pro                  MKNKKRVLIASSLSCAILLLSAATTQANSAHKDSQDQNKKEHVDKSQQKDKRNVTNKDKNSTVPDDIGKNGKITKRTETV    80
SACOL2006 (Col).pro                  MKNKKRVLIASSLSCAILLLSAATTQANSAHKDSQDQNKKEHVDKSQQKDKRNVTNKDKNSTAPDDIGKNGKITKRTETV    80
SALG_02329(A9635).pro                MKNKKRVFIASSLSCALLLLSAANTEANSANKDSQDQTKKEHVDKAQQKEKRNVNDKDKNTPGPDDIGKNGKVTKRTVSE    80
SAPIG2061(ST398).pro                 MKNKKRVFIASSLSCAILLLSAANTEANSANKDSQDQTKKEHVDKAQQKEKRNVNDKDKNTPGPDDIGKNGKVTKRTETV    80
SAR2108 (MRSA252).pro                MKNKKRVFIASSLSCAILLLSAANTEANSANKDSQDQTKKEHVDKAQQKEKRNVNDKDKNTPGPDDIGKNGKVTKRTETV    80
SATG_01930(D139).pro                 MKNKKRVFIASSLSCVLLLLSAANTEANSANKDSQDQTKKEHVDKAQQKEKRNVNDKDKNTPGPDDIGKNGKVTKRTVSE    80
SAV2005 (Mu50).pro                   MKNKKRVFIASSLSCAILLLSAATTQANSAHKDSQDQNKKEHVDKSQQKDKRNVTNKDKNSTVPDDIGKNGKITKRTETV    80

FIG. 1-2

```
Majority         YDEKTNILQNLQFDFIDDPTYDKNVLLVKKQGSIHSNLKFESHKEEKNSNWLKYPSEYHVDFQVKRNRKTEILDQLPKNK
                          +---------+---------+---------+---------+---------+---------+---------+---------+
                         90        100       110       120       130       140       150       160

LukA(Newman).pro                                                                                                       160
HMPREF0772_0044(TCH60).pro          YDEKTNILQNLQFDFIDDPTYDKNVLLVKKQGSIHSNLKFESHKEEKNSNWLKYPSEYHVDFQVKRNRKTEILDQLPKNK   160
HMPREF0774_2356(TCH130).pro         YDEKTNILQNLQFDFIDDPTYDKNVLLVKKQGSIHSNLKFESHRNETNASWLKYPSEYHVDFQVQRNPKTEILDQLPKNK   160
HMPREF0776_0173(USA300_TCH959).pro  YDEKTNILQNLQFDFIDDPTYDKNVLLVKKQGSIHSNLKFESHKEEKNSNWLKYPSEYHVDFQVKRNRKTEILDQLPKNK   160
MW1942(MW2).pro                     YDEKTNILQNLQFDFIDDPTYDKNVLLVKKQGSIHSNLKFESHKEEKNSNWLKYPSEYHVDFQVKRNRKTEILDQLPKNK   160
SA1813(N315).pro                    YDEKTNILQNLQFDFIDDPTYDKNVLLVKKQGSIHSNLKFESHKEEKNSNWLKYPSEYHVDFQVKRNRKTEILDQLPKNK   160
SAB1876c(RF122).pro                 YDEKTNILQNLQFDFIDDPTYDKNVLLVKKQGSIHSNLKFESHKEEKNSNWLKYPSEYHVDFQVKRNRKTEILDQLPKNK   160
SACOL2006(Col).pro                  YDEKTNILQNLQFDFIDDPTYDKNVLLVKKQGSIHSNLKFESHKEEKNSNWLKYPSEYHVDFQVKRNRKTEILDQLPKNK   160
SALG_02329(A9635).pro               YDEKTNILQNLQFDFIDDPTYDKNVLLVKKQGSIHSNLKFESHRNETNASWLKYPSEYHVDFQVQRNPKTEILDQLPKNK   160
SAPIG2061(ST398).pro                YDEKTNILQNLQFDFIDDPTYDKNVLLVKKQGSIHSNLKFESHKEENNSSWLKYPSEYHVDFQVQRNPKTEILDQLPKNK   160
SAR2108(MRSA252).pro                YDEKTNILQNLQFDFIDDPTYDKNVLLVKKQGSIHSNLKFESHRNETNASWLKYPSEYHVDFQVQRNPKTEILDQLPKNK   160
SATG_01930(D139).pro                YDEKTNILQNLQFDFIDDPTYDKNILLVKKQGSIHSNLKFESHKEENNSSWLKYPSEYHVDFQVKRNRKTEILDQLPKNK   160
SAV2005(Mu50).pro                   YDEKTNILQNLQFDFIDDPTYDKNVLLVKKQGSIHSNLKFESHKEEKNSNWLKYPSEYHVDFQVKRNRKTEILDQLPKNK   160
```

FIG. 1-3

| | | 170 | 180 | 190 | 200 | 210 | 220 | 230 | 240 |
|---|---|---|---|---|---|---|---|---|---|
| Majority | | ISTAKVDSTFSYSSGGKFDSTKGIGRTSSNSYSKTISYNQQNYDTIASGKNNWHVHWSVIANDLKYGGEVKNRNDELLF | | | | | | | 240 |

```
LukA (Newman).pro              ISTAKVDSTFSYSSGGKFDSTKGIGRTSSNSYSKTISYNQQNYDTIASGKNNWHVHWSVIANDLKYGGEVKNRNDELLF  240
HMPREF0772_0044(TCH60).pro     ISTAKVDSTFSYSLGGKFDSTKGIGRTSSNSYSKSISYNQQNYDTIASGKNNNRHVHWSVVANDLKYGNEIKNRNDEFLF 240
HMPREF0774_2356(TCH130).pro    ISTAKVDSTFSYSSGGKFDSTKGIGRTSSNSYSKTISYNQQNYDTIASGKNNWHVHWSVIANDLKYGGEVKNRNDELLF  240
HMPREF0776_0173(USA300_TCH959).pro ISTAKVDSTFSYSSGGKFDSTKGIGRTSSNSYSKTISYNQQNYDTIASGKNNWHVHWSVIANDLKYGGEVKNRNDELLF 240
MW1942(MW2).pro                ISTAKVDSTFSYSSGGKFDSTKGIGRTSSNSYSKTISYNQQNYDTIASGKNNWHVHWSVIANDLKYGGEVKNRNDELLF  240
SA1813 (N315).pro              ISTAKVDSTFSYSSGGKFDSTKGIGRTSSNSYSKTISYNQQNYDTIASGKNNWHVHWSVIANDLKYGGEVKNRNDELLF  240
SAB1876c(RF122).pro            ISTAKVDSTFSYSSGGKFDSTKGIGRTSSNSYSKTISYNQQKYDTIAIGKNNWHVHWSVIANDLKYGGEVKNRNDELLF  240
SACOL2006 (Col).pro            ISTAKVDSTFSYSSGGKFDSTKGIGRTSSNSYSKTISYNQQNYDTIASGKNNWHVHWSVIANDLKYGGEVKNRNDELLF  240
SALG_02329(A9635).pro          ISTAKVDSTFSYSLGGKFDSTKGIGRTSSNSYSKSISYNQQNYDTIASGKNNNRHVHWSVVANDLKYGNEIKNRNDEFLF 240
SAPIG2061(ST398).pro           ISTAKVDSTFSYSLGGKFDSVKGVGRTSSNSYSKTISYNQQNYDTIASGKNNWHVHWSVVANDLKYGGEVKNRNDELLF  240
SAR2108(MRSA252).pro           ISTAKVDSTFSYNSGGKFDSTKGIGRTSSNSYSKTISYNQQNYDTIASGKNNWHVHWSVIANDLKYGGEVKNRNDELLF  240
SATG_01930(D139).pro           ISTAKVDSTFSYSLGGKFDSTKGIGRTSSNSYSKSISYNQQNYDTIASGKNNNRHVHWSVVANDLKYGNEIKNRNDEFLF 240
SAV2005(Mu50).pro              ISTAKVDSTFSYSSGGKFDSVKGVGRTSSNSYSKTISYNQQNYDTIASGKNNWHVHWSVVANDLKYGGEVKNRNDELLF  240
```

FIG. 1-4

```
Majority              YRNTRIATVENPELSFASKYRYPALVRSGFNPEFLTYLSNEKSNEKTQFEVTYTRNQDILKNRPGIHYAPPILEKNKDGQ 250       260       270       280       290       300       310       320
                     ----+----|----+----|----+----|----+----|----+----|----+----|----+----|----+----|

LukA(Newman).pro              YRNTRIATVENPELSFASKYRYPALVRSGFNPEFLTYLSNEKSNEKTQFEVTYTRNQDILKNRPGIHYAPPILEKNKDGQ   320
HMPREF0772_0044(TCH60).pro    YRNTRLSTVENPELSFASKYRYPALVRSGFNPEFLTYLSNEKSNEKTRFEVTYTRNQDILKNRPGIHYGQPILEKNKDGQ   320
HMPREF0774_2356(TCH130).pro   YRNTRIATVENPELSFASKYRYPALVRSGFNPEFLTYISNEKSNEKTQFEVTYTRNQDILKNRPGIHYAPPILEKNKEGQ   320
HMPREF0776_0173(USA300_TCH959).pro YRNTRIATVENPELSFASKYRYPALVRSGFNPEFLTYLSNEKSNEKTQFEVTYTRNQDILKNRPGIHYAPPILEKNKDGQ   320
MW1942(MW2).pro               YRNTRIATVENPELSFASKYRYPALVRSGFNPEFLTYLSNEKSNEKTQFEVTYTRNQDILKNRPGIHYAPPILEKNKEGQ   320
SA1813(N315).pro              YRNTRIATVENPELSFASKYRYPALVRSGFNPEFLTYLSNEKSNEKTQFEVTYTRNQDILKNRPGIHYAPPILEKNKDGQ   320
SAB1876c(RF122).pro           YRNTRIATVENPELSFASKYRYPALVRSGFNPEFLTYLSNEKSNEKTQFEVTYTRNQDILKNRPGIHYAPPILEKNKDGQ   320
SACOL2006(Col).pro            YRNTRIATVENPELSFASKYRYPALVRSGFNPEFLTYLSNEKSNEKTQFEVTYTRNQDILKNRPGIHYAPPILEKNKDGQ   320
SALG_02329(A9635).pro         YRNTRIATVENPELSFASKYRYPALVRSGFNPEFLTYLSNEKTNDKTRFEVTYTRNQDILKNRPGIHYGQPILEQNKDGQ   320
SAPIG2061(ST398).pro          YRNTRIATVENPELSFASKYRYPALVRSGFNPEFLTYLSNEKSNEKTQFEVTYTRNQDVLKNRPGIHYAPPILEKNKDGQ   320
SAR2108(MRSA252).pro          YRNTRLSTVENPELSFASKYRYPALVRSGFNPEFLTYISNEKSNEKTQFEVTYTRNQDILKNRPGIHYGQPILEQNKDGQ   320
SATG_01930(D139).pro          YRTTRLSTVENPELSFASKYRYPALVRSGFNPEFLTYLSNEKSNEKTRFEVTYTRNQDILKNRPGIHYAPPILEKNKDGQ   320
SAV2005(Mu50).pro             YRNTRIATVENPELSFASKYRYPALVRSGFNPEFLTYLSNEKSNEKTQFEVTYTRNQDILKNRPGIHYAPSILEKNKDGQ   320
```

FIG. 1-5

```
Majority          RLIVTYEVDWKNKTVKVVDKYSDDNKPYKEG 330       340       350

LukA(Newman).pro                  RLIVTYEVDWKNKTVKVVDKYSDDNKPYKEG  351
HMPREF0772_0044(TCH60).pro        RFIVVYEVDWKNKTVKVVEKYSDQNKPYKEG  351
HMPREF0774_2356(TCH130).pro       RLIVTYEVDWKNKTVKVVDKYSD-NKSFREG  350
HMPREF0776_0173(USA300_TCH959).pro RLIVTYEVDWKNKTVKVVDKYTD-NKSFREG 350
MW1942(MW2).pro                   RLIVTYEVDWKNKTVKVVDKYSD-NKSFREG  350
SA1813(N315).pro                  RLIVTYEVDWKNKTVKVVDKYSDDNKPYKEG  351
SAB1876c(RF122).pro               RLIVTYEVDWKNKTVKVVDKYSDDNKPYKEG  351
SACOL2006(Col).pro                RLIVTYEVDWKNKTVKVVDKYSDDNKPYKEG  351
SALG_02329(A9635).pro             RFIVVYEVDWKNKTVKVVEKYSDQNKPYKEG  351
SAPIG2061(ST398).pro              RLIVTYEVDWKNKTVKVIDKYSDENKPYKEG  351
SAR2108(MRSA252).pro              RFIVVYEVDWKNKTVKVVEKYSDQNKPYKEG  351
SATG_01930(D139).pro              RLIVTYEVDWKNKTVKVIDKYSDDNKPYKEG  351
SAV2005(Mu50).pro                 RLIVTYEVDWKNKTVKVVDKYSDDNKPYKEG  351
```

FIG. 2-1

```
                       10        20        30        40        50        60        70        80
                        ----+----|----+----|----+----|----+----|----+----|----+----|----+----|----+----|
Majority         MIKQLCKNITICSLALSTALTVPATSYAKINSEIKQVSEKNLDGDTKMYTRTATTSDSQRNITQSLQFNFLTEPNYDKE A9635.pro        MIKQVCKNITICSLALSTALTVPASSYAEIKSKITTVSEKNLDGDTKMYTRTATTSDTEKKISQSLQFNFLTEPNYDKE    80
COL.pro          -------------------------------------MYTRTATTSDSQRNITQSLQFNFLTEPNYDKE             32
D139.pro         MIKQVCKNITICSLALSTALTVPASSYAKINSEIKQVSEKNLDGETKMYTRTATTSDSQRNITQSLQFNFLTEPNYDKE    80
E1410.pro        MIKQVCKNITICSLALSTALTVPASSYAEIKSKITTVSEKNLDGDTKMYTRTATTSDTEKKISQSLQFNFLTEKNYDKE    80
JKD6008.pro      MIKQLCKNITICTLALSTTFTVLPATSFAKINSEIKQVSEKNLDGDTKMYTRTATTSDSQRNITQSLQFNFLTEPNYDKE   80
MRSA252.pro      MIKQVCKNITICSLALSTALTVPASSYAEIKSKITTVSEKNLDGDTKMYTRTATTSDTEKKISQSLQFNFLTEPNYDKE    80
Mu50.pro         MIKQLYKNITICSLAISTALTVPATSYAKINSEIKAVSEKNLDGDTKMYTRTATTSDSQRNITQSLQFNFLTEPNYDKE    80
MW2.pro          MIKQLYKNITICSLTISTALTVPASSYAKINSEIKAVSEKNLDGDTKMYTRTATTSDSQRNITQSLQFNFLTEPNYDKE    80
RF122.pro        MIKQLYKNITICSLTISTALTVPASSYAKINSEIKQVSEKNLDGDTKMYTRTATTSDSQRNITQSLQFNFLTEPNYDKE    80
TCH130.pro       MIKQLCKNITICTLALSTTFTVLPATSFAKINSEIKQVSEKNLDGDTKMYTRTATTSDSQRNITQSLQFNFLTEPNYDKE   80
USA300_FPR3757.pro MIKQLCKNITICTLALSTTFTVLPATSFAKINSEIKQVSEKNLDGDTKMYTRTATTSDSQRNITQSLQFNFLTEPNYDKE 80
Newman (LukB).pro MIKQLCKNITICTLALSTTFTVLPATSFAKINSEIKQVSEKNLDGDTKMYTRTATTSDSQRNITQSLQFNFLTEPNYDKE  80
```

FIG. 2-2

```
Majority         TVFIKAKGTIGSGLRILDPNGYWNSTLRWPGSYSVSIQNVDDNNN-TNVTDFAPKNQDESREVKYTVGYKTGGDFSINRG
                          90        100       110       120       130       140       150       160

A9635.pro        TVFIKAKGTIGSGLKILNPNGYWNSTLRWPGSYSVSIQNVDDNNNSTNVTDFAPKNQDESREVKYTVGYKTGGDFSINRG    160
COL.pro          TVFIKAKGTIGSGLRILDPNGYWNSTLRWPGSYSVSIQNVDDNNN-TNVTDFAPKNQDESREVKYTVGYKTGGDFSINRG    111
D139.pro         TVFIKAKGTIGSGLRILEPNGYWNSTLRWPGSYSVSIQNVDDNNN-TNVTDFAPKNQDESREVKYTVGYKTGGDFSINQG    159
E1410.pro        TVFIKAKGTIGSGLKILNPNGYWNSTLTWPGSYSVSIQNVDDNNNSTNVTDFAPKNQDESREVKYTVGYKTGGDFSINRG    160
JKD6008.pro      TVFIKAKGTIGSGLRILDPNGYWNSTLRWPGSYSVSIQNVDDNNN-TNVTDFAPKNQDESREVKYTVGYKTGGDFSINRG    159
MRSA252.pro      TVFIKAKGTIGSGLKILNPNGYWNSTLRWPGSYSVSIQNVDDNNNSTNVTDFAPKNQDESREVKYTVGYKTGGDFSINRG    160
Mu50.pro         TVFIKAKGTIGSGLRILDPNGYWNSTLRWPGSYSVSIQNVDDNNN-TNVTDFAPKNQDESREVKYTVGYKTGGDFSINRG    159
MW2.pro          TVFIKAKGTIGSGLRILDPNGYWNSTLRWPGSYSVSIQNVDDNNN-TNVTDFAPKNQDESREVKYTVGYKTGGDFSINRG    159
RF122.pro        TVFIKAKGTIGSGLRILDPNGYWNSTLRWPGSYSVSIQNVDDNNN-TNVTDFAPKNQDESREVKYTVGYKTGGDFSINRG    159
TCH130.pro       TVFIKAKGTIGSGLRILDPNGYWNSTLRWPGSYSVSIQNVDDNNN-TNVTDFAPKNQDESREVKYTVGYKTGGDFSINRG    159
USA300_FPR3757.pro TVFIKAKGTIGSGLRILDPNGYWNSTLRWPGSYSVSIQNVDDNNN-TNVTDFAPKNQDESREVKYTVGYKTGGDFSINRG  159
Newman (LukB).pro TVFIKAKGTIGSGLRILDPNGYWNSTLRWPGSYSVSIQNVDDNNN-TNVTDFAPKNQDESREVKYTVGYKTGGDFSINRG   159
```

FIG. 2-3

```
Majority        GLTGNITKESNYSETISYQQPSYRTLLDQSTSHKGVGWKVEAHLINNMGHDHTRQLTNDSDNRTKSEIFSLTRNGNLWAK 170       180       190       200       210       220       230       240
                ----+---------+---------+---------+---------+---------+---------+---------+

A9635.pro            GLTGNITKEKNYSETISYQQPSYRTLLDQPTTNKGVAWKVEAHLINNMGHDHTRQLTNDSDDRVKSEIFSLTRNGNLWAK  240
COL.pro              GLTGNITKESNYSETISYQQPSYRTLLDQSTSHKGVGWKVEAHLINNMGHDHTRQLTNDSDNRTKSEIFSLTRNGNLWAK  191
D139.pro             GLTGNITKESNYSETISYQQPSYRTLLDQPTTNKGVAWKVEAHLINNMGHDHTRQLTNDSDDRVKSEIFSLTRNGNLWAK  239
E1410.pro            GLTGNITKEKNYSETISYQQPSYRTLIDQPTTNKGVAWKVEAHLINNMGHDHTRQLTNDSDDRVKSEIFSLTRNGNLWAK  240
JKD6008.pro          GLTGNITKESNYSETISYQQPSYRTLLDQSTSHKGVGWKVEAHSINNMGHDHTRQLTNDSDNRTKSEIFSLTRNGNLWAK  239
MRSA252.pro          GLTGNITKEKNYSETISYQQPSYRTLIDQPTTNKGVAWKVEAHLINNMGHDHTRQLTNDSDDRVKSEIFSLTRNGNLWAK  240
Mu50.pro             GLTGNITKESNYSETISYQQPSYRTLLDQSTSHKGVGWKVEAHLINNMGHDHTRQLTNDSDNRTKSEIFSLTRNGNLWAK  239
MW2.pro              GLTGNITKESNYSETISYQQPSYRTLLDQSTSHKGVGWKVEAHLINNMGHDHTRQLTNDSDNRTKSEIFSLTRNGNLWAK  239
RF122.pro            GLPGNITKESNYSETISYQQPSYRTLLDQSTSHKGVGWKVEAHLINNMGHDHTRQLTNDSDNRTKSEIFSLTRNGNLWAK  239
TCH130.pro           GLTGNITKESNYSETISYQQPSYRTLLDQSTSHKGVGWKVEAHLINNMGHDHTRQLTNDSDNRTKSEIFSLTRNGNLWAK  239
USA300_FPR3757.pro   GLTGNITKESNYSETISYQQPSYRTLLDQSTSHKGVGWKVEAHLINNMGHDHTRQLTNDSDNRTKSEIFSLTRNGNLWAK  239
Newman(LukB).pro     GLTGNITKESNYSETISYQQPSYRTLLDQSTSHKGVGWKVEAHLINNMGHDHTRQLTNDSDNRTKSEIFSLTRNGNLWAK  239
```

FIG. 2-4

```
Majority        DNFTPKNKMPVTVSEGFNPEFLAVMSHDKKDGKSQFVHYKRSMDEFKIDWNRHGFWGYWSGENHVDKKEEKLSALYEV 250       260       270       280       290       300       310       320
                -----+---------+---------+---------+---------+---------+---------+---------+

A9635.pro       DNFTPKNKMPVTVSEGFNPEFLAVMSHDKKDGKSRFIVHYKRSMDDFKLDWNKHGFWGYWSGENHVDQKEEKLSALYEV  320
COL.pro         DNFTPKDKMPVTVSEGFNPEFLAVMSHDKKDGKSQFVHYKRSMDEFKIDWNRHGFWGYWSGENHVDKKEEKLSALYEV  271
D139.pro        DNFTPKNKMPVTVSEGFNPEFLAVMSHDKKDEGKSKFVHYKRSMDEFKIDWNRHGFWGYWSGENHVDKKEEKLSALYEV  319
E1410.pro       DNFTPKNKMPVTVSEGFNPEFLAVMSHDKKDGKSQFVHYKRSMDEFKIDWNRHGFWGYWSGENHVDKKEEKLSALYEV  320
JKD6008.pro     DNFTPKNKMPVTVSEGFNPEFLAVMSHDKNDKGKSRFIVHYKRSMDDFKLDWNKHGFWGYWSGENHVDQKEEKLSALYEV  319
MRSA252.pro     DNFTPKNKMPVTVSEGFNPEFLAVMSHDKNDKGKSRFIVHYKRSMDDFKLDWNKHGFWGYWSGENHVDEKEEKLSALYEV  320
Mu50.pro        DNFTPKNKMPVTVSEGFNPEFLAVMSHDKKDGKGKSQFVHYKRSMDEFKIDWNRHGFWGYWSGENHVDQKEEKLSALYEV  319
MW2.pro         DNFTPKNKMPVTVSEGFNPEFLAVMSHDKKDGKSQFVHYKRSMDEFKIDWNRHGFWGYWSGENHVDKKEEKLSALYEV  319
RF122.pro       DNFTPKNKMPVTVSEGFNPEFLAVMSHDKKDEGKSKFVHYKRSMDEFKIDWNRHGFWGYWSGENHVDKKEEKLSALYEV  319
TCH130.pro      DNFTPKNKMPVTVSEGFNPEFLAVMSHDKKDEGKSKFVHYKRSMDEFKIDWNRHGFWGYWSGENHVDKKEEKLSALYEV  319
USA300_FPR3757.pro DNFTPKNKMPVTVSEGFNPEFLAVMSHDKKDGKSQFVHYKRSMDEFKIDWNRHGFWGYWSGENHVDKKEEKLSALYEV  319
Newman (LukB).pro DNFTPKDKMPVTVSEGFNPEFLAVMSHDKKDGKSQFVHYKRSMDEFKIDWNRHGFWGYWSGENHVDKKEEKLSALYEV  319
```

FIG. 2-5

| | | |
|---|---|---|
| Majority | DWKTHNVKFVKVLNDNEKK | |
| | 330 | |
| A9635.pro | DWKTHDVKLIKTFNDKEKK | 339 |
| COL.pro | DWKTHNVKFVKVLNDNEKK | 290 |
| D139.pro | DWKTHNVKFIKVLNDKEKK | 338 |
| E1410.pro | DWKTHDVKLIKTINDKEQK | 339 |
| JKD6008.pro | DWKTHNVKFVKVLNDNEKK | 338 |
| MRSA252.pro | DWKTHDVKLIKTINDKEQK | 339 |
| Mu50.pro | DWKTHDVKFVKVLNDNEKK | 338 |
| MW2.pro | DWKTHNVKFVKVLNDNEKK | 338 |
| RF122.pro | DWKTHDVKFVKVLNDNEKK | 338 |
| TCH130.pro | DWKTHDVKFVKVLNDNEKK | 338 |
| USA300_FPR3757.pro | DWKTHNVKFVKVLNDNEKK | 338 |
| Newman (LukB).pro | DWKTHNVKFVKVLNDNEKK | 338 |

FIG. 11A-1

```
Majority    ................................XNNIEDIGXG--AEIIKRTEDVXSKKWGVTQNI QFDFVKDKYNKDA
                    10        20        30        40        50        60        70        80

HlgA        ...............................ENKIEDIGQG--AEIIKRTQDITSKRLAITQNI QFDFVKDKYNKDA      45
HlgC        ...............................ANDTEDIGKGSDIEIIKRTEDKTSNKWGVTQNI QFDFVKDKYNKDA      47
LukE        ...............................NTNIENIGDG--AEVIKRTEDVSSKKWGVTQNVQFDFVKDKYNKDA      45
LukA        NSAHKDSQDQNKKEHVDKSQQKDKRNVTNKDKNSTAPDDIGKN--GKITKRTETVYDEKTNI LQNLQFDFIDDPTYDKNV      78
LukS-PVL    ...............................DNNIENIGDG--AEVVKRTEDTSSDKWGVTQNI QFDFVKDKYNKDA      45

Majority    LIVKMQGFIXSRTTYXXYKK--XXHIKXMXWPFQYNIGLKTK-DPNVXLINYLPKNKIXSXXVSQTLGYNIGGNFQSAPS
                    90       100       110       120       130       140       150       160

HlgA        LVVKMQGFISSRTTYSDLKK--YPYITKRMIWPFQYNISLKTK-DSNVDLINYLPKNKIDSADVSQKLGYNIGGNFQSAPS     122
HlgC        LILKMQGFISSRTTYNYKK--TNHVKAMRWPFQYNIGLKTN-DKYVSLINYLPKNKIESTNVSQTLGYNIGGNFQSAPS     124
LukE        LIVKMQGFINSRTSFSDVKGSGYELTKRMIWPFQYNIGLTTK-DPNVSLINYLPKNKIETTDVGQTLGYNIGGNFQSAPS     124
LukA        LLVKKQGSIHSNLKFESHKE--EKNSNWLKYPSEYHVDFQVKRNRKTEILDQLPKNKISTAKVDSTFSYSSGGKFDSTKG     156
LukS-PVL    LILKMQGFINSKTTYNYKN--TDHIKAMRWPFQYNIGLKTN-DPNVDLINYLPKNKIDSVNVSQTLGYNIGGNFNSGPS     122

Majority    IGGNGSFNYSKTISYNQQNYVSEVE-KQNSKSVKWGVKANSFVTPXGXKSAHDXYLFVXXKPXXP--NPRDYFVPDNXLP
                   170       180       190       200       210       220       230       240

HlgA        IGGSGSFNYSKTISYNQKNYVEVE-SQNSKGVKWGVKANSFVTPNGQVSAYDQYLFAQ-DPTGP--AARDYFVPDNQLP      198
HlgC        LGGNGSFNYSKSISYTQQNYVSEVE-QQNSKSVLWGVKANSFATESGQKSAFDSDLFVGYKPHSK--DPRDYFVPDSELP      201
LukE        IGGNGSFNYSKTISYTQKSYVSEVD-KQNSKSVKWGVKANEFVTPDGKKSAHDRYLFVQ-SPNGPTGSAREYFAPDNQLP      202
LukA        IGRTSSNSYSKTIASGKNNNNVHWSVIANDLKYGGEVKNRNDELLFYRNTRIATVENPELSFASKYRYP      236
LukS-PVL    TGGNGSFNYSKTISYNQQNYISEVE-RQNSKSVQWGIKANSFITSLGKMSGHDPNLFVGYKPYSQ--NPRDYFVPDNELP      199
```

FIG. 11A-2

| | 250 | 260 | 270 | 280 | 290 | 300 | 310 | 320 | |
|---|---|---|---|---|---|---|---|---|---|
| Majority | PLVQSGFNPSFI | TTLSHEKGSXDT | SEFEI TYGRNMDXTXATXR-XHY----LXGXRKHNAFVNRNYTVKYEVNWKTHEIK | | | | | | |
| HlgA | PLTQSGFNPSFI TTLSHERGKGDKSEFEI TYGRNMDATYAYVT-RHR----LAVDRKHDAFKNRNVTVKYEVNWKTHEVK | | | | | | | | 273 |
| HlgC | PLVQSGFNPSFI ATVSHEKGSSDTSEFEI TYGRNMDVTHAI KRSTHYGNSYLDGHRVHNAFVNRNYTVKYEVNWKTHEIK | | | | | | | | 281 |
| LukE | PLVQSGFNPSFI TTLSHEKGSSDTSEFEI SYGRNLDI TYATLFPRTG----IYAERKHNAFVNRNFVVRYEVNWKTHEIK | | | | | | | | 278 |
| LukA | ALVRSGFNPEFLTYLSNEK-SNEKTQFEVTYTRNQDI LKNRPG-IHY----APPI LEKNKDGQR-LI VTYEVDWKNKTVK | | | | | | | | 309 |
| LukS-PVL | PLVHSGFNPSFI ATVSHEKGSGDTSEFEI TYGRNMDVTHATRRTTHYGNSYLEGSRI HNAFVNRNYTVKYEVNWKTHEIK | | | | | | | | 279 |

| | 330 | |
|---|---|---|
| Majority | VKGHN----- | |
| HlgA | TKSTTPK | 280 |
| HlgC | VKGQN | 286 |
| LukE | VKGHN | 283 |
| LukA | VVDKYSDDNKPYKEG | 324 |
| LukS-PVL | VKGHN | 284 |

STAPHYLOCOCCUS AUREUS LEUKOCIDINS, THERAPEUTIC COMPOSITIONS, AND USES THEREOF

CROSS-REFERENCE TO RELATED APPLICATIONS

This application is a national stage application under 35 U.S.C. §371 of PCT Application No. PCT/US2011/035354, filed May 5, 2011, which claims the benefit of the filing date of U.S. Provisional Patent Application No. 61/331,550 filed May 5, 2010, the disclosure of which is hereby incorporated herein by reference.

SEQUENCE LISTING

The instant application contains a Sequence Listing which has been submitted via EFS-Web and is hereby incorporated by reference in its entirety. Said ASCII copy, created on May 2, 2011 is named Sequence Listing_Staphylococcus Aureus Leukocidins_ST25.txt, and is 102 kilobytes in size.

BACKGROUND OF THE INVENTION

*Staphylococcus aureus* bacteria or "staph" are normally found on the skin or in the nose of people and animals. Staph bacteria are generally harmless, unless they enter the body through a cut or other wound. Typically, staph infections are minor skin problems in healthy people. Historically, staph infections were treated by broad-spectrum antibiotics, such as methicillin. Now, though, certain strains of staph have emerged that are resistant to methicillin and other β-lactam antibiotics such as penicillin and cephalosporins. They are referred to as methicillin-resistant *Staphylococcus aureus* (also known as multi-drug resistant *Staphylococcus aureus*, or "MRSA").

Staph infections, including MRSA, generally start as small red bumps that resemble pimples, boils or spider bites. These bumps or blemishes can quickly turn into deep, painful abscesses that require surgical draining. Sometimes the bacteria remain confined to the skin. On occasion, they can burrow deep into the body, causing potentially life-threatening infections in a broad range of human tissue, including skin, soft tissue, bones, joints, surgical wounds, the bloodstream, heart valves, lungs, or other organs. Thus, *S. aureus* infections can result in potentially fatal diseases such as necrotizing fasciitis, pneumonia, endocarditis, sepsis, toxic shock syndrome, and various forms of pneumonia. MRSA infection is especially troublesome in hospital or nursing home settings where patients are prone to open wounds, invasive devices, and weakened immune systems and thus are at greater risk for infection than the general public. Workers who do not follow proper sanitary procedures may transfer MRSA bacteria from one patient to another.

*S. aureus* produces a diverse array of virulence factors and toxins that enable this bacterium to neutralize and withstand attack by different kinds of immune cells, specifically subpopulations of white blood cells that make up the body's primary defense system. The production of these virulence factors and toxins allow *S. aureus* to maintain an infectious state. See, Nizet, J. Allergy Clin. Immunol. 120:13-22 (2007). Among these virulence factors, *S. aureus* produces several bi-component leukotoxins, which damage membranes of host defense cells and erythrocytes by the synergistic action of two non-associated proteins or subunits. See, Supersac, et al., Infect. Immun. 61:580-7 (1993). Among these bi-component leukotoxins, gamma-hemolysin (HlgAB and HlgCB) and the Pantone-Valentine Leukocidin (PVL) are the best characterized.

The toxicity of the leukocidins towards mammalian cells involves the action of two components. The first subunit is named class S-subunit (i.e., "slow-eluted"), and the second subunit is named class F-subunit (i.e., "fast-eluted"). The S- and F-subunits act synergistically to form pores on white blood cells including monocytes, macrophages, dendritic cells and neutrophils (collectively known as phagocytes). See, Menestrina, et al., Toxicol. 39:1661-1672 (2001). The mechanism by which the bi-component toxins form pores in target cell membranes is not entirely understood. The proposed mechanism of action of these toxins involves binding of the S-subunit to the target cell membrane, most likely through a receptor, followed by binding of the F-subunit to the S-subunit, thereby forming an oligomer which in turn forms a pre-pore that inserts into the target cell membrane (Jayasinghe, et al., Protein. Sci. 14:2550-2561 (2005)). The pores formed by the bi-component leukotoxins are typically cation-selective. Pore formation causes cell death via lysis, which in the cases of the target white blood cells, has been reported to result from an osmotic imbalance due to the influx of cations (Miles, et al., Biochemistry 40:8514-8522 (2001)).

In addition to PVL (also known as leukocidin S/F-PV or LukSF-PV) and gamma-hemolysin (HlgAB and HlgCB), the repertoire of bi-component leukotoxins produced by *S. aureus* is known to include leukocidin E/D (LukED) and leukocidin M/F'(LukMF'). Thus, the S-class subunits of these bi-component leukocidins include HlgA, HlgC, LukE, LukS-PV, and LukM, and the F-class subunits include HlgB, LukD, LukF-PV, and LukF'-PV (Menestrina, et al., supra.). The *S. aureus* S- and F-subunits are not leukocidin-specific. That is, they are interchangeable such that other bi-component combinations could make a functional pore in a white blood cell, greatly increasing the repertoire of leukotoxins (Meyer, et al., Infect. Immun. 77:266-273 (2009)).

Designing effective therapy to treat MRSA infection has been especially challenging. In addition to the aforementioned resistance to methicillin and related antibiotics, MRSA has also been found to have significant levels of resistance to macrolides (e.g., erythromycin), beta-lactamase inhibitor combinations (e.g., Unasyn, Augmentin) and fluoroquinolones (e.g., ciprofloxacin), as well as to clindamycin, trimethoprim/sulfamethoxisol (Bactrim), and rifampin. In the case of serious *S. aureus* infection, clinicians have resorted to intravenous vancomycin. However, there have been reports of *S. aureus* resistance to vancomycin. Thus, there is a need to develop new antibiotic drugs that effectively combat *S. aureus* infection.

BRIEF SUMMARY OF THE INVENTION

Applicants have discovered and characterized another bi-component member of the native *Staphylococcus aureus* defense system. The newly characterized native S-subunit polypeptide component is referred to herein as "LukA", which embraces the native polypeptides and analogs thereof having a sequence similarity of at least 70% with the sequences of the native polypeptides. Thus, an aspect of the present invention is directed to an isolated and/or purified LukA. Another aspect of the present invention is directed to an isolated and/or purified polynucleotide encoding LukA, a transformed host (e.g., cell) containing the polynucleotide, and methods for preparation of recombinant LukA via expression of the polynucleotide in the transformed host.

The newly characterized F-subunit polypeptide component is referred to herein as "LukB", which embraces the native polypeptides and analogs thereof having a sequence similarity of at least 70% with the sequences of the native polypeptides. Thus, another aspect of the present invention is directed to an isolated and/or purified LukB. Another aspect of the present invention is directed to an isolated and/or purified polynucleotide encoding LukB, a transformed host (e.g., cell) containing the polynucleotide, and methods for preparation of recombinant LukB via expression of the polynucleotide in the transformed host.

Yet another aspect of the present application is directed to therapeutic compositions useful in inhibiting onset of or treating a *Staphyloccocus aureus* infection containing therapeutically effective amounts of LukA and/or LukB formulated in a pharmaceutically acceptable carrier. Thus, in one embodiment, the therapeutic composition contains a therapeutically effective amount of LukA. In another embodiment, the therapeutic composition contains a therapeutically effective amount of LukB. In yet another embodiment, the therapeutic composition contains therapeutically effective amounts of both LukA and LukB. In yet other embodiments, the composition contains an analog of LukA that lacks the 10 C-terminal residues and which is non-toxic (referred to herein as LukAΔ10C or rLukAΔ10C). These compositions have multiple therapeutic uses. In some embodiments, the compositions are referred to as anti-inflammatory compositions and may be used to treat acute inflammatory conditions or disorders, particularly localized acute inflammatory conditions.

These uses exploit Applicants' additional discoveries that under physiological conditions (i.e., LukAB produced directly by *S. aureus*), the LukAB complex has exquisite specificity for phagocytes but not other nucleated cells such as epithelial cells and endothelial cells. That is, the complex forms pores in membranes of these kinds of cells, thus causing cell death, which is referred to herein as "LukAB-mediated cytotoxicity." On the other hand, LukAB has relatively little or negligible specificity with respect to other nucleated mammalian cells. Thus, the anti-inflammatory compositions of the present invention exploit the specificity of LukAB for human phagocytes, for purposes of treating acute inflammatory conditions, which are characterized by massive infiltration of phagocytes to the site of inflammation.

In other embodiments, the therapeutic compositions may be referred to as a (active) vaccine composition. The compositions may be used to induce production of neutralizing anti-LukA and anti-LukB antibodies in a subject at risk of *S. aureus* infection or a subject diagnosed with *S. aureus* infection such as MRSA.

Other aspects of the present invention are directed to antibodies that specifically bind LukA, antibodies that specifically bind LukB, therapeutic compositions containing the LukA and/or LukB antibodies, and uses thereof to treat *S. aureus* infectious conditions. These therapeutic compositions may be referred to as passive vaccine compositions. Thus, in one embodiment, the therapeutic composition contains a therapeutically effective amount of anti-LukA antibodies. In another embodiment, the therapeutic composition contains a therapeutically effective amount of anti-LukB antibodies. In yet another embodiment, the therapeutic composition contains therapeutically effective amounts of both anti-LukA and anti-LukB antibodies.

The passive and active vaccine compositions of the present invention exploit Applicants' further discovery that infectious, virulent *S. aureus* strains such as MRSA, express LukA and LukB. The conservation of LukA and LukB across a large spectrum of *S. aureus* strains enables the vaccines of the present invention to provide full-spectrum therapeutic effectiveness. LukA, LukB, anti-LukA antibodies and anti-LukB antibodies are also referred to herein as active agents.

A further aspect of the present invention is directed to methods of using LukAB, LukA, and/or LukB to identify potential inhibitors of LukAB-mediated cytotoxicity. These methods may utilize the LukAB complex, per se, in combination with a phagocyte, or a phagocyte membrane-binding portion thereof. Thus-identified inhibitors may be candidates for therapy for the purposes of treating *S. aureus* infection.

An even further aspect of the present invention is directed to a method of predicting or assessing severity of an *S. aureus* infection which entails detecting presence or amount of LukA and/or LukB, or detecting corresponding genes of LukA and/or LukB, in a biological sample obtained from an infected subject. This aspect of the present invention is based on Applicants' even further discovery that among the many cytotoxins produced by *S. aureus*, LukAB exhibits potent toxicity towards human phagocytes. Thus, detection of presence or relatively high amounts of LukA and/or LukB, or their corresponding genes (e.g., as exhibited by *S. aureus* strain Newman, 4645, and MRSA strains USA300 and USA500) relative to a control (e.g., *S. aureus* strains USA100 and USA400) which produces little or undetectable amounts of LukA and/or LukB, is indicative of a severe *S. aureus* infection.

These and other aspects of the present invention are more fully described below.

BRIEF DESCRIPTION OF THE DRAWINGS

FIG. 1 is an alignment containing the amino acid sequence of a majority LukA sequence (designated as SEQ ID NO:1), and the LukA polypeptides, LukA (Newman).pro (SEQ ID NO: 2), HMPREF0772_0044(THC60).pro (SEQ ID NO: 3), HMPREF0774_2356(TCH130) .pro (SEQ ID NO: 4), HMPREF0776_0173(USA300_TCH959).pro (SEQ ID NO: 5), MW1942(MW2).pro (SEQ ID NO: 6), SA1813 (N315).pro (SEQ ID NO: 7), SAB1876c (RF122).pro SEQ ID NO: 8), SACOL2006 (Col).pro (SEQ ID NO: 9), SALG_02329 (A9635).pro (SEQ ID NO: 10), SAPIG2061 (ST398).pro (SEQ ID NO: 11), SAR2108 (MRSA252).pro (SEQ ID NO: 12), SATG_01930 (D139).pro (SEQ ID NO: 13), and SAV2005 (Mu50).pro (SEQ ID NO: 14), from thirteen (13) different strains of *S. aureus* to which it corresponds.

FIG. 2 is an alignment containing the amino acid sequence of a majority LukB sequence (designated as SEQ ID NO:15), and the LukB polypeptides, A9635.pro (SEQ ID NO: 16), COL.pro (SEQ ID NO: 17), D139.pro (SEQ ID NO: 18), E1410.pro (SEQ ID NO: 19), JKD6008.pro (SEQ ID NO: 20), MRSA252.pro (SEQ ID NO: 21), Mu50.pro (SEQ ID NO: 22), MW2.pro (SEQ ID NO: 23), RF122.pro (SEQ ID NO: 24), TCH130.pro (SEQ ID NO: 25), USA300_FPR3757.pro (SEQ ID NO: 26), and Newman (LukB).pro (SEQ ID NO: 27), from twelve (12) different strains of *S. aureus* to which it corresponds.

DETAILED DESCRIPTION

Figure 3:
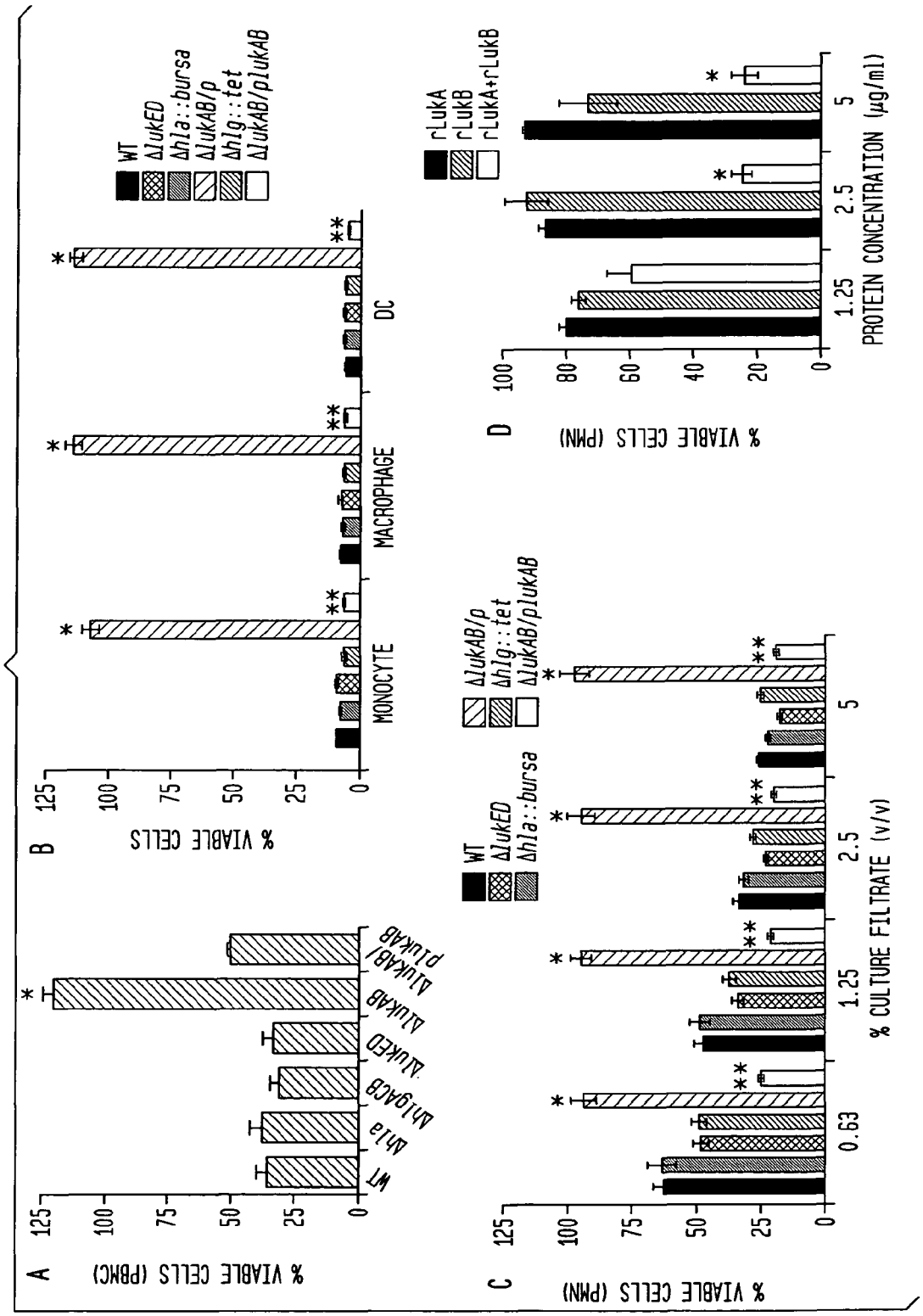
FIG. 3. LukAB is a potent staphylococcal cytotoxin that targets and kills primary human phagocytes. (a) Intoxication of primary human peripheral blood mononuclear cells (PBMCs) with culture filtrate (2.5% v/v) from *S. aureus* strain Newman (WT) and the indicated isogenic mutant strains. Cell viability was monitored using a commercially available cell viability assay, where cells treated with medium were set at 100%. Results represent the average of triplicate samples+standard deviation (S.D.). (b) Intoxication of primary human monocytes, macrophages, and dendritic cells (DC) with culture filtrate (2.5% v/v) from S. aureus strain Newman (WT) and the indicated isogenic mutant strains. Cell viability was monitored as described above. Results represent the mean from two donors, where cells from each donor were intoxicated with three independent exoprotein preparations, +S.E.M. (c) Intoxication of primary human PMNs with various dilutions of culture filtrates from the S. aureus strain Newman (WT) and the indicated isogenic mutant strains. Cell viability was monitored as described above. Results represent the mean from PMNs isolated from four donors ±S.E.M. (d) Intoxication of primary human PMNs with purified rLukA, rLukB, or a combination of rLukA and rLukB at the indicated concentrations. * indicates statistical significance from both rLukA and rLukB, $P<0.05$. For panels (a-c) * indicates statistical significance from WT, ** indicates statistical significance from ΔLukAB/p, $P<0.05$(Student's t test $p<0.05$).

The following disclosure is directed, in successive order, to LukA polypeptides, LukB polypeptides, LukA and LukB polynucleotides, anti-LukA and anti-LukB antibodies, therapeutic compositions containing LukA and/or LukB, or anti-LukA and/or anti-LukB antibodies, methods of using the therapeutic compositions, methods of identifying inhibitors of LukAB-mediated cytotoxicity, and methods of predicting or assessing severity of an *S. aureus* infection.

LukA Polypeptides

Polypeptides native to *Staphylococcus aureus* have now been isolated and identified by Applicants as exhibiting the activity profile of known S-subunit leukocidins (e.g., LukS-PVL, LukE and HlgC). These polypeptides which are designated collectively herein as LukA, specifically target and bind human phagocytes (but not human epithelial or human endothelial cells, or murine cells), and once bound to the phagocyte membrane, LukA oligomerizes with an *S. aureus* F-subunit leukocidin (e.g., LukF-PVL, LukD and HlgB, and LukB as disclosed herein), and upon oligomerization forms a transmembrane pore (collectively referred to as LukA activity). The alignment illustrated in FIG. 1 contains amino acid sequences of a majority LukA sequence (designated herein as SEQ ID NO:1), and the LukA polypeptides from 13 different strains of *S. aureus* to which it corresponds (designated herein as SEQ ID NOS:2-14).

The N-terminal 27 amino acid residues in each of SEQ ID NOS:1-14 represent the native secretion/signal sequence. Thus, the mature, secreted form of LukA, which is represented by amino acid residues 28-351 in each of SEQ ID NOS: 1-14, may be referred to herein as "LukA (28-351)" or "mature LukA". Correspondingly, the immature form of LukA may be referred to herein as "LukA (1-351)".

A LukA consensus sequence, based on SEQ ID NOS: 2-14 (which are not exhaustive with respect to native *S. aureus* LukA) would thus include variability at a minimum of 64 positions of LukA (wherein consecutive positions of variability are denoted $X^1$-$X^{64}$, designated as follows: 8($X^1$=L or F), 16 ($X^2$=A or V), 17 ($X^3$=I or L), 24 ($X^4$=T or N), 26 ($X^5$=Q or E), 31 ($X^6$=H or N), 38 ($X^7$=N or T), 46 ($X^8$=S or A), 50 ($X^9$=E or D), 55 ($X^{10}$=T or N), 56 ($X^{11}$=N or D), 61 ($X^{12}$=S or T), 62 ($X^{13}$=T or P), 63 ($X^{14}$=A, G or V), 73 ($X^{15}$=I or V), 78 ($X^{16}$=E or V), 77 ($X^{17}$=T or S), 80 ($X^{18}$=V or E), 83 ($X^{19}$=E or K), 84 ($X^{20}$=E or K), 105 ($X^{21}$=V or I), 124 ($X^{22}$=K or R), 125 ($X^{23}$=E or N), 127 ($X^{24}$=K, T or N), 129 ($X^{25}$=S or A), 130 ($X^{26}$=N or S), 135 ($X^{27}$=K or Q) 146 ($X^{28}$=R or S), 148 ($X^{29}$=R or P), 173 ($X^{30}$=S or N), 174 ($X^{31}$=S or L), 181 ($X^{32}$=T or V), 184 ($X^{33}$=I or V), 195 ($X^{34}$=T or S), 202 ($X^{35}$=N or K), 208 ($X^{36}$=S or I), 214 ($X^{37}$=W or R), 221 ($X^{38}$=I or V) 229 ($X^{39}$=G or N), 231 ($X^{40}$=V or I), 237 ($X^{41}$=E or D), 239 ($X^{42}$=L or F), 243 ($X^{43}$=N or T), 246 ($X^{44}$=I or L), 247 ($X^{45}$=A or 8), 278 ($X^{46}$=L or I), 283 ($X^{47}$=S or T), 285 ($X^{48}$=E or D), 288 ($X^{49}$=Q or R) 299 ($X^{50}$=I or V), 303 ($X^{51}$=R or K), 309 ($X^{52}$=A or G), 310 ($X^{53}$=P or Q), 315 ($X^{54}$=K or Q), 318 ($X^{55}$=D or E), 322 ($X^{56}$=L or F), 325 ($X^{57}$=T or V), 338 ($X^{58}$=V or I), 339 ($X^{59}$=D or E), 342 ($X^{60}$=S or T), 344 ($X^{61}$=D, E or Q), 347 ($X^{62}$=P or S), 348 ($X^{63}$=Y or F), and 349 ($X^{64}$=K or R).

LukB Polypeptides

Polypeptides native to *Staphylococcus aureus* have now been identified by Applicants as exhibiting the activity profile of known F-subunit leukocidins (e.g., LukF-PVL, LukD and HlgB). These polypeptides which are designated collectively herein as LukB, specifically oligomerize with an *S. aureus* S-subunit leukocidin (e.g., LukS-PVL, LukE and HlgC, and LukA as disclosed herein) which is bound to a human phagocyte; and upon oligomerization form a transmembrane pore in the phagocyte (collectively referred to as LukB activity). The alignment illustrated in FIG. 2 contains amino acid sequences of a majority LukB sequence (designated herein as SEQ ID NO:15) and the LukB polypeptides from the 12 different strains of *S. aureus* to which it corresponds (designated herein as SEQ ID NOS:16-27).

The N-terminal 29 amino acid residues in each of SEQ ID NOS:15-27 represent the secretion/signal sequence. Thus, the mature, secreted form of LukB, which is represented by amino acid residues 30-339 in each of SEQ ID NOS: 16-27, may be referred to herein as "LukB (30-339)" or "mature LukB". Correspondingly, the immature form of LukB may be referred to herein as "LukA (1-339)".

A LukB consensus sequence, based on SEQ ID NOS:15-28 (which are not exhaustive with respect to native *S. aureus* LukB) would thus include variability at a minimum of 49 positions of LukB (wherein consecutive positions of variability are denoted $X^1$-$X^{49}$), designated as follows: 5 ($X^1$=L or V), 6 ($X^2$=C or Y), 13 ($X^3$=S or T), 15 ($X^4$=A or T), 16 ($X^5$=L or I), 19 ($X^6$=A or T), 20 ($X^7$=L or F), 23 ($X^8$=F or L), 26 ($X^9$=S or T), 28 ($X^{10}$=Y or F), 34 ($X^{11}$=E or K), 36 ($X^{12}$=K or T), 37 ($X^{13}$=Q, T or A), 46 ($X^{14}$=D or E), 59 ($X^{15}$=S or T), 60 ($X^{16}$=Q or E), 62 ($X^{17}$=N or K), 64 ($X^{18}$=T or S), 75 ($X^{19}$=P or K), 95 ($X^{20}$=K or R), 98 ($X^{21}$=N, d or E), 126 ($X^{22}$=S or a deletion), 159 ($X^{23}$=R or Q), 163 ($X^{24}$=T or P), 170 ($X^{25}$=S or K), 187 ($X^{26}$=L or I), 190 ($X^{27}$=S or P), 192 ($X^{28}$=S or T), 193 ($X^{29}$=S or T), 193 ($X^{29}$=H or N), 197 ($X^{30}$=G or A), 204 ($X^{31}$=S or L), 222 ($X^{32}$=D or N), 224 ($X^{33}$=T or V), 247 ($X^{34}$=N or D), 270 ($X^{35}$=N or K), 272 ($X^{36}$=K or E), 276 ($X^{37}$=R, Q or K), 287 ($X^{38}$=D or E), 290 ($X^{39}$=L or I), 294 ($X^{40}$=K or R), 309 ($X^{41}$=Q or KO, 327 ($X^{42}$=D or N), 329 ($X^{43}$=L or F), 330 ($X^{44}$=I or V), 332 ($X^{45}$=t or V), 333 ($X^{46}$=f, I or L), 336 ($X^{47}$=K or N), and 338 ($X^{48}$=K or Q).

LukA and LukB leukocidins may differ from the native polypeptides designated as SEQ ID NOS:2-14 and 16-27 respectively, in terms of one or more additional amino acid insertions, substitutions or deletions, e.g., one or more amino acid residues within SEQ ID NOS:2-14 or 16-27 may be substituted by another amino acid of a similar polarity, which acts as a functional equivalent, resulting in a silent alteration. That is to say, the change relative to the native sequence would not appreciably diminish the basic properties of native LukA and LukB. Examples include SEQ ID NOS:1 and 15. Any such analog of LukA or LukB may be screened in accordance with the protocols disclosed herein (e.g., the cell toxicity assay and the membrane damage assay) to determine if it maintains native LukA or LukB activity. Substitutions within these leukocidins may be selected from other members of the class to which the amino acid belongs. For example, nonpolar (hydrophobic) amino acids include alanine, leucine, isoleucine, valine, proline, phenylalanine, tryptophan and methionine. Polar neutral amino acids include glycine, serine, threonine, cysteine, tyrosine, asparagine, and glutamine. Positively charged (basic) amino acids include arginine, lysine and histidine. Negatively charged (acidic) amino acids include aspartic acid and glutamic acid.

In other embodiments, non-conservative alterations (e.g., one or amino acid substitutions, deletions and/or additions) can be made for purposes of inactivating or detoxifying LukA and LukB. In one embodiment, the nontoxic LukA analog differs from the native polypeptides in that the C-terminal amino acids in positions 342-351 are deleted. With the exception of SEQ ID NOs:4-6 (which contain 9 amino acids at these positions), the analog lacks the 10 C-terminal amino acid residues. Collectively, these analogs are referred to as LukAΔ10C. The detoxified LukA and LukB may be used in the active vaccine compositions described herein. Molecular alterations can be accomplished by methods well known in the art, including primer extension on a plasmid template using single stranded templates (Kunkel, Proc. Acad. Sci., USA 82:488-492 (1985)), double stranded DNA templates (Papworth, et al., Strategies 9(3): 3-4 (1996)), and by PCR cloning (Braman, J. (ed.), *IN VITRO MUTAGENESIS PROTOCOLS*, 2nd ed. Humana Press, Totowa, N.J. (2002). Methods of determining whether a given molecular alteration in LukA or LukB reduces LukAB cytotoxicity are described herein.

Therefore, in view of the foregoing and for purposes of the present invention, LukA may be more broadly described in terms of any of SEQ ID NOS:1-14 (e.g., SEQ ID NO:2, which is the LukA polypeptide native to the Newman strain of *S. aureus*), or a (native or non-native) polypeptide having at least about 70%, 75%, 80%, 85%, 90%, 95%, 96%, 97%, 98% or 99% sequence similarity thereto.

Likewise, in view of the foregoing and for purposes of the present invention, LukB may be more broadly described in terms of any of SEQ ID NOS:15-27 (e.g., SEQ ID NO:27, which is the LukB polypeptide native to the Newman strain of *S. aureus*), or a (native or non-native) polypeptide having at least about 70%, 75%, 80%, 85%, 90%, 95%, 96%, 97%, 98% or 99% sequence similarity thereto.

Thus, unless indicated to the contrary, both the immature and the mature forms of native LukA and LukB, and the sequences having less than 100% similarity with native LukA (i.e., native sequences and analogs alike, collectively referred to herein as "LukA" and "LukB") may be used in the compositions and methods, and for making the anti-LukA and the anti-LukB antibodies of the present invention.
Polynucleotides Encoding LukA and LukA and Methods of Synthesizing or Isolating LukA and LukB The LukA and LukB leukocidins may be synthesized via recombinant DNA methodologies which are well known in the art. For example, a nucleotide sequence (designated SEQ ID NO:28) encoding LukA polypeptide of *S. aureus* (Newman) (SEQ ID NO:2), is set forth below. Degenerate sequences (e.g., that may be useful in view of codon preferences in hosts of choice for purposes of recombinant expression) that encode this polypeptide, and polynucleotides that encode other LukA polypeptides are known in the art, or may be designed by persons of skill in the art.

```
atgaaaaataaaaaacgtgttttaatagcgtcatcattatcattttcaattttattgtta
 M  K  N  K  K  R  V  L  I  A  S  S  L  S  C  A  I  L  L  L tcagcagcaacgactcaagcaaattcagctcataaagactctcaagaccaaaataagaaa
 S  A  A  T  T  Q  A  N  S  A  H  K  D  S  Q  D  Q  N  K  K gaacatgttgataagtctcaacaaaaagacaaacgtaatgttactaataaagataaaaat
 E  H  V  D  K  S  Q  Q  K  D  K  R  N  V  T  N  K  D  K  N tcaacagcaccggatgatattgggaaaaacggtaaaatcacaaaacgaactgaaacagta
 S  T  A  P  D  D  I  G  K  N  G  K  I  T  K  R  T  E  T  V tatgatgagaaacaaatatactccaaaatttacaattcgactttatcgatgatccaact
 Y  D  E  K  T  N  I  L  Q  N  L  Q  F  D  F  I  D  D  P  T tatgacaagaatgtattacttgttaaaaaacaaggctcaattcattcaaatttaaagttt
 Y  D  K  N  V  L  L  V  K  K  Q  G  S  I  H  S  N  L  K  F gaatctcataaagaagaaaaaattcaaattggttaaagtatccaagtgagtaccatgta
 E  S  H  K  E  E  K  N  S  N  W  L  K  Y  P  S  E  Y  H  V gattttcaagtaaaaagaaatcgtaaaactgaaatattagaccaattgccgaaaaataaa
 D  F  Q  V  K  R  N  R  K  T  E  I  L  D  Q  L  P  K  N  K atttcaactgcaaaagtagacagtacattttcatatagctcaggtggtaaattcgattca
 I  S  T  A  K  V  D  S  T  F  S  Y  S  S  G  G  K  F  D  S acaaaaggtattggacgaacttcatcaaatagctactccaaaacgattagttataatcag
 T  K  G  I  G  R  T  S  S  N  S  Y  S  K  T  I  S  Y  N  Q caaaattatgacacaattgccagcggtaaaaataataactggcatgtacactggtcagtt
 Q  N  Y  D  T  I  A  S  G  K  N  N  N  H  V  H  W  S  V attgcgaatgacttgaagtatggtggagaagtgaaaaatagaaatgatgaattattattc
 I  A  N  D  L  K  Y  G  G  E  V  K  N  R  N  D  E  L  L  F
```

-continued

```
tatagaaatacgagaattgctactgtagaaaaccctgaactaagctttgcttcaaaatat
 Y  R  N  T  R  I  A  T  V  E  N  P  E  L  S  F  A  S  K  Y agatacccagcattagtaagaagtggctttaatccagaattttttaacttatttatctaat
 R  Y  P  A  L  V  R  S  G  F  N  P  E  F  L  T  Y  L  S  N gaaaagtcaaatgagaaaacgcaatttgaagtaacatacacacgaaatcaagatattttg
 E  K  S  N  E  K  T  Q  F  E  V  T  Y  T  R  N  Q  D  I  L aaaaacagacctggaatacattatgcacctccaatttttagaaaaaaaataaagatggtcaa
 K  N  R  P  G  I  H  Y  A  P  P  I  L  E  K  N  K  D  G  Q agattaattgtcacttatgaagttgattggaaaaataaaacagttaaagtcgttgataaa
 R  L  I  V  T  Y  E  V  D  W  K  N  K  T  V  K  V  V  D  K tattctgatgacaataaaccttataaagaaggataa
 Y  S  D  D  N  K  P  Y  K  E  G
```

A nucleotide sequence (designated herein as SEQ ID NO:29) that encodes LukB polypeptide of S. aureus (Newman), (SEQ ID NO:27), is set forth below. Degenerate sequences (e.g., that may be useful in view of codon preferences in hosts of choice for purposes of recombinant expression) that encode this polypeptide, and polynucleotides that encode other LukB polypeptides are known in the art, or may be designed by persons of skill in the art.

```
atgattaaacaactatgtaaaaatatcacaatttgtacgttagcactatcgactactttc
 M  I  K  Q  L  C  K  N  I  T  I  C  T  L  A  L  S  T  T  F actgtattaccagctacttcatttgcaaagattaattctgaaatcaaacaagtttctgag
 T  V  L  P  A  T  S  F  A  K  I  N  S  E  I  K  Q  V  S  E aagaatcttgatggtgatactaaaatgtatacacgtacagctacaacaagtgatagtcaa
 K  N  L  D  G  D  T  K  M  Y  T  R  T  A  T  T  S  D  S  Q aaaaatattactcaaagcttacaatttaatttcttaactgaacctaattatgataaagaa
 K  N  I  T  Q  S  L  Q  F  N  F  L  T  E  P  N  Y  D  K  E acagtatttattaaagcaaaaggtacaattggtagtggtttgagaattttagacccaaat
 T  V  F  I  K  A  K  G  T  I  G  S  G  L  R  I  L  D  P  N ggttattggaatagtacattaagatggcctggatcttattcagtttcaattcaaaatgtt
 G  Y  W  N  S  T  L  R  W  P  G  S  Y  S  V  S  I  Q  N  V gatgacaacaacaatacaaatgtgactgactttgcaccaaaaaatcaggatgaatcaaga
 D  D  N  N  N  T  N  V  T  D  F  A  P  K  N  Q  D  E  S  R gaagttaaatatacgtatggttatataaaacaggtggagattttcgattaatcgtggaggc
 E  V  K  Y  T  Y  G  Y  K  T  G  G  D  F  S  I  N  R  G  G ttaactggaaatattacaaaagagagtaattattcagagacgattagttatcaacaacca
 L  T  G  N  I  T  K  E  S  N  Y  S  E  T  I  S  Y  Q  Q  P tcatatcgtacattacttgatcaatctacgtcacataaaggtgtaggttggaaagtagaa
 S  Y  R  T  L  L  D  Q  S  T  S  H  K  G  V  G  W  K  V  E gcacatttgataaataatatgggacatgaccatacgagacaattaactaatgatagtgat
 A  H  L  I  N  N  M  G  H  D  H  T  R  Q  L  T  N  D  S  D aatagaactaaaagtgaaatttttctttaacacgaaatggaaatttatgggcgaaagat
 N  R  T  K  S  E  I  F  S  L  T  R  N  G  N  L  W  A  K  D aatttcacacctaaagacaaaatgcctgtaactgtgtctgaagggtttaatccagaattt
 N  F  T  P  K  D  K  M  P  V  T  V  S  E  G  F  N  P  E  F ttagctgttatgtcacatgataaaaaagacaaaggtaaatcacaatttgttgttcattat
 L  A  V  M  S  H  D  K  K  D  K  G  K  S  Q  F  V  V  H  Y aaaagatcaatggatgagtttaaaatagattggaatcgccatggtttctggggctattgg
 K  R  S  M  D  E  F  K  I  D  W  N  R  H  G  F  W  G  Y  W tctggtgaaaaccatgtagataaaaaagaagaaaaattataagcattatatgaagttgat
 S  G  E  N  H  V  D  K  K  E  E  K  L  S  A  L  Y  E  V  D tggaagacacataatgtgaagtttgtaaaagtacttaatgataatgaaaagaaataa
 W  K  T  H  N  V  K  F  V  K  V  L  N  D  N  E  K  K  -
```

The LukA- and LukB-encoding polynucleotides may be expressed in a host such as bacteria (E. coli), plants and or yeast and then isolated and purified. Alternatively, LukA and LukB leukocidins may be isolated from S. aureus bacteria (e.g., the Newman strain) in accordance with standard techniques. Thus, these leukocidins may be isolated (from a native or non-native environment). They may also be purified in that they are substantially free from other proteins and cell components with which S. aureus LukA and LukB are associated in their native state (i.e., proteins and cell components present in S. aureus cells) or a non-native state (i.e., proteins and cell components of a recombinant cellular host). Suitable purification schemes, which typically entail a combination of at least two successive procedures, are known in the art. See, Deutscher, Methods in Enzymology, 182 (1990); and Scopes, Protein Purification: Principles and Practice, Springer-Verlag, N.Y. (1982), using one or a combination of two or more standard techniques such as affinity column chromatography and cation-exchange liquid chromatography.

Anti-LukA Antibodies and Anti-LukB Antibodies

Aspects of the present invention are directed to anti-LukA antibodies that specifically bind LukA, and anti-LukB antibodies that specifically bind LukB, therapeutic compositions containing the antibodies, and methods of use thereof. For purposes of the present invention, the term "antibody" includes monoclonal antibodies, polyclonal antibodies, antibody fragments, and genetically engineered forms of the antibodies, and combinations thereof. More specifically, the term "antibody", which is used interchangeably with the term "immunoglobulin", includes full-length (i.e., naturally occurring or formed by normal immunoglobulin gene fragment recombinatorial processes) immunoglobulin molecules (e.g., an IgG antibody) and immunologically active fragments thereof (i.e., including the specific binding portion of the full-length immunoglobulin molecule), which again may be naturally occurring or synthetic in nature. Accordingly, the term "antibody fragment" includes a portion of an antibody such as F(ab')$_2$, F(ab)$_2$, Fab', Fab, Fv, scFv and the like. Regardless of structure, an antibody fragment binds with the same antigen that is recognized by the full-length antibody, and, in the context of the present invention, specifically binds LukA, LukB or a LukAB complex. Methods of making and screening antibody fragments are well-known in the art.

In some embodiments, the anti-LukA antibodies of the present invention may have some degree of cross-reactivity with other Staphylococcus leukocidin S-subunits such as HlgC, LukS-PVL, HlgA, LukS-I, LukE, LukEv, and LukM. Likewise, in some embodiments, the anti-LukB antibodies of the present invention may have some degree of cross-reactivity with other Staphylococcus leukocidin F-subunits such as LukF'-PV, LukF-PV, LukDv, LukD, LukF-I, and HlgB. Anti-LukA and/or anti-LukB antibodies may inhibit or reduce LukA activity and LukB activity, respectively. In some embodiments, the anti-LukA and/or anti-LukB antibodies neutralize (e.g., substantially eliminate) LukA and LukB activity, respectively.

Naturally occurring antibodies typically have two identical heavy chains and two identical light chains, with each light chain covalently linked to a heavy chain by an interchain disulfide bond and multiple disulfide bonds further link the two heavy chains to one another. Individual chains can fold into domains having similar sizes (110-125 amino acids) and structures, but different functions. The light chain can comprise one variable domain (VL) and/or one constant domain (CL). The heavy chain can also comprise one variable domain (VH) and/or, depending on the class or isotype of antibody, three or four constant domains (CH1, CH 2, CH3 and CH4). In humans, the isotypes are IgA, IgD, IgE, IgG, and IgM, with IgA and IgG further subdivided into subclasses or subtypes (IgA1-2 and IgG1-4).

Generally, the variable domains show considerable amino acid sequence variability from one antibody to the next, particularly at the location of the antigen-binding site. Three regions, called hyper-variable or complementarity-determining regions (CDRs), are found in each of VL and VH, which are supported by less variable regions called framework variable regions. The inventive antibodies include IgG monoclonal antibodies but the antibodies of the present invention also include antibody fragments or engineered forms. These are, for example, Fv fragments, or proteins wherein the CDRs and/or variable domains of the exemplified antibodies are engineered as single-chain antigen-binding proteins.

The portion of an antibody consisting of the VL and VH domains is designated as an Fv (Fragment variable) and constitutes the antigen-binding site. A single chain Fv (scFv or SCA) is an antibody fragment containing a VL domain and a VH domain on one polypeptide chain, wherein the N terminus of one domain and the C terminus of the other domain are joined by a flexible linker. The peptide linkers used to produce the single chain antibodies are typically flexible peptides, selected to assure that the proper three-dimensional folding of the VL and VH domains occurs. The linker is generally 10 to 50 amino acid residues, and in some cases is shorter, e.g., about 10 to 30 amino acid residues, or 12 to 30 amino acid residues, or even 15 to 25 amino acid residues. An example of such linker peptides includes repeats of four glycine residues followed by a serine residue.

Single chain antibodies lack some or all of the constant domains of the whole antibodies from which they are derived. Therefore, they can overcome some of the problems associated with the use of whole antibodies. For example, single-chain antibodies tend to be free of certain undesired interactions between heavy-chain constant regions and other biological molecules. Additionally, single-chain antibodies are considerably smaller than whole antibodies and can have greater permeability than whole antibodies, allowing single-chain antibodies to localize and bind to target antigen-binding sites more efficiently. Furthermore, the relatively small size of single-chain antibodies makes them less likely to provoke an unwanted immune response in a recipient than whole antibodies.

Fab (Fragment, antigen binding) refers to the fragments of the antibody consisting of the VL, CL, VH, and CH1 domains. Those generated following papain digestion simply are referred to as Fab and do not retain the heavy chain hinge region. Following pepsin digestion, various Fabs retaining the heavy chain hinge are generated. Those fragments with the interchain disulfide bonds intact are referred to as F(ab')2, while a single Fab' results when the disulfide bonds are not retained. F(ab')$_2$ fragments have higher avidity for antigen that the monovalent Fab fragments.

Fc (Fragment crystallization) is the designation for the portion or fragment of an antibody that comprises paired heavy chain constant domains. In an IgG antibody, for example, the Fc comprises CH2 and CH3 domains. The Fc of an IgA or an IgM antibody further comprises a CH4 domain. The Fc is associated with Fc receptor binding, activation of complement-mediated cytotoxicity and antibody-dependent cellular-cytotoxicity (ADCC). For antibodies such as IgA and IgM, which are complexes of multiple IgG-like proteins, complex formation requires Fc constant domains.

Finally, the hinge region separates the Fab and Fc portions of the antibody, providing for mobility of Fabs relative to each other and relative to Fc, as well as including multiple disulfide bonds for covalent linkage of the two heavy chains.

Antibody "specificity" refers to selective recognition of the antibody for a particular epitope of an antigen. The term "epitope" includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. An epitope may be "linear" or "conformational". In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another, i.e., noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation. Antibodies that recognize the same epitope can be verified in a simple immunoassay showing the ability of one antibody to block the binding of another antibody to a target antigen.

Monoclonal antibodies of the present invention may be murine, human, humanized or chimeric. A humanized antibody is a recombinant protein in which the CDRs of an antibody from one species; e.g., a rodent, rabbit, dog, goat, horse, or chicken antibody (or any other suitable animal antibody), are transferred from the heavy and light variable chains of the rodent antibody into human heavy and light variable domains. The constant domains of the antibody molecule are derived from those of a human antibody. Methods for making humanized antibodies are well known in the art. Chimeric antibodies preferably have constant regions derived substantially or exclusively from human antibody constant regions and variable regions derived substantially or exclusively from the sequence of the variable region from a mammal other than a human. The chimerization process can be made more effective by also replacing the variable regions—other than the hyper-variable regions or the complementarity—determining regions (CDRs), of a murine (or other non-human mammalian) antibody with the corresponding human sequences. The variable regions other than the CDRs are also known as the variable framework regions (FRs). Yet other monoclonal antibodies of the present invention are bi-specific, in that they have specificity for both LukA and LukB. Bispecific antibodies are preferably human or humanized.

The above-described antibodies can be obtained in accordance with standard techniques. For example, LukA, LukB (which as these terms are used herein, include nontoxic analogs thereof such as LukAΔ10C) or an immunologically active fragment of LukA or LukB can be administered to a subject (e.g., a mammal such as a human or mouse). The leukocidins can be used by themselves as immunogens or they can be attached to a carrier protein or other objects, such as beads such as sepharose beads. After the mammal has produced antibodies, a mixture of antibody producing cells, such as splenocytes, are isolated, from which polyclonal antibodies may be obtained. Monoclonal antibodies may be produced by isolating individual antibody-producing cells from the mixture and immortalizing them by, for example, fusing them with tumor cells, such as myeloma cells. The resulting hybridomas are preserved in culture and the monoclonal antibodies are harvested from the culture medium.

Techniques for making recombinant monoclonal antibodies are well known in the art. Recombinant polyclonal antibodies can be produced by methods analogous to those described in U.S. Patent Application Publication 2002/0009453, using LukA, LukB or LukAB as the immunogen(s).

Therapeutic Compositions

LukA and LukB may be formulated into a therapeutic composition for use as an anti-inflammatory agent in the treatment of acute inflammatory conditions, including localized acute inflammatory conditions. LukA and LukB may also be formulated into a therapeutic composition for use as an active vaccine. Anti-LukA and anti-LukB antibodies may be formulated into a therapeutic composition for use as a passive vaccine. The passive and active vaccines may be used prophylactically to inhibit onset of a *S. aureus* infection, or therapeutically to treat *S. aureus* infection, particularly *S. aureus* infections such as MRSA that are known to be refractory or in the case of the specific subject, have proven refractory to treatment with other conventional antibiotic therapy.

In embodiments wherein the therapeutic composition is intended for use as an active vaccine, the LukA and/or LukB may be altered so as to exhibit reduced toxicity. Molecular alterations are described above. Thus, nontoxic analogs thereof such as LukAΔ10C may be used. Applicants believe that antibodies produced in response to the nontoxic immunogen will neutralize the toxic, native LukA or LukAB. Other alterations for purposes of reducing toxicity of LukA and LukB include chemical treatment (e.g., modification of specific amino acid residues) or conjugation to another moiety (e.g., to another bacterial antigen, such as a bacterial polysaccharide or a bacterial glycoprotein). Chemical alterations to other *S. aureus* toxins for purposes of inactivation or detoxification (or reducing toxicity) are known. Methods of determining whether a given alteration reduces LukA or LukB toxicity are known in the art and/or described herein.

The therapeutic compositions of the present invention are prepared by formulating LukA and LukB, or anti-LukA and anti-LukB antibodies, with a pharmaceutically acceptable carrier and optionally a pharmaceutically acceptable excipient. As used herein, the terms "pharmaceutically acceptable carrier" and "pharmaceutically acceptable excipient" (e.g., additives such as diluents, immunostimulants, adjuvants, antioxidants, preservatives and solubilizing agents) are nontoxic to the cell or mammal being exposed thereto at the dosages and concentrations employed. Examples of pharmaceutically acceptable carriers include water, e.g., buffered with phosphate, citrate and another organic acid. Representative examples of pharmaceutically acceptable excipients that may be useful in the present invention include antioxidants such as ascorbic acid; low molecular weight (less than about 10 residues) polypeptides; proteins, such as serum albumin, gelatin, or immunoglobulins; adjuvants (selected so as to avoid adjuvant-induced toxicity, such as a β-glucan as described in U.S. Pat. No. 6,355,625, or a granulocyte colony stimulating factor (GCSF)); hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt forming counterions such as sodium; and/or nonionic surfactants such as TWEEN®, polyethylene glycol (PEG), and PLURONICS®.

As described elsewhere herein, the therapeutic compositions of the present invention may further contain at least one additional active agent.

Therapeutic compositions of the present invention may be prepared for storage by mixing the active ingredient(s) having the desired degree of purity with the pharmaceutically acceptable carrier and optional excipient and/or additional active agent, in the form of lyophilized formulations or aqueous solutions.

Uses of the Therapeutic Compositions—Indications
Acute Inflammatory Conditions

Inflammation is generally understood as the protective biological response to remove harmful invading stimuli such as pathogens (e.g., bacteria and viruses), damaged cells and irritants, and to initiate healing. Inflammation is understood more specifically as the reaction of vascularized living tissue to injury. As such, inflammation is a fundamental, stereotyped complex of cytological and chemical reactions of affected blood vessels and adjacent tissues in response to an injury or abnormal stimulation caused by a physical, chemical or biological agent. Inflammation usually leads to the accumulation of fluid and blood cells at the site of injury, and is usually a healing process. Without the inflammatory process, wounds and infections would not heal, and progressive destruction of the tissue would become life-threatening. Acute inflammation refers to the initial response of the body to invading stimuli and involves the recruitment of plasma and white blood cells (leukocytes) to the injured or infected tissues. Prolonged inflammation, also referred to as chronic inflammation, involves a progressive shift in the type of immune cells which are present at the site of inflammation, and is characterized by simultaneous destruction and healing of the tissue from the inflammatory process.

However, inflammation sometimes causes harm, usually through a dysfunction of the normal progress of inflammation. Inflammatory diseases are those pertaining to, characterized by, causing, resulting from, or becoming affected by inflammation. "Acute inflammatory conditions" as the term is used herein, and in accordance with normal medical parlance, refers to inflammatory conditions having a rapid onset and severe symptoms. The duration of the onset, from a normal condition of the patient to one in which symptoms of inflammation are seriously manifested, generally lasts up to about 72 hours. Acute inflammatory conditions are to be contrasted with chronic inflammatory conditions, which are inflammatory conditions of long duration, denoting a disease showing little change or of slow progression. The distinction between acute and chronic conditions is well known to those in the medical professions.

The major immune cells involved in the acute stage of inflammation, as well as in acute inflammatory disorders, include mononuclear cells (e.g., monocytes, which in response to inflammation differentiate into macrophages), dendritic cells, and neutrophils (which migrate to the inflammatory site). These immune cells aid in the inflammatory response by releasing inflammatory mediators such as histamine, interferon-gamma, interleukin-8, leukotriene B4, nitric oxide, etc., and by ingesting bacteria, viruses and cellular debris (a process known as phagocytosis). These cells are known in the art collectively as phagocytes.

Applicants have discovered that LukAB targets and kills human phagocytes and that this LukAB-mediated cytotoxicity is substantially specific to these cells but not other nucleated mammalian cells. Without intending to be bound by any particular theory of operation, Applicants believe that the LukA/LukB complex forms pores on the plasma membrane of infiltrating phagocytes, causing cell death, thus reducing the inflammation. Thus, the anti-inflammatory compositions of the present invention may be useful in treating acute inflammatory conditions in mammals such as humans, regardless of the cause, e.g., any bacterial or viral infection, and in preferred embodiments, localized acute inflammatory conditions. Other examples of such conditions include allergic contact dermatitis, acute hypersensitivity, acute neurological inflammatory injury (e.g., caused by acute infection), acute myocardial infarction, acute neuronal injury resulting from cardiopulmonary bypass surgery, and acute, localized anti-inflammatory conditions caused by bacterial or viral infection.

In preferred embodiments, the acute inflammatory condition is an infected wound in the skin or soft tissue. Wounds amenable to treatment with the invention may be in the form of punctures, cuts or tears of the living tissues. Wounds of the skin can penetrate the epidermis, dermis or in the case of full-thickness wounds, the subcutaneous tissue. Thus, wounds treatable with the therapeutic compositions of the present invention include deep sternal wounds, e.g., following open heart surgery and post-operative wounds following abdominal and any other types of surgery. Other wounds are those which result from trauma such as by gun shots, knives, or any other object able to cause a cut or tear in the skin. Wounds that arise as a side-effect of medication or as a symptom of various pathologies (e.g., sores associated with Kaposi's Sarcoma), as well as internal wounds (e.g. anal fissures, and wounds or lesions to the gastrointestinal tract, such as ulcers in the stomach or intestines) may also be amenable to treatment with the present invention.

Yet other acute inflammatory conditions that may be amenable to treatment with the therapeutic compositions of the present invention include conjunctivitis, iritis, uveitis, central retinitis, external otitis, acute suppurative otitis media, mastoiditis, labyrinthitis, chronic rhinitis, acute rhinitis, sinusitis, pharyngitis, tonsillitio, contact dermatitis, dermonecrosis, diabetic polyneuritis, polymyositis, myositis ossificans, degenerative arthritis, rheumatoid arthritis, periarthritis scapulohumeralis, and osteitis deformans.

S. aureus Infections

The present invention also provides a method of inhibiting onset of or treating S. aureus infection by administering the antibody compositions to a mammalian subject in need thereof. For purposes of the present invention, the target subject population includes mammals, such as humans, who are infected with, or at risk of being infected by S. aureus. In some embodiments, the subject to be treated is infected with S. aureus including MRSA, and/or has already been treated with antibiotics or other therapeutic agents, but the treatment has failed.

Therapeutically Effective Amounts

In the context of treatment of acute inflammatory conditions, the amounts of LukA and LukB are therapeutically effective in the sense that treatment is capable of achieving any one or more of a reduction in the number of symptoms, a decrease in the severity of at least one symptom, or a delay in the further progression of at least one symptom, or even a total alleviation of the acute inflammatory condition.

In the context of use of the therapeutic compositions as passive or active vaccines in connection with S. aureus infection, the therapeutically effective amounts of LukA and LukB, or anti-LukA and anti-LukB antibodies, are also prophylactically effective in the sense that administration of the composition is capable of achieving any one or more of inhibition or prevention of an S. aureus infection in those who are at risk, and in terms of mammalian subjects infected with *S. aureus*, a reduction in the number of symptoms, a decrease in the severity of at least one symptom, or a delay in the further progression of at least one symptom, or even a total alleviation of the infection.

Broadly, the therapeutically effective amounts of LukA, LukB, and anti-LukA and anti-LukB antibodies can be determined in accordance with standard procedures, which take numerous factors into account, including, for example, the concentrations of these active agents in the composition, the mode and frequency of administration, the severity of the acute inflammatory condition or *S. aureus* infection to be treated (or prevented), and subject details, such as age, weight and overall health and immune condition. General guidance can be found, for example, in the publications of the International Conference on Harmonization and in REMINGTON'S PHARMACEUTICAL SCIENCES (Mack Publishing Company 1990). A clinician may administer LukA and LukB or anti-LukA and anti-LukB antibodies, until a dosage is reached that provides the desired or required prophylactic or therapeutic effect. The progress of this therapy can be easily monitored by conventional assays.

Therapeutically effective amounts of LukA and LukB typically range from 1-400 µg of each of LukA and LukB, per dose or on a daily basis. Preferably, the amounts of LukA and LukB are substantially the same. Therapeutically effective amounts of the antibody compositions typically are at least 50 mg composition per kilogram of body weight (mg/kg), including at least 100 mg/kg, at least 150 mg/kg, at least 200 mg/kg, at least 250 mg/kg, at least 500 mg/kg, at least 750 mg/kg and at least 1000 mg/kg, per dose or on a daily basis. Dosages for monoclonal antibody compositions might tend to be lower, such as about one-tenth of non-monoclonal antibody compositions, such as at least about 5 mg/kg, at least about 10 mg/kg, at least about 15 mg/kg, at least about 20 mg/kg, or at least about 25 mg/kg.

Modes of Administration

Prior to administration, the therapeutic compositions of the present invention may be sterilized which can be readily accomplished by filtration through sterile filtration membranes, prior to or following lyophilization and reconstitution. Therapeutic compositions may be placed into a container having a sterile access port, for example, an intravenous solution bag or vial having a stopper pierceable by a hypodermic injection needle.

The anti-inflammatory composition may be administered by any number of routes in accordance with accepted medical practice. Preferred modes include intravenous, intramuscular, subcutaneous and percutaneous administration, using techniques that are known in the art. Other routes of administration may be envisioned. In the case of treatment of acute inflammatory conditions that are localized, non-systemic administration may be preferred in which case the administration of the therapeutic composition is at or around the site of the acute inflammation.

Combination Therapy

In some embodiments, the therapeutic composition is administered as part of a combination therapy in conjunction with another active agent, depending upon the nature of the acute inflammatory condition or the *S. aureus* infection that is being treated. Such additional active agents include anti-infective agents, antibiotic agents, and antimicrobial agents. Representative anti-infective agents that may be useful in the present invention include vancomycin and lysostaphin. Representative antibiotic agents and antimicrobial agents that may be useful in the present invention include penicillinase-resistant penicillins, cephalosporins and carbapenems, including vancomycin, lysostaphin, penicillin G, ampicillin, oxacillin, nafcillin, cloxacillin, dicloxacillin, cephalothin, cefazolin, cephalexin, cephradine, cefamandole, cefoxitin, imipenem, meropenem, gentamycin, teicoplanin, lincomycin and clindamycin. Dosages of these antibiotics are well known in the art. See, e.g., MERCK MANUAL OF DIAGNOSIS AND THERAPY, Section 13, Ch. 157, $100^{th}$ Ed. (Beers & Berkow, eds., 2004). The anti-inflammatory, anti-infective, antibiotic and/or antimicrobial agents may be combined prior to administration, or administered concurrently (as part of the same composition or by way of a different composition) or sequentially with the inventive therapeutic compositions of the present invention.

In some embodiments, the anti-LukA and/or anti-LukB antibody composition is multivalent in that it also contains an antibody that specifically binds another bacterial antigen (and that optionally neutralizes the other bacterial antigen). The antibodies may specifically bind any of the antigens described herein in the context of the vaccine compositions. Thus, for example, the other antibody may specifically bind polysaccharides or glycoproteins, including *S. aureus* Type 5, *S. aureus* Type 8, *S. aureus* 336, leukocidin components such as PVL (including the individual PVL subunits, LukS-PV and LukF-PV) gamma-hemolysin subunits (HlgA, HlgB, and HlgC), LukE or LukD from *S. aureus*, LukM or LukF'-PV from *S. aureus*, lipoteichoic acid (LTA) and microbial surface components recognizing adhesive matrix molecule (MSCRAMM) proteins.

Treatment Regimens

Therapeutic compositions of the present invention may be administered in a single dose, or in accordance with a multi-dosing protocol. For example, relatively few doses of the therapeutic composition are administered, such as one or two doses. In embodiments that include conventional antibiotic therapy, which generally involves multiple doses over a period of days or weeks, the antibiotics can be taken one, two or three or more times daily for a period of time, such as for at least 5 days, 10 days or even 14 or more days, while the antibody composition is usually administered only once or twice. However, the different dosages, timing of dosages and relative amounts of the therapeutic composition and antibiotics can be selected and adjusted by one of ordinary skill in the art.

Methods of Identifying Inhibitors of LukAB-mediated Cytotoxicity and Altered Forms of LukA and LukB that have Less Toxicity The anti-LukA and anti-LukB antibodies, and fragments thereof, as well as other potential therapeutic moieties (e.g., small organic molecules) may be used in various methods (including assay formats or screens) to evaluate their ability to inhibit LukAB-mediated cytotoxicity. As described below, these methods are designed to identify agents that inhibit some aspect of the cascade of events that leads to LukAB-mediated cytotoxicity and lysis of human phagocytes. The methods are also designed to identify altered forms of LukA and LukB that possess reduced toxicity relative to their native counterparts. The targeted events that are part of the cascade include for example, binding of LukA to phagocyte membranes, binding of LukB to LukA (LukAB oligomerization), and blockage of the membrane pore formed by the LukAB oligomer. The assay formats generally require human phagocytes (or LukAB membrane-binding portion thereof), suitable culture medium, and purified LukA or purified LukA and LukB.

The person of skill will appreciate that the following protocols are merely illustrative and that various operating parameters such as reaction conditions, choice of detectable label and apparati (e.g., instrumentation for detection and quantification) may be varied as deemed appropriate.

The following methods are generally directed to identifying agents that inhibit LukAB cytotoxicity, without necessarily revealing the exact event in the cascade that is affected.

To identify inhibitors of LukAB cytotoxicity, human phagocytes (e.g., PMN-HL60 cells) may be plated in 384-well clear-bottom black tissue culture treated plate (Corning) at $5\times10^3$ cells/well in a final volume of 50 µl of RPMI (Gibco) supplemented with 10% of heat inactivated fetal bovine serum (FBS). Cells may then be contacted/mixed/reacted/treated with the test compound/molecule (~5 µl/different concentrations) and then intoxicated with LukA and LukB, which in preferred embodiments are substantially purified (5 ul of a ~0.001-2 µM solution), preferably added together, under culture conditions to allow for intoxication of the phagocytes by LukA and LukB, e.g., for 1 hr at 37° C., 5% $CO_2$. As controls, cells may be treated with culture medium (100% viable) and with 0.1% v/v Triton X100 (100% death).

In these embodiments, cells treated as described above may then be incubated with a dye to monitor cell viability (which enables determination of cell viability via absorbance by measuring the number of viable cells in a culture by quantification of the metabolic activity of the cells) and incubated for an additional time period (e.g., about 2 hrs at 37° C., 5% $CO_2$). Cell viability may then be determined such as by measuring the colorimetric reaction at 492 nm using a plate reader e.g., Envision 2103 Multi-label Reader (Perkin-Elmer). Percent viable cells may be calculated such as by using the following equation: % Viability=100× [($Ab_{492}$Sample−$Ab_{492}$Triton X)/($Ab_{492}$Tissue culture media). An increase in the 100% viability suggests inhibition of LukAB cytotoxicity.

A variation of this assay is referred to as a membrane damage assay. In these embodiments, cells treated as described above (e.g., up to and including treating of the cells with test compound/molecule and then intoxicating the cells with purified LukA may then be incubated with a cell-impermeable fluorescent dye such as SYTOX green (0.1 µM; Invitrogen) (in accordance with manufacturer's instructions) and incubated e.g., for an additional 15 minutes at room temperature in the dark. Fluorescence, as an indicator of membrane damage, may then be measured using a plate reader such as Envision 2103 Multilabel Reader (Perkin-Elmer) at Excitation 485 nm, Emission 535 nm. A decrease in fluorescence suggests inhibition of LukAB cytotoxicity.

Together these assays facilitate the identification of compounds that inhibit or reduce LukAB cytotoxic effects towards human phagocyte cells.

Additional methods may be used, independently or in conjunction with the methods described above, particularly if the above methods reveal inhibitory activity, that will enable a person skilled in the field to determine more precisely what event in the biochemical cascade is being affected or targeted by the agent. These events include binding of LukA to phagocyte membranes, binding of LukB to LukA (LukAB oligomerization), and blockage of the membrane pore formed by the LukAB oligomer.

Screen for Inhibitors of LukA Binding to Target Cells

To screen for inhibitors that block or reduce LukA binding to target cells, which is believed to be the first step in the intoxication process, human phagocytes (e.g., PMN-HL60 cells) may be plated in 384-well flat-bottom tissue culture treated plates (Corning) at $2.5\times10^3$ cells/well in a final volume of 50 µl of RPMI (Gibco) supplemented with 10% of heat inactivated fetal bovine serum (FBS). Cells may then be treated with the test compound/molecule (~5 µl/different concentrations) and intoxicated with purified, fluorescently labeled LukA (e.g., FITC, Cy3, Cy5, APC, PE) 5 ul of a ~0.01-2 µM solution for 1 hr at 37° C., 5% $CO_2$. To evaluate the efficacy of the tested compounds/molecules, the cell-associated fluorescence may be measured as an indicator of LukA binding to cells e.g., using an automated fluorescence microscopic imaging system designed for high content screening and high content analysis (e.g., Cellomics ArrayScan HCS Reader (Thermo Scientific) (Excitation 485 nm, Emission 535 nm)).

Screen for Inhibitors of LukA-LukB Oligomerization/Interaction

To screen for inhibitors that block or reduce LukA/LukB interaction, which is believed to be the second step in the intoxication process, human phagocytes (e.g., PMN-HL60 cells) may be plated in 384-well flat-bottom tissue culture treated plates (Corning) at $2.5\times10^3$ cells/well in a final volume of 50 µl of RPMI (Gibco) supplemented with 10% of heat inactivated fetal bovine serum (FBS). Cells may then be treated with the test compound/molecule and then intoxicated with a mixture of purified LukA and purified LukB where LukB is fluorescently-labeled with a fluorescence molecule such as FITC, Cy3, Cy5, APC, and PE, and allowed to stand to complete the intoxication process (e.g., for 1 hr at 37° C., 5% $CO_2$). To evaluate the efficacy of the tested compounds/molecules, cell-associated LukB-FITC fluorescence may be measured as an indicator of LukA/LukB-FITC interaction, using for example, an automated fluorescence microscopic imaging system designed for high content screening and high content analysis (e.g., a Cellomics ArrayScan HCS Reader (Thermo Scientific) (Excitation 485 nm, Emission 535 nm)).

Screen for Inhibitors of LukAB Pore Formation

To screen for inhibitors that block or inhibit formation of the LukAB pore, the effector molecule that leads to cell lysis, human phagocytes (e.g., PMN-HL60 cells) may be plated in 384-well clear-bottom black tissue culture treated plate (Corning) at $2.5\times10^3$ cells/well in a final volume of 50 µl of RPMI (Gibco) supplemented with 10% of heat inactivated fetal bovine serum (FBS). Cells may then be treated with the test compound/molecule (~5 µl containing different concentrations) and then intoxicated with purified LukAB (~0.001-2 µM) for 10 minutes at 37° C., 5% $CO_2$. As controls, PMN-HL60 cells may be treated with culture medium (negative control) and with 0.1% v/v Triton X100 (positive control).

To directly evaluate LukAB pores on the surface of host cells, an ethidium bromide (EB) influx assay may be used. EB is a small-cationic dye that is impermeable into healthy host cells. Upon formation of cationic pores by LukAB, EB enters the cells and binds to DNA, which results in fluorescence. Cell treated in this fashion may then be incubated with EB (5 µM) for an additional 5 minutes at room temperature in the dark. To evaluate the efficacy of the tested compounds/molecules in inhibiting LukAB pore-formation the fluorescence may be measured as an indicator of pore-formation, using a plate-reader such as the Envision 2103 Multilabel Reader (Perkin-Elmer) at Excitation 530 nm, Emission 590 nm. This assay facilitates the identification of molecules that can block or inhibit the LukAB pore, which will alleviate LukAB-mediated toxicity.

Method to Determine the Production of LukAB by *S. aureus* Clinical Isolates to Predict Severity of Infection An even further aspect of the present invention is directed to a method of predicting or assessing severity of an *S. aureus* infection which entails detecting presence or amount of LukA and/or LukB, or their corresponding genes, in a biological sample obtained from an infected subject. Thus, detection of presence or relatively high amounts of LukA and/or LukB, or detection of their corresponding genes (e.g., as exhibited by *S. aureus* strain Newman, 4645, and MRSA strains USA300 and USA500) relative to a control (e.g., *S. aureus* strains USA100 and USA400) which produces little or undetectable amounts of LukA and/or LukB, is indicative of a severe infection. In regard to detection or presence of relative amounts of LukA and/or LukB, reference may be made to the illustrations in FIG. 4A. Representative embodiments of the method are described below.

Immunoblot Analysis to Determine LukA and LukB Levels

To determine LukAB levels (i.e., LukAB production), the biological sample e.g., a fluid (e.g., blood) or tissue sample, is obtained from the infected subject, followed by exposing the culture to suitable culture conditions to allow for growth of the *S. aureus*, obtaining culture supernatant, separating bacterial proteins therefrom, identifying LukA and/or LukB, and then quantifying LukA and/or LukB. More specifically, in one embodiment, the clinical isolate strains may be selected and grown in a suitable culture medium, e.g., Royal Park Memorial Institute culture medium 1640 (RPMI; Invitrogen) supplemented with 1% casamino acids (RPMI+CAS) under suitable culture conditions, e.g., for 12-18 hours at 37° C. with shaking at 180 rpm. Bacteria may then be precipitated via centrifugation and culture supernatants collected. Culture supernatants (~30 μl) may then be mixed with 10 μl of SDS-Laemmli buffer and boiled at 95° C. for 10 minutes. Proteins may then be separated e.g., using 15% SDS-PAGE gels and then transferred to a solid support, e.g., a nitrocellulose membrane. The membranes may then be incubated with antibodies directed against LukA or LukB (e.g., rabbit polyclonal antibodies), and the presence of LukA or LukB may be visualized by detecting the antibody-LukA/antibody-LukB complexes with a secondary antibody conjugated to a fluorophore (e.g., anti-rabbit antibody conjugated to AlexaFluor-680; Invitrogen). Membranes may then be dried and scanned e.g., using an Odyssey infrared imaging system (LI-COR Biosciences) to determine the amounts of LukA and LukB. Polymerase chain reaction (PCR) to determine the presence of the LukA and/or LukB genes.

To determine the presence of the genes encoding for LukAB, the biological sample is obtained from the infected subject, followed by exposing the culture to suitable culture conditions to allow for growth of the *S. aureus*, extracting nucleic acid from the cultured *S. aureus*, and then conducting at least one round of nucleic acid amplification using PCR or other suitable amplification protocol, using LukA and/or LukB-specific primers, and detecting LukA and/or LukB. Thus, in one representative embodiment, following initial sample preparation, the clinical isolate strains may be grown in grown on solid medium e.g., tryptic soy broth (TSB) solidified with 1.5% agar at 37° C. *S. aureus* colonies may then be selected and enzymatically digested, e.g., with 2 mg/ml lysostaphin (AMBI PRODUCTS LLC) in TSM buffer (100 mM TRIS pH7, 500 mM sucrose, 10 mM $MgCl_2$)] for 10 minutes at 37° C. Samples may then be centrifuged, the supernatant discarded, and the pellet resuspended with 100 μl sterile water, followed by boiling for five minutes at 100° C., and centrifugation The supernatant provides the starting material and the DNA template for an amplification reaction such as PCR using LukA and/or LukB-specific primers.

WORKING EXAMPLES

The invention will now be described by reference to the following non-limiting examples. Unless specified otherwise, all parts are by weight.

Example 1

Expression and Purification of Recombinant LukA and LukB Under Native Conditions: pMAL Expression System The LukA and LukB genes were amplified from *S. aureus* DNA with Taq polymerase under standard PCR settings with an annealing temperature of 55° C. using the following primers: 5'-ccc-GTCGAC-tta-TCCTTCTTTATAAGGTTT-ATTGTC-3' (SEQ ID NO:30) and 5'-ccc-GAAGGATTTCACATCATCATCATCATCACAATTCA-GCTCATAAAGACTCTC-3' (SEQ ID NO:31) for LukA and 5'-ccc-CGAAGGATTTCaCATCATCATCATCATCA-CAAGATTAATTCTGAAATCAAACAAG-3' (SEQ ID NO:32) and 5'-ccc-GTCGAC-tta-TTTCTTTTCATTAT-CATTAAGTACTT-3' (SEQ ID NO:33) for LukB. The LukA and LukB gene products were digested with Nde1 and Sal1 (New England BioLabs) and ligated into the pMAL-c4X vector (New England BioLabs). The constructs were transformed into the *E. coli* strain DH5α and the plasmid inserts were confirmed through sequencing. The transformants were grown in Terrific Broth with 100 ug/ml of ampicillin and 0.2% glucose at 37° C. until cultures reached an $A_{600}$ of ~0.5. The expression of 6-his-tagged MBP-LukA or 6-his-tagged MBP-LukB was induced with 0.3 mM isopropyl β-D-1-thiogalactopyranoside (IPTG) at 16° C., overnight, with 180 rpm shaking.

After the induction, the cells were harvested through centrifugation at 4000 rpm at 4° C. for 20 min and resuspended in ice cold Column Buffer (20 mM Tris-HCL, 200 mM NaCl, and 1 mM EDTA) supplemented with EDTA-free protease inhibitor (Roche). The bacterial cells were sonicated on ice for 1 min (10 sec pulses). The samples were centrifuged at 10,000 rpm at 4° C. for 30 min and the supernatant was collected and applied to an amylose resin column. The columns were washed two times with Column Buffer and purified 6-his-tagged MBP-LukA or 6-his-tagged MBP-LukB was eluted in 10 fractions with Column Buffer supplemented with 10 mM maltose.

Example 2

Expression and Purification of Recombinant Active LukA, LukAΔ10C, Δ33NLukA and LukB Toxins: pET14b Expression System The LukA, LukAΔ10C, Δ33NLukA and LukB genes were amplified from *S. aureus* DNA with Vent polymerase (New England BioLabs) under standard PCR settings with an annealing temperature of 55° C. using the following primers: 5'-cccc-CTCGAG-AATTCAGCTCATAAAGACTCT-CAAG-3' (SEQ ID NO:34) and 5'-cccc-GGATCC-tta-TC-CTTCTTTATAAGGTTTATTGTC-3' (SEQ ID NO:35) for LukA; 5'-cccc-CTCGAG-AATTCAGCT-CATAAAGACTCTCAAG (SEQ ID NO:34) and 5'-cccc-GGATCC-tta-ATATTTATCAACGACTTTAACTG (SEQ ID NO:36) for LukAΔ10C; 5'-cccc-CTCGAG-TCAACAG-CACCGGATGATATTG (SEQ ID NO:37) and 5'-cccc-GGATCC-tta-TCCTTCTTTATAAGGTTTATTGTC (SEQ ID NO:35) for Δ33NLukA; 5'-cccc-CTCGAG-AAGAT-TAATTCTGAAATCAAACAAG-3' (SEQ ID NO:38) and 5'-cccc-GGATCC-tta-TTTCTTTTCATTATCATTAAG-TACTTT-3' (SEQ ID NO:39) for LukB. The gene products were digested with Xho1 and BamH1 (New England Bio-Labs) and ligated into the pET14b vector (Novagen) fusing the coding sequence of a histidine-tag to the 5'-region of the genes. The expression plasmids were transformed into the *E. coli* strain DH5α and the plasmid inserts were confirmed through sequencing. The plasmids were purified and transformed into the expression *E. coli* strain T7 lysY/lq (New England BioLabs).

For purification under denaturing conditions the transformants were grown in Terrific Broth with 100 µg/ml of ampicillin at 37° C. until cultures reached an A600 of ~0.5. The expression of 6-his-tagged LukA or 6-hisLukB was induced with 0.4 mM IPTG at 37° C., for 3 hrs, with 180 rpm shaking. After the induction, the cells were harvested through centrifugation at 4000 rpm at 4° C. for 15 min and then resuspended in 1×TBS (50 mM Tris, 150 mM NaCl, pH 7.5). The bacterial cells were sonicated on ice for 2 min (10 sec pulses). The sonicated bacteria were ultracentrifuged for 30 min at 50,000 rpm. The pellets were resuspended in lysis buffer (100 mM NaH2PO4, 10 mM Tris, 8M urea, pH 8.0) and incubated at room temperature for 30 min on a rotisserie. The samples were centrifuged at 13,000 rpm for 30 min and the supernatants were applied to a column containing Ni-NTA resin (Qiagen). The column was washed two times with wash buffer (100 mM $NaH_2PO_4$, 10 mM Tris, 8M urea, pH 6.3) and the protein was eluted from the column using elution buffer (100 mM $NaH_2PO_4$, 10 mM Tris, 8M urea) at pH 5.9 and at pH 4.5. The fractions containing purified protein, as determined by SDSPAGE, were pooled, diluted 1:1 in tris buffered saline (TBS; 500 mM Tris, 1.5M NaCl, pH 7.5), and dialyzed in TBS at 4° C. overnight to remove the urea and allow refolding. Purified 6-his-tagged LukA and LukB were quantified using the Thermo Scientific Pierce BCA Protein Assay Kit.

For purification under native conditions the transformants were grown in Luria-Bertani broth with 100 µg/ml of ampicillin at 37° C. until cultures reached an A600 of ~0.5. The expression of 6-his-tagged LukA, 6-his-tagged LukAΔ10C, 6-his-tagged Δ33NLukA or 6-hisLukB was induced with 0.05-0.1 mM IPTG at 25-30° C., for 3 hrs, with 220 rpm shaking. After the induction, the cells were harvested through centrifugation at 4000 rpm at 4° C. for 15 min and then resuspended in 1×TBS (50 mM Tris, 600 mM NaCl, pH 7.5) with 10 mM imidazole and HALT EDTA-free protease inhibitor cocktail (Thermo Scientific). The bacterial cells were sonicated on ice. The sonicated bacteria were centrifuged for 20 min at 20,000 rpm. The supernatants were incubated with Ni-NTA resin (Qiagen) for 1 hr at 4° C. on a rotisserie. The samples were applied to a column and the column was washed with wash buffer 1×TES (50 mM Tris, 600 mM NaCl, pH 7.5) with 25 mM imidazole. The protein was eluted from the column using 50-500 mM imidazole in elution buffer 1×TBS (50 mM Tris, 600 mM NaCl, pH 7.5). The fractions containing purified protein, as determined by SDS-PAGE, were pooled, diluted 1:1 in 1×TBS (50 mM Tris, 150 mM NaCl, pH 7.5), and dialyzed in 1×TBS at 4° C. overnight. Purified 6-his-tagged LukA and LukB were quantified using the Thermo Scientific Pierce BCA Protein Assay Kit.

Example 3

Expression and Purification of Denatured Recombinant LukA and LukB

The LukA and LukB genes were amplified from *S. aureus* DNA with Vent polymerase (New England BioLabs) under standard PCR settings with an annealing temperature of 55° C. using the following primers: 5'-ggg-CATATG-AATTCA-GCTCATAAAGACTCTCAA-3' (SEQ ID NO:40) and 5'-ccc-GTCGAC-TCCTTCTTTATAAGGTTTATTGTC-3' (SEQ ID NO:41) for LukA and 5'-ggg-CATATG-AAGAT-TAATTCTGAAATCAAACAAG-3' (SEQ ID NO:42) and 5'-ccc-GTCGAC-TTTCTTTTCATTATCATTAAGTACTT-3' (SEQ ID NO:43) for LukB. The LukA and LukB gene products were digested with Nde1 and Sal1 (New England BioLabs) and ligated into the pET41b vector (Novagen). The constructs were first transformed into DH5α cells and then transformed into the *E. coli* expression strain ER2566 (New England BioLabs). The transformants were grown in Terrific Broth with kanamycin, 25 ug/ml, for 2.5 hrs at 37° C. and expression of LukA and LukB was induced with 0.3 mM IPTG at 37° C. for 2 hrs with 180 rpm shaking. The cells were pelleted and resuspended in 1×TBS (500 mM Tris, 1.5M NaCl, pH 7.5) and sonicated on ice for 1 min (10 sec pulses). The sonified bacteria were ultra-centrifuged for 30 min at 50,000 rpm.

In order to purify the C-terminal 6-his-tagged LukA and LukB under denaturing conditions, the pellets were resuspended in lysis buffer (100 mM $NaH_2PO_4$, 10 mM Tris, 8M urea, pH 8.0) and incubated at room temperature for 30 min on a rotisserie. The samples were centrifuged at 13,000 rpm for 30 min and the supernatants were applied to a Ni-NTA column. The columns were washed two times with wash buffer (100 mM $NaH_2PO_4$, 10 mM Tris, 8M urea, pH 6.3) and LukA and LukB were eluted from the columns using elution buffer (100 mM $NaH_2PO_4$, 10 mM Tris, 8M urea) at pH 5.9 and at pH 4.5. Purified 6-his-tagged LukA and LukB were quantified using the BioRad DC Protein Assay.

Example 4

Production of Anti-LukA and Anti-LukB Polyclonal Antibodies

Denatured-recombinant LukA (250 µg) emulsified in Freund's Complete Adjuvant (FCA) was injected into New Zealand White rabbits. Animals were boosted with recombinant LukA (125 µg) emulsified in Incomplete Freund's Adjuvant (FCA) at day twenty one (21) and at day forty-nine (49).

Denatured-recombinant LukB (250 µg) emulsified in Freund's Complete Adjuvant (FCA) was injected into New Zealand White rabbits. Animals were boosted with recombinant LukB (125 µg) emulsified in Incomplete Freund's Adjuvant (FCA) at day twenty one (21) and at day forty-nine (49).

Example 5

Leukocidin A/B is Predominantly Responsible for the Cytotoxin-mediated Killing of Human Phagocytes Through Membrane Disruption Cell Lines Used As a model to study how LukAB targets and kills human phagocytes HL-60 cells (ATCC CCL-240, a human promyelocytic cell line), were used. HL-60 cells were grown in RPMI medium (Gibco) supplemented with 10% of heat-inactivated fetal bovine serum (FBS) at 37° C. with 5% $CO_2$. To differentiate HL-60 into neutrophil-like cells (PMN-HL60), cultures were supplemented with 1.5% (v/v) dimethylsulfoxide (DMSO) and grown for 4 days.

Methods/Assays Used
Cell Toxicity Assay

To evaluate the viability of mammalian cells after intoxication with Staphylococcus aureus leukocidin AB (LukAB), PMN-HL60 cells were plated in 96-well flat-bottom tissue culture treated plates (Corning) at $1 \times 10^5$ cells/well in a final volume of 100 ul of RPMI (Gibco) supplemented with 10% of heat inactivated fetal bovine serum (FBS). Cells were intoxicated for 2 hrs at 37° C., 5% $CO_2$ with serial 2-fold dilutions of culture filtrate from Staphylococcus aureus strain Newman ranging from 20% to 0.16% v/v in triplicate. Experiments were performed using exoproteins from a wild-type strain and exoproteins from a strain lacking LukAB (mutant strain). Controls for 100% viability included 20% v/v tissue culture media (RPMI+10% heat-inactivated fetal bovine serum), and 20% v/v S. aureus growth media (RPMI+Cas amino acids). 0.1% v/v Triton X100 was used as a control for 100% cell death. After the intoxication, 10 μl of a dye suitable for monitoring cell viability was added to each well and the cells were incubated for an additional 3 hrs at 37° C., 5% $CO_2$. This dye monitors metabolically active cells (color change), a property lost in dead cells. The colorimetric reaction was measured at 492 nm using a Perkin Elmer Envision 2103 Multilabel Reader. Percent viable cells were calculated using the following equation: % Viability=$100 \times [(Ab_{492}Sample - Ab_{492}Triton \ X)/(Ab_{492}Tissue \ culture \ media)]$.

Membrane Damage Assay

An alternative assay to measure LukAB-mediated cytotoxicity is to evaluate the integrity of host cell membranes. To this end, a SYTOX green (Invitrogen) permeability assay was employed. Healthy cells are impermeable to SYTOX green, but become permeable to the dye once the cell membrane integrity has been compromised. Inside the cells, SYTOX green binds to DNA and exhibits strong fluorescence.

To evaluate the integrity of host cell membranes after intoxication with LukAB or ex vivo infection with S. aureus strains, PMN-HL60 cells were plated in 96-well flat-bottom tissue culture treated plates (Corning) at $1 \times 10^5$ cells/well in a final volume of 100 ul of RPMI (Gibco) supplemented with 10% of heat inactivated fetal bovine serum (FBS). Cells were either intoxicated with dilutions of culture filtrate from S. aureus strain Newman ranging from 20% to 0.16% v/v or infected with MOIs ranging from 1-100 in triplicate for 2 hrs at 37° C., 5% $CO_2$. Experiments were performed using a wild-type strain and a strain lacking LukAB (mutant strain). Controls for background fluorescence included 20% v/v tissue culture media (RPMI+10% heat-inactivated fetal bovine serum) and 20% v/v S. aureus growth media (RPMI+Cas Amino acids). After the intoxication or infection, the cells were transferred to 96-well v-bottom plate (Corning) and centrifuged at 1500 rpm for 5 min. The supernatant was discarded and the pellets were resuspended in 100 ul of PBS+SYTOX green (0.1 μM; Invitrogen). The cells were then transferred to 96-well clear-bottom black tissue culture treated plate (Corning) and incubated at room temperature in the dark for 10 min. Fluorescence was measured using a Perkin Elmer Envision 2103 Multilabel Reader (Excitation 485 nm, Emission 535 nm).

Results
LukAB Targets and Kills Human Primary Phagocytes

Intoxication of primary human peripheral mononuclear cells (PBMCs) (FIG. 3a), monocytes, macrophages, dendritic cells (FIG. 3b) and polymorphonuclear cells (PMNs) (FIG. 3c) with filtered culture supernatants from the S. aureus strain Newman resulted in potent cell death as examined by the Cell Toxicity Assay (FIGS. 3a-c). Intoxication of these cells with filtered culture supernatants from the S. aureus strain Newman lacking-hemolysin (hla), γ-hemolysin (hlg), leukocidin E/D (LukED) or leukocidin A/B (LukAB) revealed that exoproteins from hla-, hlg-, and LukED-negative strains are as cytotoxic as the Newman wildtype (WT) strain (as examined by the cell toxicity assay), indicating none of the previously-described leukotoxins produced by Newman contributes to the cytotoxin-mediated killing of these cells (FIGS. 3a-c). In contrast, very little cell death was observed when cells were intoxicated with exoproteins from the strain Newman lacking LukAB (ΔlukAB). The lack of cytotoxic activity by the strain Newman lacking LukAB was rescued by providing the lukAB genes in trans in a plasmid (ΔlukAB/pLukAB) (FIG. 3c). Importantly, this phenotype is fully dependent on LukAB as determined by intoxicating PMNs with purified-recombinant LukA and LukB. Individual subunits exhibited no detectable cytotoxicity towards PMNs (FIG. 3d). In contrast, combination of both subunits resulted in potent cytotoxicity towards these cells in a dose-dependent manner (FIG. 3d). Altogether, these results demonstrate LukAB is responsible for the ability of S. aureus to target and kill primary human phagocytes, key immune cells required for protecting the host against infectious agents.

LukAB Preferentially Kills Human Phagocytic Cells

Figure 4:
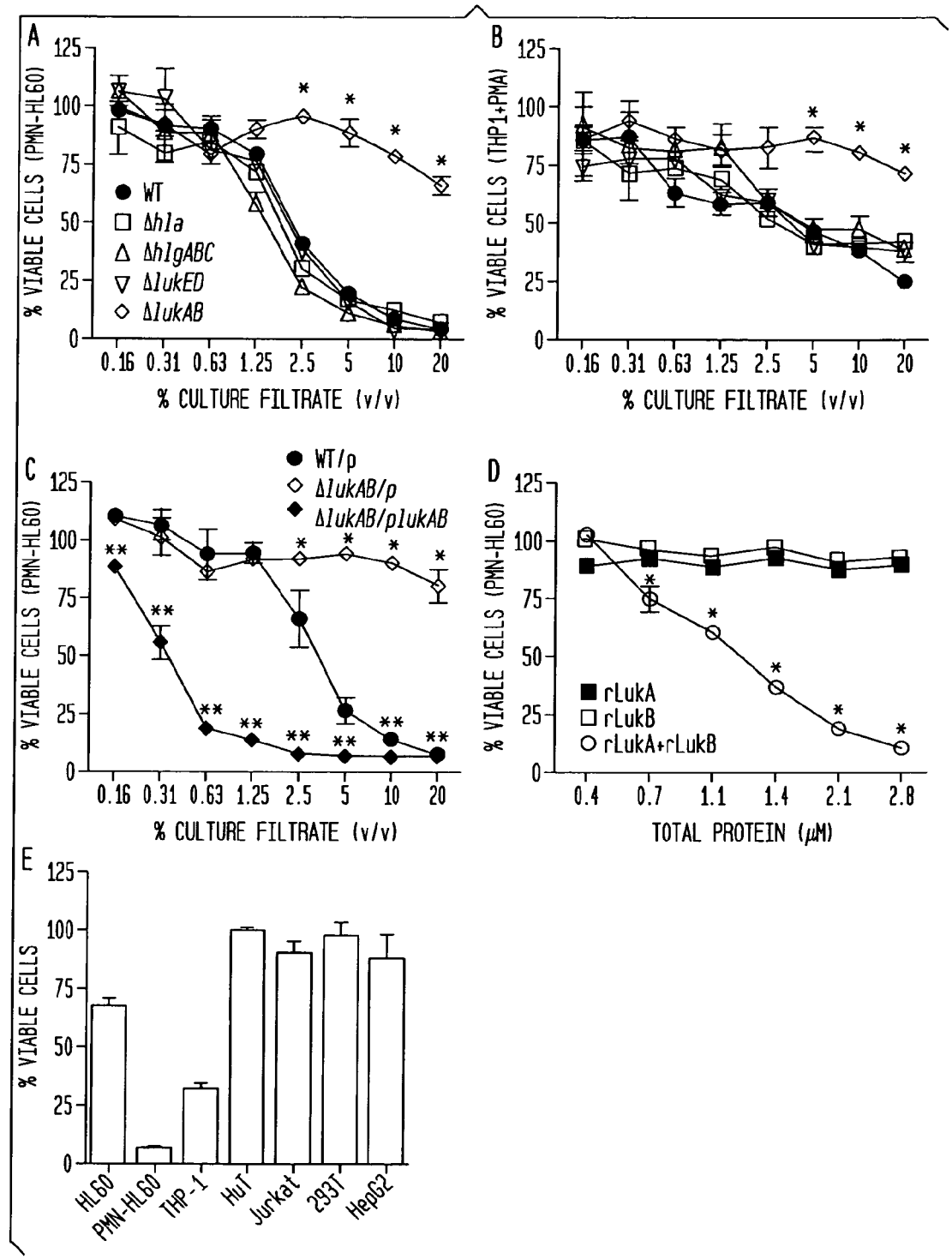
FIG. 4. LukAB preferentially targets human phagocytic cells. Intoxication of (a, c and d) PMN-HL60 or (b) THP1 cells with various dilutions of culture filtrate from the S. aureus WT strain Newman, isogenic mutant strains lacking the indicated genes/toxins, (c) culture filtrate from S. aureus WT containing an empty plasmid (WT/p),a strain lacking LukAB with and empty plasmid (ΔLukAB/p), and a strain lacking LukAB with a LukAB complementation plasmid (ΔLukAB/pLukAB), or (d) with purified recombinant LukA (rLukA), LukB (rLukB), or a combination of rLukA and rLukB (rLukA+rLukB) at the indicated concentrations. For the intoxications with both rLukA and rLukB, the total protein concentration is comprised of equal amounts of rLukA and rLukB(e.g. 2.8 μg total protein is equal to 1.4 μg of rLukA and 1.4 μg of rLukB). (e) Intoxication of the indicated human cell lines with 10 μg/ml of rLukAB. Cell viability was monitored using a commercially available cell viability assay, where cells treated with medium were set at 100%. Results represent the average of triplicate samples ±S.D. Asterisk (*) denote statistically significant difference compared to WT (One-way ANOVA).

Intoxication of the neutrophil-like cell line (PMN-HL60) and the macrophage-like cell line (THP1+PMA) with filtered culture supernatants from the S. aureus strain Newman resulted in potent cell death as examined by the Cell Toxicity Assay (FIG. 3). Intoxication of these cells with filtered culture supernatants from the S. aureus WT and the isogenic cytotoxin mutant strains (hla, hlgABC, LukED, and LukAB) revealed that that LukAB is responsible for the ability of S. aureus to kill these cells as determined by the cell toxicity assay (FIGS. 4a and 4b). The lack of cytotoxic activity by the strain Newman lacking LukAB was rescued by transforming the strain Newman lacking LukAB with a plasmid expressing lukAB (ΔlukAB/pLukAB) (FIG. 4c). Exoproteins from this strain were extremely cytotoxic to both PMN-HL60 cells and THP-1+PMA cells, providing strong evidence that LukAB is a potent staphylococcal toxin that targets and kills human cells.

To further rule out the contribution of other factors present in S. aureus culture supernatant, PMN-HL60 cells were intoxicated with purified-recombinant LukA or LukB. Individual subunits exhibited no detectable cytotoxicity towards PMN-HL60 (FIG. 3d). In contrast, combination of both subunits resulted in potent cytotoxicity towards these cells in a dose-dependent manner (FIG. 3d). In addition to PMN-HL60s and THP-1+PMA cells, several other human cell lines including the myeloid progenitor that PMN-HL60s are differentiated from (HL60), the monocyte progenitor that THP-1+PMA are differentiated from (THP-1), lymphocytes (HuT and Jurkat cells), and epithelial cells (293T and HepG2) were also intoxicated with recombinant LukAB (FIG. 4e). These results demonstrate that LukAB preferentially targets and kills human phagocytic cells and has no effect on human lymphocytes or epithelial cells. Together these results demonstrate that LukAB plays a significant role in S. aureus-mediated killing of phagocytes.

LukAB is Produced by Clinical Relevant Strains of *S. aureus*

Figure 5:
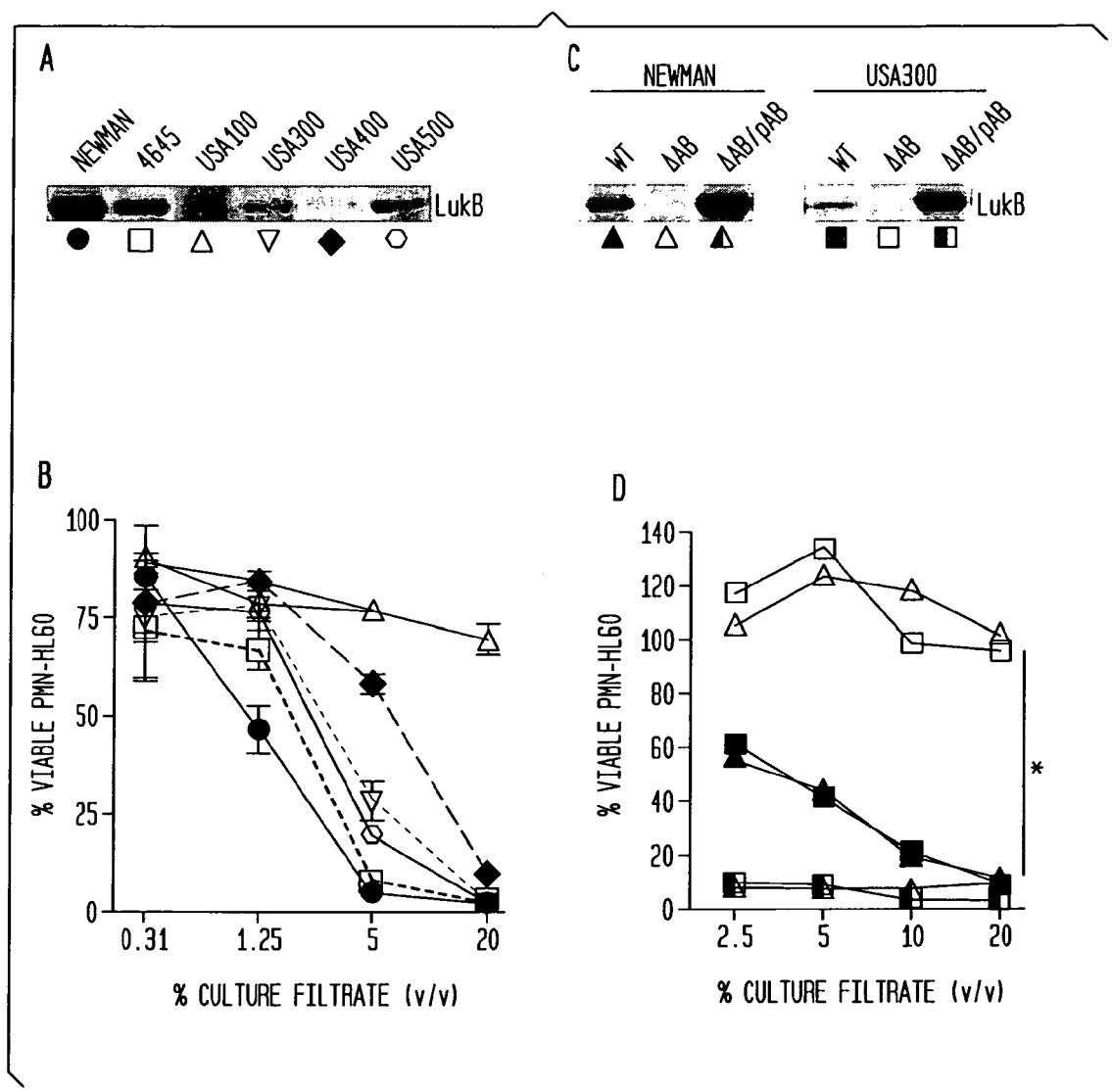
FIG. 5. LukAB is an important toxin in different staphylococcal strains. (A) Expression of LukB by various S. aureus strains as determined by Western blot analysis using an anti-LukB polyclonal sera. (B) Intoxication of PMN-HL60 with dilutions of exoproteins from different S. aureus strains. Cell viability was monitored using a commercially available cell viability assay, where cells treated with medium were set at 100% viable. (C) Expression of LukB and α-toxin by WT and LukAB isogenic strains as determined by Western blot analysis using toxin-specific sera. (D) Intoxication of PMN-HL60 with exoproteins from WT strains Newman (New.) and 4645, and the LukAB isogenic strains. Cell viability was monitored as in Panel B. Results represent the average of triplicate samples +S.D. * denote statistically significant difference compared to Newman (C) or to WT (E) (Student's t test $p<0.05$).

Immunoblot analyses with a polyclonal antibody raised against LukB revealed that LukB is produced by a series of staphylococcal strains including MRSA strains associated with hospital- and community-acquired infections (USA300, 400, and 500; FIG. 5a). Importantly, LukB levels are associated with the cytotoxic phenotype of these strains (FIGS. 5a and 5b). Strains that produce high levels of LukB (e.g., Newman, 4645, USA 500, and USA 300) were more cytotoxic towards PMN-HL60 cells than strains that produce low or undetectable LukB (e.g., USA100 and USA400) (FIG. 5b). To investigate the role of LukAB in MRSA strains, a LukAB isogenic mutant was created in the clinical isolate USA type 300 LA clone (FIG. 5c). As seen with strain Newman, exoproteins from strain USA300 lacking LukAB were noticeably less cytotoxic than exoproteins from the parental strain (FIG. 5d). These data demonstrate that LukAB is an important cytotoxin produced by MRSA strains.

LukAB Damages the Membranes of Human Phagocytes

Figure 6:
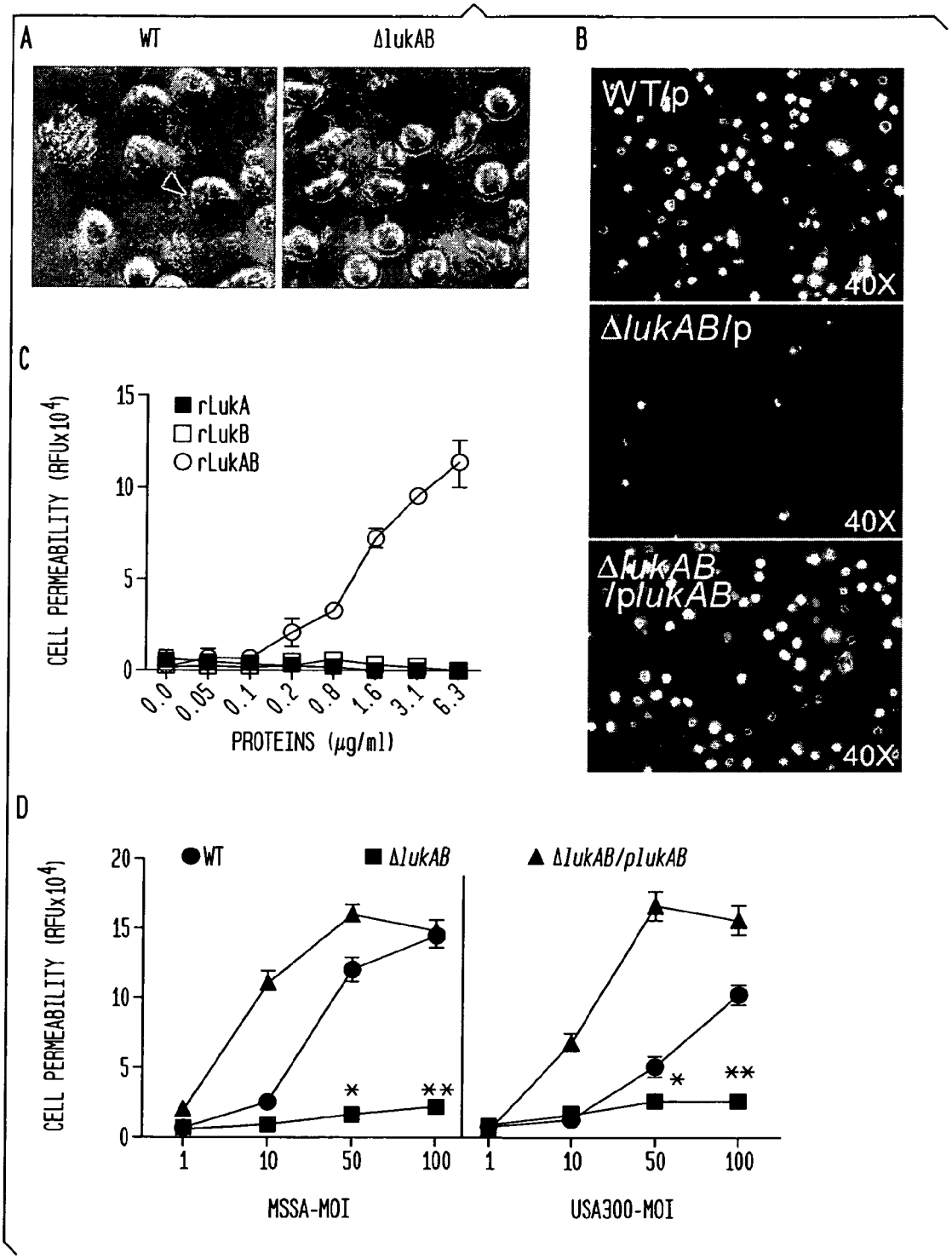
FIG. 6. LukAB disrupts the plasma membranes of target cells. (a) Light microscopy images of PMN-HL60 cells intoxicated with culture filtrate from the S. aureus WT strain and the isogenic strain lacking LukAB (ΔLukAB). (b-c) Intoxication of PMN-HL60 cells with culture filtrates from the WT strain (WT/p), the isogenic strain lacking LukAB (ΔLukAB/p), the complemented strain (ΔLukAB/pLukAB), or mock intoxicated with medium. Cells with compromised membranes were stained with SYTOX Green, imaged by fluorescence microscopy (c), and green-fluorescence intensity was measured (b). (d) PMNs were infected ex vivo with S. aureus strain Newman (MSSA) or USA300 strain LAC (MRSA) and the indicated isogenic mutants at various multiplicities of infection (MOI). Membrane damage was monitored with SYTOX green. Results represent the average of triplicate samples±S.D. Asterisks (*) denote statistically significant difference compared to WT (Student's t test $p<0.05$).

Intoxication of PMN-HL60 with exoproteins from *S. aureus* resulted in cell rounding and nuclear swelling, a phenotype dependent on LukAB (FIG. 6a). This cell rounding and swelling phenotype was associated with increased membrane permeability as determined by the Membrane Damage Assay (FIGS. 6b and 6c). Importantly, exoproteins from the LukAB-negative strain exhibited little to no effect on membrane permeability, a phenotype that was rescued by producing LukAB from a plasmid (FIG. 6b) and recombinant LukAB but the not the individual toxin subunits cause membrane damage in a dose-dependent manner (FIG. 6c). Furthermore, infection of primary human PMNs with both a methicillin-sensitive *S. aureus* (MSSA) strain and a methicillin-resistant *S. aureus* (MRSA) USA300 strain resulted in LukAB-dependent membrane damage (FIG. 6d). These results demonstrate that LukAB damages the plasma membrane of host cells during ex vivo infection.

LukAB protects *S. aureus* from host-mediated killing, by targeting and killing phagocytes.

Figure 7:
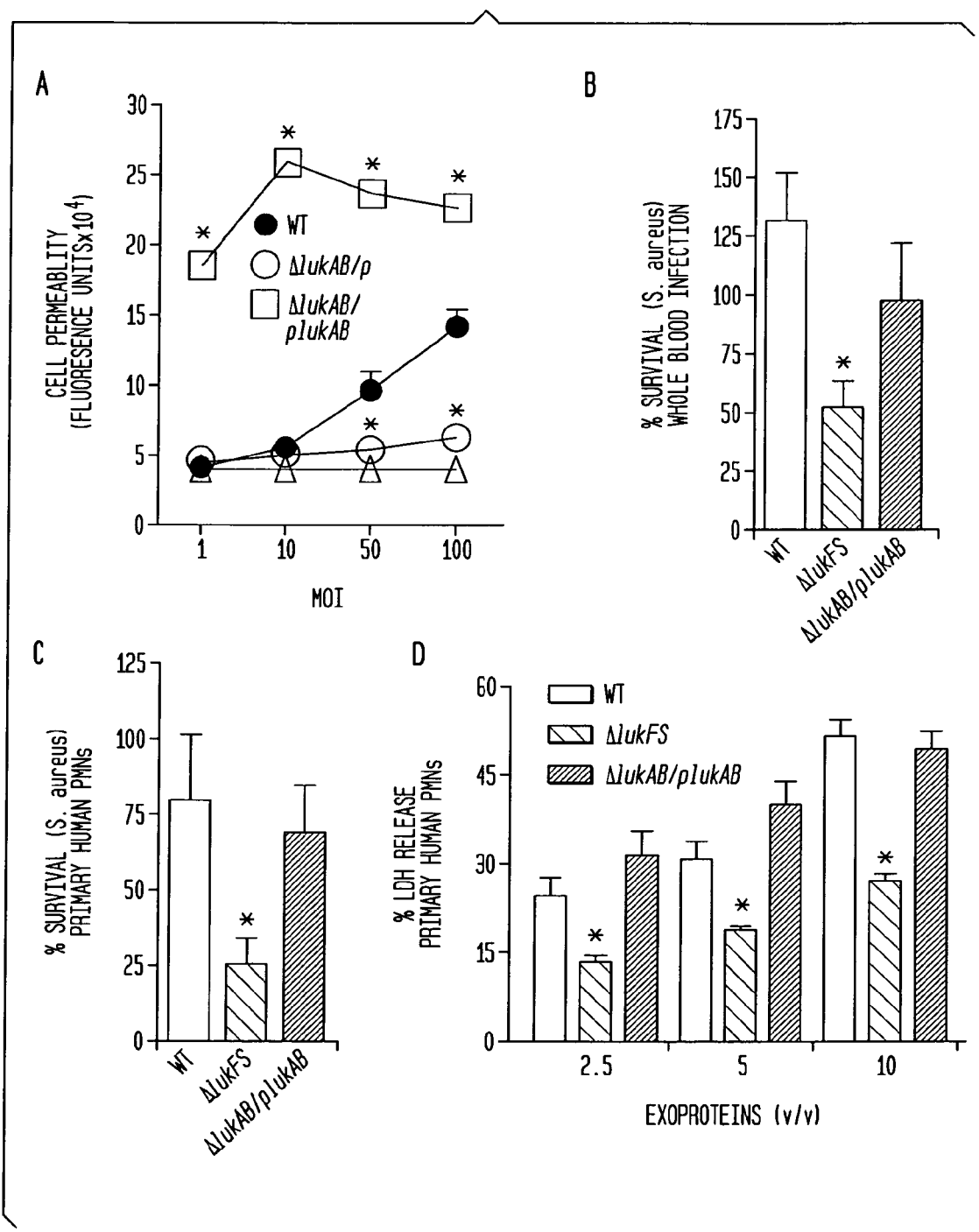
FIG. 7. LukAB protects S. aureus from host-mediated killing by targeting and killing phagocytes. (a) Infection of PMN-HL60 cells with S. aureus WT, a strain lacking lukAB, and the strain lacking lukAB with a lukAB complementation plasmid (ΔlukAB/plukAB) at various multiplicities of infection (MOI). Mammalian cells with compromised membranes were monitored with SYTOX Green as described in FIG. 6. Results represent the average of triplicate samples+ S.D. (b) Viability of the indicated S. aureus strains upon ex vivo infection of human whole blood. Results represent the mean from whole blood isolated from 12 donors+S.E.M. (c) Viability of the indicated S. aureus Newman strains upon infection of primary human neutrophils (PMNs). Results represent the mean from PMNs isolated from 12 donors+ S.E.M. (d) Intoxication of primary human PMNs with various dilutions of culture filtrate from the WT/p, ΔlukAB/ p, and ΔlukAB/plukAB strains. LDH-release was measured as an indicator of cell lysis. Results represent the mean from PMNs isolated from 6 donors+S.E.M. Asterisks (*) denote statistically significant difference compared to WT strain Newman (Student's t test $p<0.05$).

Infection of PMN-HL60 cells with *S. aureus* WT, ΔlukAB and the ΔlukAB harboring the lukAB expression plasmid (ΔlukAB/plukAB) revealed that LukAB is required for the ability of *S. aureus* to disrupt the membrane of phagocytes during *staph*-phagocyte interaction (FIG. 7a), as determined by the Membrane Damage Assay. Importantly, *S. aureus* overproducing LukAB (ΔlukAB/plukAB) exhibited more membrane damage than the WT strain (FIG. 7a) demonstrating that LukAB potently damages host cell membranes. Infection of human whole blood (FIG. 7b) and purified primary human neutrophils (PMN; FIG. 7c) revealed that lukAB-negative *staph* was killed more efficiently compared to the WT strain (FIGS. 7b and 7c). Importantly, the attenuated phenotype exhibited by the ΔlukAB-negative *staph* was rescued with the lukAB expression plasmid (FIGS. 7b and 7c). Intoxication of primary human PMNs with culture filtrate of *S. aureus* WT, ΔlukAB, and the ΔlukAB mutant strain containing the lukAB expression plasmid revealed that LukAB targets and kills primary human PMNs (FIG. 7d). These data strongly indicate that LukAB is a potent staphylococcal cytotoxin that targets and kills PMNs through membrane disruption thus protecting *S. aureus* from PMN-mediated killing.

LukAB Contributes to the Pathogenesis of *S. aureus* In Vivo

Figure 8:
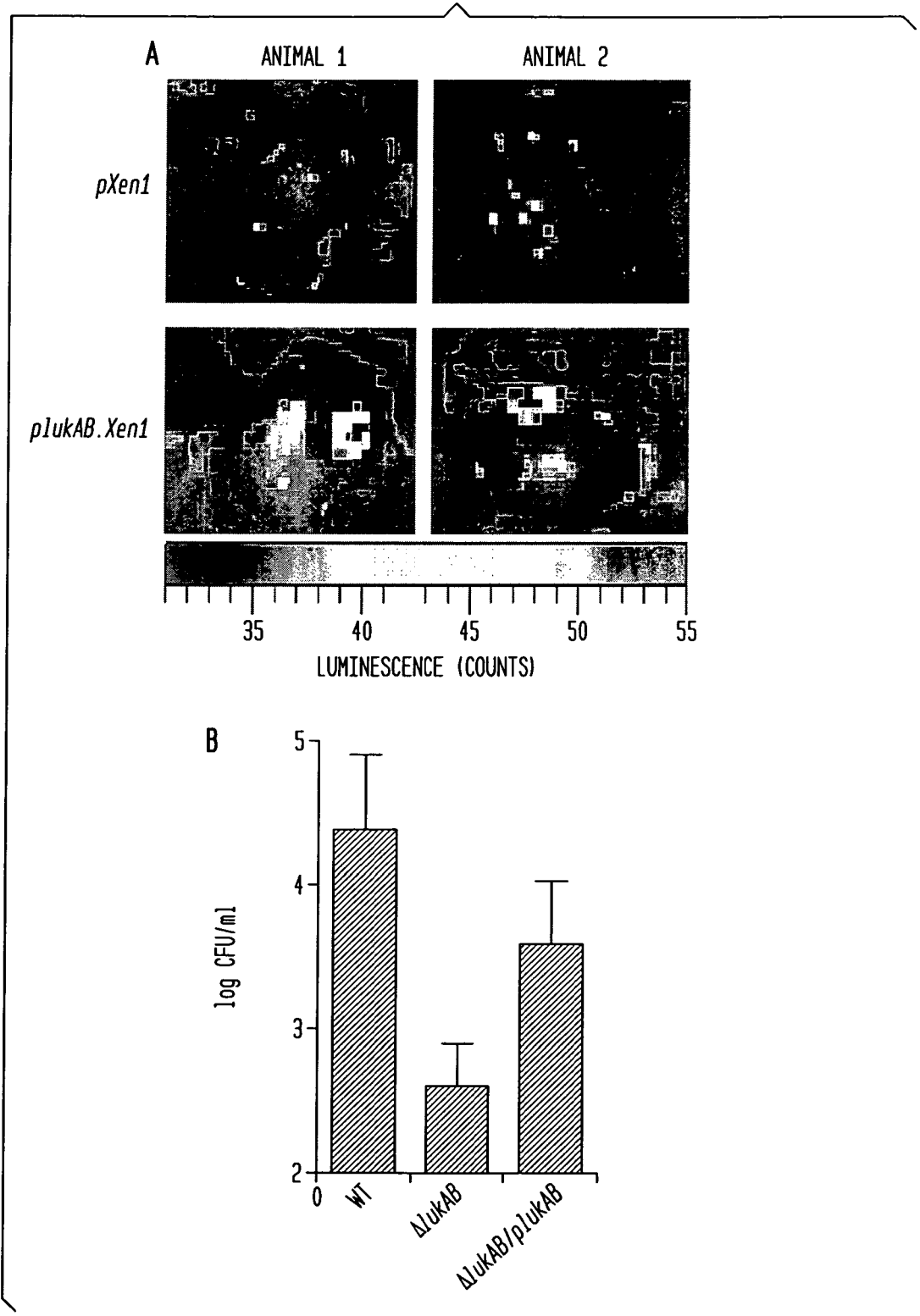
FIG. 8. LukAB is important for the pathogenesis of S. aureus in vivo. (a) Bioluminescent images of kidneys from mice infected with the WT S. aureus strain LAC containing pXen1 or the pLukAB.Xen1. The kidneys of two representative mice per group are shown. (b) Bacterial load recovered from the kidneys of mice infected retro-orbitally with the indicated S. aureus LAC strains. Each data point represents the number of bacteria (CFU) per milliliter of tissue homogenate in a single animal. Dashed line indicates the limit of detection. For panels (A-C and E) * indicates statistical significance from WT, ** indicates statistical significance from ΔLukAB/p, $P<0.05$.

Mice infected retro-orbitally with *S. aureus* containing a luciferase reporter construct with the LukAB promoter fused to it (pLukAB-Xen1) showed LukAB promoter activity in kidney abscesses, where as a promoterless reporter (pXen1) showed no activity (FIG. 8a). These data demonstrate that LukAB is expressed in vivo in a renal abscess model of infection. In addition, mice infected retro-orbitally with *S. aureus* WT but not a *S. aureus* strain lacking LukAB displayed extensive colonization of the kidneys. The colonization defect observed in the LukAB-negative strain was restored to WT levels by providing LukAB in trans (FIG. 8b). Together these data show that LukAB is an important staphylococcal cytotoxin that contributes to the pathogenesis of the bacterium.

Figure 9:
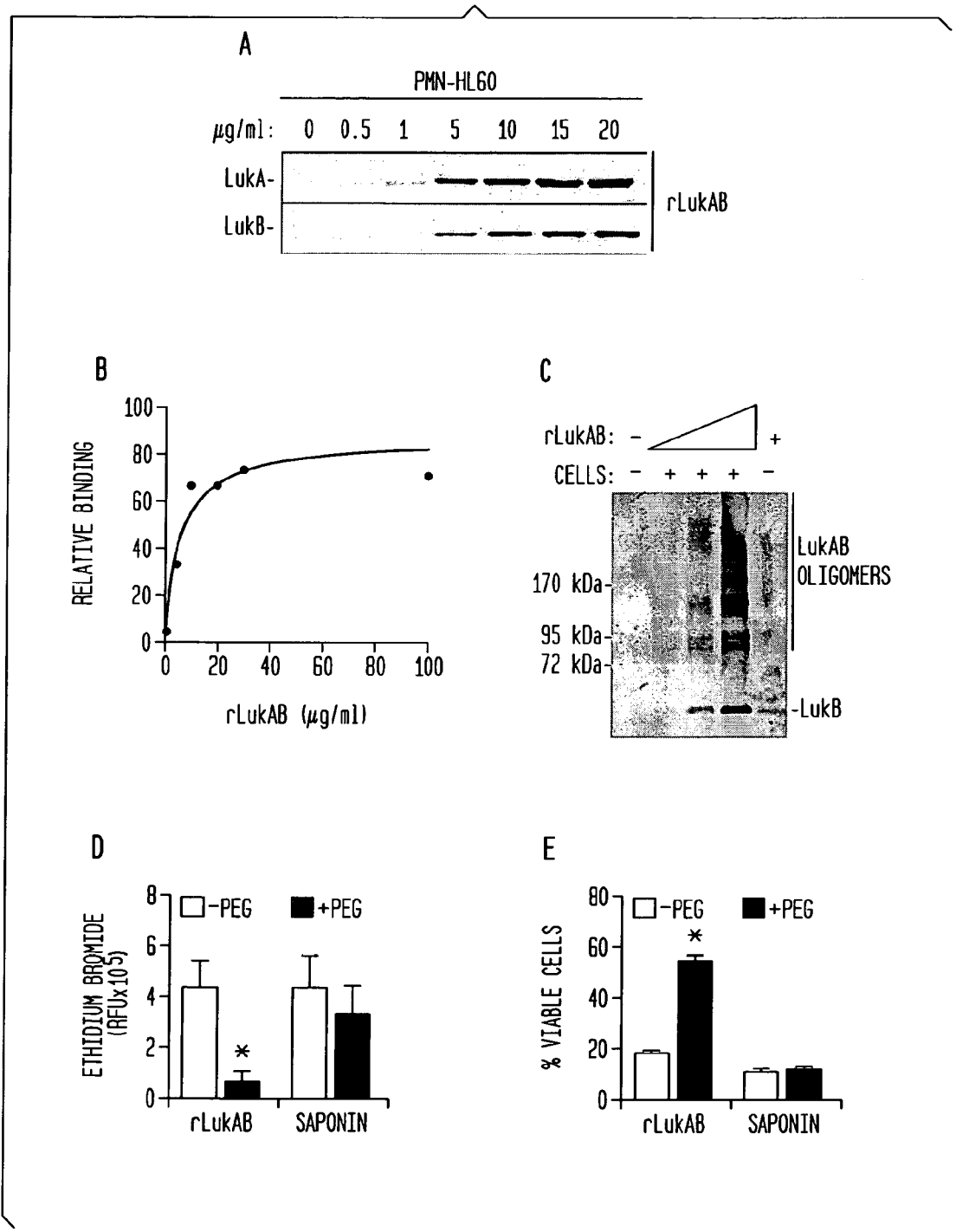
FIG. 9. LukAB kills human phagocytes by forming pores on cell membranes. (a) PMN-HL60 cells were intoxicated with rLukA+rLukB and toxin binding was monitored by SDS-PAGE and immunoblotting using antibodies specific for LukA or LukB. (b) PMN-HL60were incubated with rLukAB and toxin binding determined by FACS using a rabbit anti-His antibody. (c) PMN-HL60 cells were intoxicated with rLukAB and the formation of LukAB oligomers in the plasma membrane was determined by SDS-PAGE and immunoblotting using an anti-LukB antibody. (d) PMN-HL60 intoxicated with rLukAB or treated with saponin in the presence or absence of PEG-400. LukAB pores were detected with ethidium bromide. (e) Viability of PMN-HL60 treated as in panel determined with a commercially available cell viability assay, where cells treated with medium were set at 100%. Results in panels d and e represent the average of triplicate samples +/ SEM. * denote statistically significant difference to —PEGs (panel d-e) (Student's t test $p<0.05$).

LukAB Forms Pores on the Target Cell Membrane that can be Blocked with Polyethylene Glycol Intoxication of PMN-HL60 cells with recombinant LukAB (rLukAB) revealed that both rLukA and rLukB bind to target cells as determined via immunoblot with LukA and LukB specific antibodies (FIG. 9a). Binding of 6His-tagged rLukAB to PMN-HL60s was also confirmed using fluorescence-activated cell sorting (FACS) and a His specific antibody (FIG. 9b). rLukAB oligomers were also detected via immunoblot on PMN-HL60 membranes after intoxication with the recombinant toxin indicating that LukAB forms higher order structures on target-cell membranes (FIG. 9c). Importantly, intoxication of PMN-HL60s with rLukAB demonstrated that LukAB forms ethidium bromide permeable pores on target-cell membranes that can be blocked using polyethylene glycol molecules (PEG) (FIG. 9d), and that blocking the LukAB pores increases viability of the cells (FIG. 9e). Furthermore, the PEGs specifically block LukAB pores, as pores formed in PMN-HL60 membranes by saponin were not blocked by the PEGs and as a result these cells were not protected from pore-mediated death. These data demonstrate that LukAB pores can be blocked by small molecules and blocking LukAB pores protects cells from LukAB-mediated killing.

Neutralization of *S. aureus* Culture Filtrate Cytotoxicity with an α-LukA Polyclonal Antibody.

Figure 10:
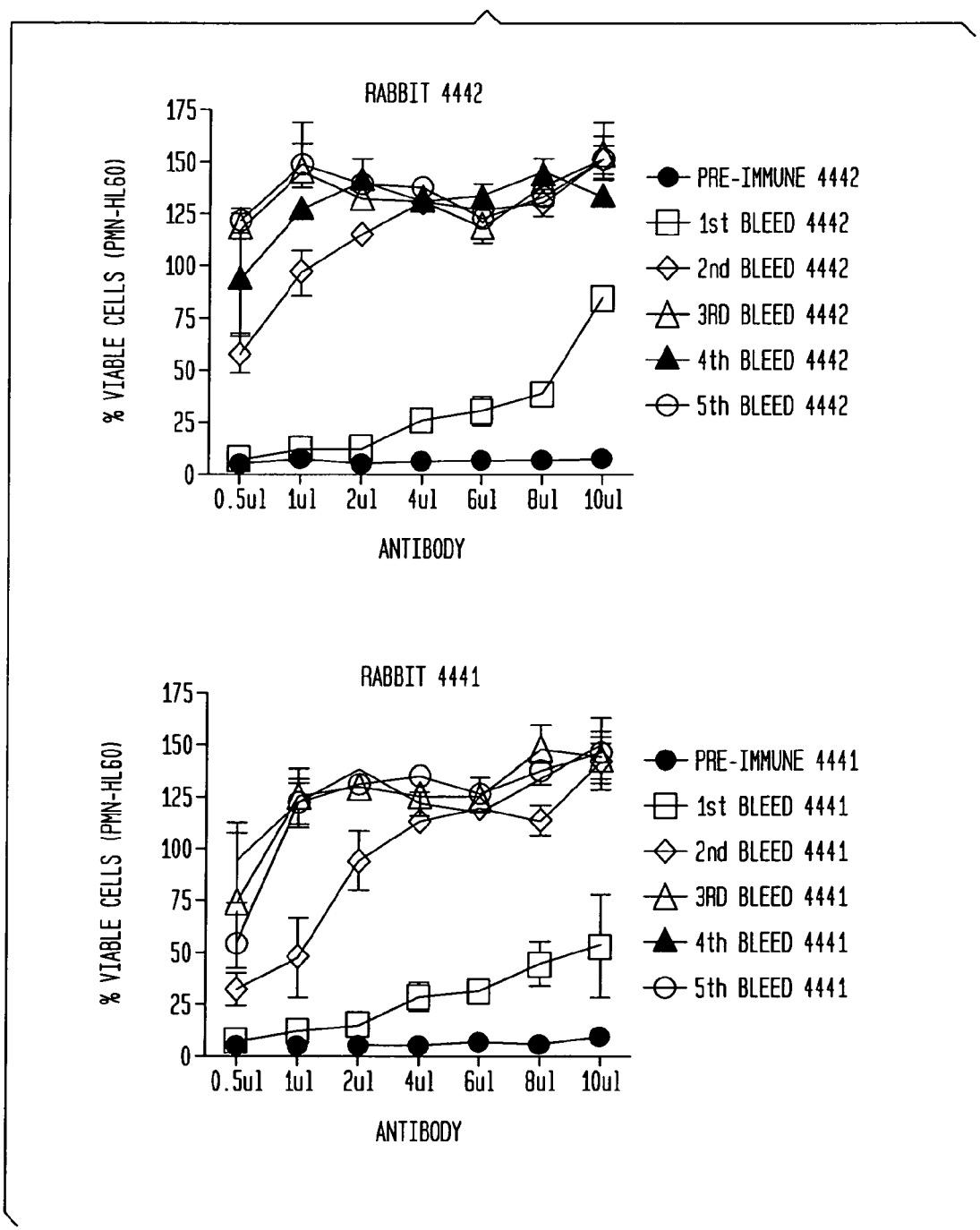
FIG. 10. LukAB cytotoxicity can be neutralized by an α-LukA polyclonal antibody. Intoxication of PMN-HL60s with 5% (v/v) culture filtrate from S. aureus strain Newman that had been incubated with the indicated amounts of α-LukA polyclonal antibodies or pre-immune serum from various production bleeds from two different rabbits. Cell viability was monitored using a commercially available cell viability assay, where cells treated with medium were set at 100%. Results represent the average of triplicate samples ±standard deviation (S.D.).

Intoxication of PMN-HL60s with *S. aureus* culture filtrate pre-incubated with various amounts of α-LukA polyclonal antibodies generated in two different rabbits resulted in decreased toxicity of the culture filtrate in a dose-dependent manner (FIG. 10). This neutralizing effect was not seen when culture filtrate was pre-incubated with pre-immune serum. Importantly, antibodies generated in the two different rabbits behaved very similar, and the neutralization capabilities of the antibodies increased with maturity as seen by comparing the neutralizing effect of antibody from the late bleeds to the neutralizing effect of antibody from the early bleeds (FIG. 10). These data show that cytotoxicity seen with culture filtrate from *S. aureus* can be neutralized with α-LukA polyclonal antibodies.

Identification of a Non-cytotoxic LukA Truncation Mutant that is Still Recognized by the α-LukA Polyclonal Antibody.

Figure 11B:
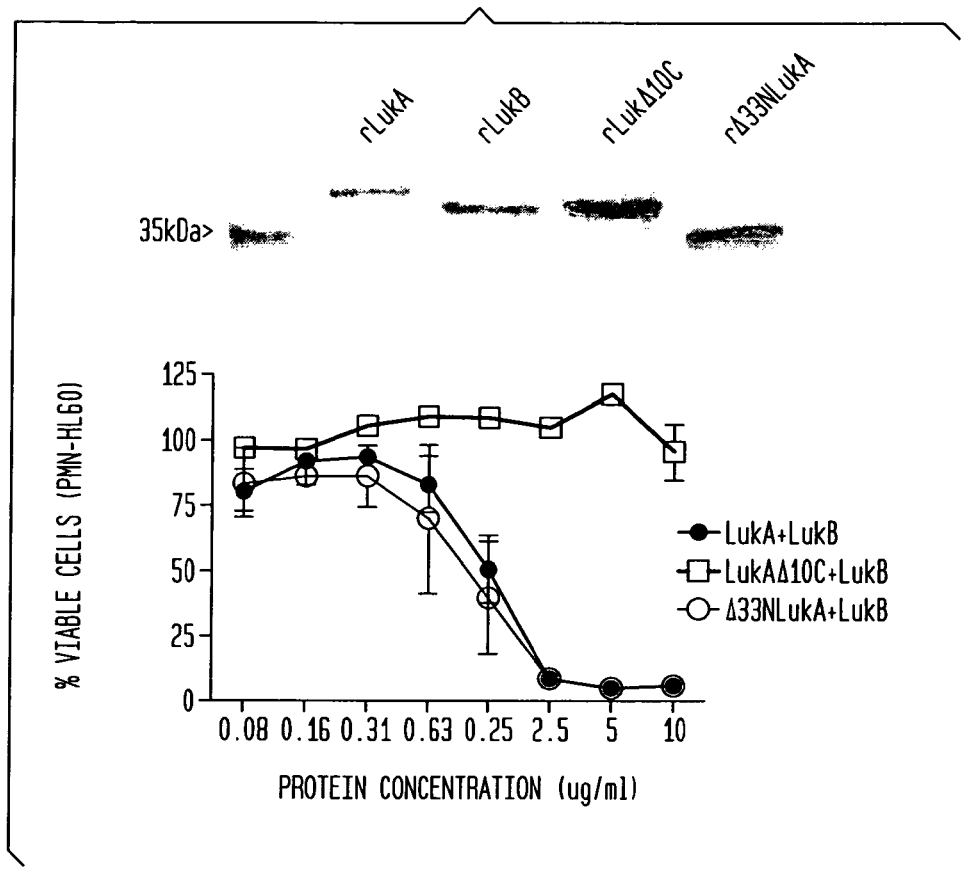
FIG. 11. The LukA C-terminal extension is necessary for the cytotoxic effect of LukAB but is not needed for recognition by an α-LukA polyclonal antibody. (a) Alignment of amino acid sequences from the various *S. aureus* leukotoxin S-subunits (designated as SEQ ID NOS:44-49) performed using the MegAlign Clustal W method from Lasergene software. The N- and C-terminal extensions only present in the LukA sequence are emphasized with boxes. (b) Coomassie blue staining of 2 μg of recombinant LukA (rLukA), LukB (rLukB), LukA lacking the C-terminal extension (rLukAΔ10C) and LukA lacking the N-terminal extension (rΔ33NLukA) purified from *E. coli* and separated by SDS-PAGE accompanied by intoxication of PMN-HL60s with various amounts of rLukA, rLukAΔ10C and rΔ33NLukA paired with rLukB. The final protein concentration represents equal amounts of rLukA, rLukAΔ10C or rΔ33NLukA and rLukB. Results represent the average of triplicate samples±S.D. (c) Immunoblot showing equivalent recognition of 6×His-tagged rLukAΔ10C by both α-LukA and α-His polyclonal antibodies.
Figure 11C:
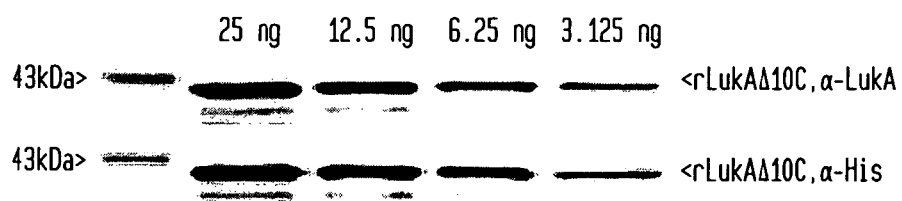

LukA differs from the other staphylococcal leukotoxin S-subunits in that it has an extension at both the N- and C-terminus. This extension consists of 33 amino acids at the N-terminus and 10 amino acids at the C-terminus (FIG. 11a). Intoxication of PMN-HL60s with purified recombinant LukA lacking the N-terminus extension (rΔ33NLukA) in combination with purified rLukB resulted in potent cytotoxicity towards the cells comparable to that of purified rLukA+ rLukB (FIG. 11b). However, intoxication of PMN-HL60s with purified recombinant LukA lacking the C-terminal extension (rLukAΔ10C) in combination with rLukB resulted in no cytotoxic effect (FIG. 11b). These data demonstrate that the N-terminal extension is dispensable for the cytotoxic effect of LukA but the C-terminal extension is necessary for toxicity. Importantly, the α-LukA polyclonal antibody that neutralizes the effect of LukAB (FIG. 10) still recognizes the 6×His-tagged non-cytotoxic rLukAΔ10C mutant just as well as the α-His polyclonal antibody (FIG. 11c). These data suggest that rLukAΔ10C may be exploited to generate α-LukA polyclonal antibodies in vivo that are neutralizing antibodies. Therefore, rLukAΔ10C may be used in an active vaccine composition.

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A composition comprising:

a LukA polypeptide analog, wherein said analog comprises the amino acid sequence of amino acid residues 28-341 of SEQ ID NO: 2, and does not comprise the amino acid sequence of amino acid residues 342-351 of SEQ ID NO: 2, wherein said LukA polypeptide analog is non-cytotoxic when combined with a LukB polypeptide comprising the amino acid sequence of amino acid residues 30-339 of SEQ ID NO: 27.

2. The composition of claim 1 further comprising a LukB polypeptide comprising the amino acid sequence of amino acid residues 30-339 of SEQ ID NO: 27.

3. The composition of claim 1 further comprising a pharmaceutically acceptable carrier.

* * * * *

SEQUENCE LISTING

```
<160> NUMBER OF SEQ ID NOS: 49

<210> SEQ ID NO 1
<211> LENGTH: 351
<212> TYPE: PRT
<213> ORGANISM: Staphylococcus aureus
<220> FEATURE:
<221> NAME/KEY: MISC_FEATURE
<222> LOCATION: (63)..(63)
<223> OTHER INFORMATION: Xaa can be any naturally occurring amino acid
<220> FEATURE:
<221> NAME/KEY: MISC_FEATURE
<222> LOCATION: (342)..(351)
<223> OTHER INFORMATION: Amino acids corresponding to these residues may
      be lacking/deleted.

<400> SEQUENCE: 1

Met Lys Asn Lys Lys Arg Val Leu Ile Ala Ser Ser Leu Ser Cys Ala
1               5                   10                  15

Ile Leu Leu Leu Ser Ala Ala Thr Thr Gln Ala Asn Ser Ala His Lys
            20                  25                  30

Asp Ser Gln Asp Gln Asn Lys Lys Glu His Val Asp Lys Ser Gln Gln
        35                  40                  45

Lys Glu Lys Arg Asn Val Thr Asn Lys Asp Lys Asn Ser Thr Xaa Pro
    50                  55                  60

Asp Asp Ile Gly Lys Asn Gly Lys Ile Thr Lys Arg Thr Glu Thr Val
65                  70                  75                  80

Tyr Asp Glu Lys Thr Asn Ile Leu Gln Asn Leu Gln Phe Asp Phe Ile
                85                  90                  95

Asp Asp Pro Thr Tyr Asp Lys Asn Val Leu Leu Val Lys Lys Gln Gly
            100                 105                 110

Ser Ile His Ser Asn Leu Lys Phe Glu Ser His Lys Glu Glu Lys Asn
        115                 120                 125

Ser Asn Trp Leu Lys Tyr Pro Ser Glu Tyr His Val Asp Phe Gln Val
    130                 135                 140

Lys Arg Asn Arg Lys Thr Glu Ile Leu Asp Gln Leu Pro Lys Asn Lys
145                 150                 155                 160

Ile Ser Thr Ala Lys Val Asp Ser Thr Phe Ser Tyr Ser Ser Gly Gly
                165                 170                 175

Lys Phe Asp Ser Thr Lys Gly Ile Gly Arg Thr Ser Ser Asn Ser Tyr
            180                 185                 190

Ser Lys Thr Ile Ser Tyr Asn Gln Gln Asn Tyr Asp Thr Ile Ala Ser
        195                 200                 205

Gly Lys Asn Asn Asn Trp His Val His Trp Ser Val Ile Ala Asn Asp
    210                 215                 220

Leu Lys Tyr Gly Gly Glu Val Lys Asn Arg Asn Asp Glu Leu Leu Phe
225                 230                 235                 240
```

```
Tyr Arg Asn Thr Arg Ile Ala Thr Val Glu Asn Pro Glu Leu Ser Phe
                245                 250                 255

Ala Ser Lys Tyr Arg Tyr Pro Ala Leu Val Arg Ser Gly Phe Asn Pro
            260                 265                 270

Glu Phe Leu Thr Tyr Leu Ser Asn Glu Lys Ser Asn Glu Lys Thr Gln
        275                 280                 285

Phe Glu Val Thr Tyr Thr Arg Asn Gln Asp Ile Leu Lys Asn Arg Pro
    290                 295                 300

Gly Ile His Tyr Ala Pro Pro Ile Leu Glu Lys Asn Lys Asp Gly Gln
305                 310                 315                 320

Arg Leu Ile Val Thr Tyr Glu Val Asp Trp Lys Asn Lys Thr Val Lys
                325                 330                 335

Val Val Asp Lys Tyr Ser Asp Asp Asn Lys Pro Tyr Lys Glu Gly
                340                 345                 350

<210> SEQ ID NO 2
<211> LENGTH: 351
<212> TYPE: PRT
<213> ORGANISM: Staphylococcus aureus
<220> FEATURE:
<221> NAME/KEY: MISC_FEATURE
<222> LOCATION: (342)..(351)
<223> OTHER INFORMATION: Amino acids corresponding to these residues may
      be lacking/deleted.

<400> SEQUENCE: 2

Met Lys Asn Lys Lys Arg Val Leu Ile Ala Ser Ser Leu Ser Cys Ala
1               5                   10                  15

Ile Leu Leu Leu Ser Ala Ala Thr Thr Gln Ala Asn Ser Ala His Lys
                20                  25                  30

Asp Ser Gln Asp Gln Asn Lys Lys Glu His Val Asp Lys Ser Gln Gln
            35                  40                  45

Lys Asp Lys Arg Asn Val Thr Asn Lys Asp Lys Asn Ser Thr Ala Pro
50                  55                  60

Asp Asp Ile Gly Lys Asn Gly Lys Ile Thr Lys Arg Thr Glu Thr Val
65                  70                  75                  80

Tyr Asp Glu Lys Thr Asn Ile Leu Gln Asn Leu Gln Phe Asp Phe Ile
                85                  90                  95

Asp Asp Pro Thr Tyr Asp Lys Asn Val Leu Leu Val Lys Lys Gln Gly
            100                 105                 110

Ser Ile His Ser Asn Leu Lys Phe Glu Ser His Lys Glu Glu Lys Asn
        115                 120                 125

Ser Asn Trp Leu Lys Tyr Pro Ser Glu Tyr His Val Asp Phe Gln Val
    130                 135                 140

Lys Arg Asn Arg Lys Thr Glu Ile Leu Asp Gln Leu Pro Lys Asn Lys
145                 150                 155                 160

Ile Ser Thr Ala Lys Val Asp Ser Thr Phe Ser Tyr Ser Ser Gly Gly
                165                 170                 175

Lys Phe Asp Ser Thr Lys Gly Ile Gly Arg Thr Ser Ser Asn Ser Tyr
            180                 185                 190

Ser Lys Thr Ile Ser Tyr Asn Gln Gln Asn Tyr Asp Thr Ile Ala Ser
        195                 200                 205

Gly Lys Asn Asn Asn Trp His Val His Trp Ser Val Ile Ala Asn Asp
    210                 215                 220

Leu Lys Tyr Gly Gly Glu Val Lys Asn Arg Asn Asp Glu Leu Leu Phe
225                 230                 235                 240
```

```
Tyr Arg Asn Thr Arg Ile Ala Thr Val Glu Asn Pro Glu Leu Ser Phe
                245                 250                 255

Ala Ser Lys Tyr Arg Tyr Pro Ala Leu Val Arg Ser Gly Phe Asn Pro
            260                 265                 270

Glu Phe Leu Thr Tyr Leu Ser Asn Glu Lys Ser Asn Glu Lys Thr Gln
        275                 280                 285

Phe Glu Val Thr Tyr Thr Arg Asn Gln Asp Ile Leu Lys Asn Arg Pro
    290                 295                 300

Gly Ile His Tyr Ala Pro Pro Ile Leu Glu Lys Asn Lys Asp Gly Gln
305                 310                 315                 320

Arg Leu Ile Val Thr Tyr Glu Val Asp Trp Lys Asn Lys Thr Val Lys
                325                 330                 335

Val Val Asp Lys Tyr Ser Asp Asp Asn Lys Pro Tyr Lys Glu Gly
                340                 345                 350

<210> SEQ ID NO 3
<211> LENGTH: 351
<212> TYPE: PRT
<213> ORGANISM: Staphylococcus aureus
<220> FEATURE:
<221> NAME/KEY: MISC_FEATURE
<222> LOCATION: (342)..(351)
<223> OTHER INFORMATION: Amino acids corresponding to these residues may
      be lacking/deleted.

<400> SEQUENCE: 3

Met Lys Asn Lys Lys Arg Val Phe Ile Ala Ser Ser Leu Ser Cys Ala
1               5                   10                  15

Leu Leu Leu Leu Ser Ala Ala Asn Thr Glu Ala Asn Ser Ala Asn Lys
                20                  25                  30

Asp Ser Gln Asp Gln Thr Lys Lys Glu His Val Asp Lys Ala Gln Gln
            35                  40                  45

Lys Glu Lys Arg Asn Val Asn Asp Lys Asp Lys Asn Thr Pro Gly Pro
50                  55                  60

Asp Asp Ile Gly Lys Asn Gly Lys Val Thr Lys Arg Thr Val Ser Glu
65                  70                  75                  80

Tyr Asp Lys Glu Thr Asn Ile Leu Gln Asn Leu Gln Phe Asp Phe Ile
                85                  90                  95

Asp Asp Pro Thr Tyr Asp Lys Asn Val Leu Leu Val Lys Lys Gln Gly
            100                 105                 110

Ser Ile His Ser Asn Leu Lys Phe Glu Ser His Arg Asn Glu Thr Asn
            115                 120                 125

Ala Ser Trp Leu Lys Tyr Pro Ser Glu Tyr His Val Asp Phe Gln Val
        130                 135                 140

Gln Arg Asn Pro Lys Thr Glu Ile Leu Asp Gln Leu Pro Lys Asn Lys
145                 150                 155                 160

Ile Ser Thr Ala Lys Val Asp Ser Thr Phe Ser Tyr Ser Leu Gly Gly
                165                 170                 175

Lys Phe Asp Ser Thr Lys Gly Ile Gly Arg Thr Ser Ser Asn Ser Tyr
            180                 185                 190

Ser Lys Ser Ile Ser Tyr Asn Gln Gln Asn Tyr Asp Thr Ile Ala Ser
        195                 200                 205

Gly Lys Asn Asn Asn Arg His Val His Trp Ser Val Val Ala Asn Asp
    210                 215                 220

Leu Lys Tyr Gly Asn Glu Ile Lys Asn Arg Asn Asp Glu Phe Leu Phe
225                 230                 235                 240
```

```
Tyr Arg Asn Thr Arg Leu Ser Thr Val Glu Asn Pro Glu Leu Ser Phe
                245                 250                 255

Ala Ser Lys Tyr Arg Tyr Pro Ala Leu Val Arg Ser Gly Phe Asn Pro
            260                 265                 270

Glu Phe Leu Thr Tyr Ile Ser Asn Glu Lys Ser Asn Glu Lys Thr Arg
        275                 280                 285

Phe Glu Val Thr Tyr Thr Arg Asn Gln Asp Ile Leu Lys Asn Lys Pro
    290                 295                 300

Gly Ile His Tyr Gly Gln Pro Ile Leu Glu Gln Asn Lys Asp Gly Gln
305                 310                 315                 320

Arg Phe Ile Val Val Tyr Glu Val Asp Trp Lys Asn Lys Thr Val Lys
                325                 330                 335

Val Val Glu Lys Tyr Ser Asp Gln Asn Lys Pro Tyr Lys Glu Gly
            340                 345                 350
```

<210> SEQ ID NO 4
<211> LENGTH: 350
<212> TYPE: PRT
<213> ORGANISM: Staphylococcus aureus
<220> FEATURE:
<221> NAME/KEY: MISC_FEATURE
<222> LOCATION: (342)..(350)
<223> OTHER INFORMATION: Amino acids corresponding to these residues may
      be lacking/deleted. An additional amino acid was deleted from the
      C-terminal and is not shown.

<400> SEQUENCE: 4

```
Met Lys Asn Lys Lys Arg Val Leu Ile Ala Ser Ser Leu Ser Cys Ala
1               5                   10                  15

Ile Leu Leu Leu Ser Ala Ala Thr Thr Gln Ala Asn Ser Ala His Lys
                20                  25                  30

Asp Ser Gln Asp Gln Asn Lys Lys Glu His Val Asp Lys Ser Gln Gln
            35                  40                  45

Lys Glu Lys Arg Asn Val Thr Asn Lys Asp Lys Asn Ser Thr Val Pro
50                  55                  60

Asp Asp Ile Gly Lys Asn Gly Lys Ile Thr Lys Arg Thr Glu Thr Val
65                  70                  75                  80

Tyr Asp Glu Lys Thr Asn Ile Leu Gln Asn Leu Gln Phe Asp Phe Ile
                85                  90                  95

Asp Asp Pro Thr Tyr Asp Lys Asn Val Leu Leu Val Lys Lys Gln Gly
            100                 105                 110

Ser Ile His Ser Asn Leu Lys Phe Glu Ser His Lys Glu Glu Lys Asn
        115                 120                 125

Ser Asn Trp Leu Lys Tyr Pro Ser Glu Tyr His Val Asp Phe Gln Val
130                 135                 140

Lys Arg Asn Arg Lys Thr Glu Ile Leu Asp Gln Leu Pro Lys Asn Lys
145                 150                 155                 160

Ile Ser Thr Ala Lys Val Asp Ser Thr Phe Ser Tyr Ser Ser Gly Gly
                165                 170                 175

Lys Phe Asp Ser Thr Lys Gly Ile Gly Arg Thr Ser Ser Asn Ser Tyr
            180                 185                 190

Ser Lys Thr Ile Ser Tyr Asn Gln Gln Asn Tyr Asp Thr Ile Ala Ser
        195                 200                 205

Gly Lys Asn Asn Asn Trp His Val His Trp Ser Val Ile Ala Asn Asp
210                 215                 220

Leu Lys Tyr Gly Gly Glu Val Lys Asn Arg Asn Asp Glu Leu Leu Phe
```

```
               225                 230                 235                 240
Tyr Arg Asn Thr Arg Ile Ala Thr Val Glu Asn Pro Glu Leu Ser Phe
                            245                 250                 255

Ala Ser Lys Tyr Arg Tyr Pro Ala Leu Val Arg Ser Gly Phe Asn Pro
                260                 265                 270

Glu Phe Leu Thr Tyr Leu Ser Asn Glu Lys Ser Asn Glu Lys Thr Gln
                275                 280                 285

Phe Glu Val Thr Tyr Thr Arg Asn Gln Asp Ile Leu Lys Asn Arg Pro
            290                 295                 300

Gly Ile His Tyr Ala Pro Pro Ile Leu Glu Lys Asn Lys Glu Gly Gln
305                 310                 315                 320

Arg Leu Ile Val Thr Tyr Glu Val Asp Trp Lys Asn Lys Thr Val Lys
                        325                 330                 335

Val Val Asp Lys Tyr Ser Asp Asn Lys Ser Phe Arg Glu Gly
                340                 345                 350

<210> SEQ ID NO 5
<211> LENGTH: 350
<212> TYPE: PRT
<213> ORGANISM: Staphylococcus aureus
<220> FEATURE:
<221> NAME/KEY: MISC_FEATURE
<222> LOCATION: (342)..(350)
<223> OTHER INFORMATION: Amino acids corresponding to these residues may
      be lacking/deleted. An additional amino acid was deleted from the
      C-terminal and is not shown.

<400> SEQUENCE: 5

Met Lys Asn Lys Lys Arg Val Leu Ile Ala Ser Ser Leu Ser Cys Ala
1               5                   10                  15

Ile Leu Leu Leu Ser Ala Ala Thr Thr Gln Ala Asn Ser Ala His Lys
            20                  25                  30

Asp Ser Gln Asp Gln Asn Lys Lys Glu His Val Asp Lys Ser Gln Gln
        35                  40                  45

Lys Asp Lys Arg Asn Val Thr Asn Lys Asp Lys Asn Ser Thr Ala Pro
    50                  55                  60

Asp Asp Ile Gly Lys Asn Gly Lys Ile Thr Lys Arg Thr Glu Thr Val
65                  70                  75                  80

Tyr Asp Glu Lys Thr Asn Ile Leu Gln Asn Leu Gln Phe Asp Phe Ile
                85                  90                  95

Asp Asp Pro Thr Tyr Asp Lys Asn Val Leu Leu Val Lys Lys Gln Gly
            100                 105                 110

Ser Ile His Ser Asn Leu Lys Phe Glu Ser His Lys Glu Glu Lys Asn
        115                 120                 125

Ser Asn Trp Leu Lys Tyr Pro Ser Glu Tyr His Val Asp Phe Gln Val
    130                 135                 140

Lys Arg Asn Pro Lys Thr Glu Ile Leu Asp Gln Leu Pro Lys Asn Lys
145                 150                 155                 160

Ile Ser Thr Ala Lys Val Asp Ser Thr Phe Ser Tyr Ser Ser Gly Gly
                165                 170                 175

Lys Phe Asp Ser Thr Lys Gly Ile Gly Arg Thr Ser Ser Asn Ser Tyr
            180                 185                 190

Ser Lys Thr Ile Ser Tyr Asn Gln Gln Asn Tyr Asp Thr Ile Ala Ser
        195                 200                 205

Gly Lys Asn Asn Asn Trp His Val His Trp Ser Val Ile Ala Asn Asp
    210                 215                 220
```

-continued

```
Leu Lys Tyr Gly Gly Glu Val Lys Asn Arg Asn Asp Glu Leu Leu Phe
225                 230                 235                 240

Tyr Arg Asn Thr Arg Ile Ala Thr Val Glu Asn Pro Glu Leu Ser Phe
            245                 250                 255

Ala Ser Lys Tyr Arg Tyr Pro Ala Leu Val Arg Ser Gly Phe Asn Pro
        260                 265                 270

Glu Phe Leu Thr Tyr Leu Ser Asn Glu Lys Ser Asn Glu Lys Thr Gln
    275                 280                 285

Phe Glu Val Thr Tyr Thr Arg Asn Gln Asp Ile Leu Lys Asn Arg Pro
290                 295                 300

Gly Ile His Tyr Ala Pro Pro Ile Leu Glu Lys Asn Lys Glu Gly Gln
305                 310                 315                 320

Arg Leu Ile Val Thr Tyr Glu Val Asp Trp Lys Asn Lys Thr Val Lys
                325                 330                 335

Val Val Asp Lys Tyr Thr Asp Asn Lys Ser Phe Arg Glu Gly
                340                 345                 350
```

<210> SEQ ID NO 6
<211> LENGTH: 350
<212> TYPE: PRT
<213> ORGANISM: Staphylococcus aureus
<220> FEATURE:
<221> NAME/KEY: MISC_FEATURE
<222> LOCATION: (342)..(350)
<223> OTHER INFORMATION: Amino acids corresponding to these residues may
      be lacking/deleted. An additional amino acid was deleted from the
      C-terminal and is not shown.

<400> SEQUENCE: 6

```
Met Lys Asn Lys Lys Arg Val Leu Ile Ala Ser Ser Leu Ser Cys Ala
1               5                   10                  15

Ile Leu Leu Leu Ser Ala Ala Thr Thr Gln Ala Asn Ser Ala His Lys
                20                  25                  30

Asp Ser Gln Asp Gln Asn Lys Lys Glu His Val Asp Lys Ser Gln Gln
            35                  40                  45

Lys Glu Lys Arg Asn Val Thr Asn Lys Asp Lys Asn Ser Thr Val Pro
50                  55                  60

Asp Asp Ile Gly Lys Asn Gly Lys Ile Thr Lys Arg Thr Glu Thr Val
65                  70                  75                  80

Tyr Asp Glu Lys Thr Asn Ile Leu Gln Asn Leu Gln Phe Asp Phe Ile
                85                  90                  95

Asp Asp Pro Thr Tyr Asp Lys Asn Val Leu Leu Val Lys Lys Gln Gly
            100                 105                 110

Ser Ile His Ser Asn Leu Lys Phe Glu Ser His Lys Glu Glu Lys Asn
        115                 120                 125

Ser Asn Trp Leu Lys Tyr Pro Ser Glu Tyr His Val Asp Phe Gln Val
    130                 135                 140

Lys Arg Asn Pro Lys Thr Glu Ile Leu Asp Gln Leu Pro Lys Asn Lys
145                 150                 155                 160

Ile Ser Thr Ala Lys Val Asp Ser Thr Phe Ser Tyr Ser Ser Gly Gly
                165                 170                 175

Lys Phe Asp Ser Thr Lys Gly Ile Gly Arg Thr Ser Ser Asn Ser Tyr
            180                 185                 190

Ser Lys Thr Ile Ser Tyr Asn Gln Gln Asn Tyr Asp Thr Ile Ala Ser
        195                 200                 205

Gly Lys Asn Asn Asn Trp His Val His Trp Ser Val Ile Ala Asn Asp
    210                 215                 220
```

```
Leu Lys Tyr Gly Gly Glu Val Lys Asn Arg Asn Asp Glu Leu Leu Phe
225                 230                 235                 240

Tyr Arg Asn Thr Arg Ile Ala Thr Val Glu Asn Pro Glu Leu Ser Phe
                245                 250                 255

Ala Ser Lys Tyr Arg Tyr Pro Ala Leu Val Arg Ser Gly Phe Asn Pro
            260                 265                 270

Glu Phe Leu Thr Tyr Leu Ser Asn Glu Lys Ser Asn Glu Lys Thr Gln
        275                 280                 285

Phe Glu Val Thr Tyr Thr Arg Asn Gln Asp Ile Leu Lys Asn Arg Pro
    290                 295                 300

Gly Ile His Tyr Ala Pro Pro Ile Leu Glu Lys Asn Lys Glu Gly Gln
305                 310                 315                 320

Arg Leu Ile Val Thr Tyr Glu Val Asp Trp Lys Asn Lys Thr Val Lys
                325                 330                 335

Val Val Asp Lys Tyr Ser Asp Asn Lys Ser Phe Arg Glu Gly
            340                 345                 350

<210> SEQ ID NO 7
<211> LENGTH: 351
<212> TYPE: PRT
<213> ORGANISM: Staphylococcus aureus
<220> FEATURE:
<221> NAME/KEY: MISC_FEATURE
<222> LOCATION: (342)..(351)
<223> OTHER INFORMATION: Amino acids corresponding to these residues may
      be lacking/deleted.

<400> SEQUENCE: 7

Met Lys Asn Lys Lys Arg Val Leu Ile Ala Ser Ser Leu Ser Cys Ala
1               5                   10                  15

Ile Leu Leu Leu Ser Ala Ala Thr Thr Gln Ala Asn Ser Ala His Lys
                20                  25                  30

Asp Ser Gln Asp Gln Asn Lys Lys Glu His Val Asp Lys Ser Gln Gln
            35                  40                  45

Lys Asp Lys Arg Asn Val Thr Asn Lys Asp Lys Asn Ser Thr Val Pro
50                  55                  60

Asp Asp Ile Gly Lys Asn Gly Lys Ile Thr Lys Arg Thr Glu Thr Val
65                  70                  75                  80

Tyr Asp Glu Lys Thr Asn Ile Leu Gln Asn Leu Gln Phe Asp Phe Ile
                85                  90                  95

Asp Asp Pro Thr Tyr Asp Lys Asn Val Leu Leu Val Lys Lys Gln Gly
            100                 105                 110

Ser Ile His Ser Asn Leu Lys Phe Glu Ser His Lys Glu Glu Lys Asn
        115                 120                 125

Ser Asn Trp Leu Lys Tyr Pro Ser Glu Tyr His Val Asp Phe Gln Val
    130                 135                 140

Lys Arg Asn Arg Lys Thr Glu Ile Leu Asp Gln Leu Pro Lys Asn Lys
145                 150                 155                 160

Ile Ser Thr Ala Lys Val Asp Ser Thr Phe Ser Tyr Ser Ser Gly Gly
                165                 170                 175

Lys Phe Asp Ser Thr Lys Gly Ile Gly Arg Thr Ser Ser Asn Ser Tyr
            180                 185                 190

Ser Lys Thr Ile Ser Tyr Asn Gln Gln Asn Tyr Asp Thr Ile Ala Ser
        195                 200                 205

Gly Lys Asn Asn Asn Trp His Val His Trp Ser Val Ile Ala Asn Asp
    210                 215                 220
```

```
Leu Lys Tyr Gly Gly Glu Val Lys Asn Arg Asn Asp Glu Leu Leu Phe
225                 230                 235                 240

Tyr Arg Asn Thr Arg Ile Ala Thr Val Glu Asn Pro Glu Leu Ser Phe
                245                 250                 255

Ala Ser Lys Tyr Arg Tyr Pro Ala Leu Val Arg Ser Gly Phe Asn Pro
            260                 265                 270

Glu Phe Leu Thr Tyr Leu Ser Asn Glu Lys Ser Asn Glu Lys Thr Gln
        275                 280                 285

Phe Glu Val Thr Tyr Thr Arg Asn Gln Asp Ile Leu Lys Asn Arg Pro
    290                 295                 300

Gly Ile His Tyr Ala Pro Pro Ile Leu Glu Lys Asn Lys Asp Gly Gln
305                 310                 315                 320

Arg Leu Ile Val Thr Tyr Glu Val Asp Trp Lys Asn Lys Thr Val Lys
                325                 330                 335

Val Val Asp Lys Tyr Ser Asp Asp Asn Lys Pro Tyr Lys Glu Gly
            340                 345                 350

<210> SEQ ID NO 8
<211> LENGTH: 351
<212> TYPE: PRT
<213> ORGANISM: Staphylococcus aureus
<220> FEATURE:
<221> NAME/KEY: MISC_FEATURE
<222> LOCATION: (342)..(351)
<223> OTHER INFORMATION: Amino acids corresponding to these residues may
      be lacking/deleted.

<400> SEQUENCE: 8

Met Lys Asn Lys Lys Arg Val Leu Ile Ala Ser Ser Leu Ser Cys Ala
1               5                   10                  15

Ile Leu Leu Leu Ser Ala Ala Thr Thr Gln Ala Asn Ser Ala His Lys
                20                  25                  30

Asp Ser Gln Asp Gln Asn Lys Lys Glu His Val Asp Lys Ser Gln Gln
            35                  40                  45

Lys Asp Lys Arg Asn Val Thr Asn Lys Asp Lys Asn Ser Thr Val Pro
50                  55                  60

Asp Asp Ile Gly Lys Asn Gly Lys Ile Thr Lys Arg Thr Glu Thr Val
65                  70                  75                  80

Tyr Asp Glu Lys Thr Asn Ile Leu Gln Asn Leu Gln Phe Asp Phe Ile
                85                  90                  95

Asp Asp Pro Thr Tyr Asp Lys Asn Val Leu Leu Val Lys Lys Gln Gly
            100                 105                 110

Ser Ile His Ser Asn Leu Lys Phe Glu Ser His Lys Glu Glu Lys Asn
        115                 120                 125

Ser Asn Trp Leu Lys Tyr Pro Ser Glu Tyr His Val Asp Phe Gln Val
    130                 135                 140

Lys Arg Asn Arg Lys Thr Glu Ile Leu Asp Gln Leu Pro Lys Asn Lys
145                 150                 155                 160

Ile Ser Thr Ala Lys Val Asp Ser Thr Phe Ser Tyr Ser Ser Gly Gly
                165                 170                 175

Lys Phe Asp Ser Thr Lys Gly Ile Gly Arg Thr Ser Ser Asn Ser Tyr
            180                 185                 190

Ser Lys Thr Ile Ser Tyr Asn Gln Gln Lys Tyr Asp Thr Ile Ala Ile
        195                 200                 205

Gly Lys Asn Asn Asn Trp His Val His Trp Ser Val Ile Ala Asn Asp
    210                 215                 220
```

-continued

Leu Lys Tyr Gly Gly Glu Val Lys Asn Arg Asn Asp Glu Leu Leu Phe
225                 230                 235                 240

Tyr Arg Asn Thr Arg Ile Ala Thr Val Glu Asn Pro Glu Leu Ser Phe
                245                 250                 255

Ala Ser Lys Tyr Arg Tyr Pro Ala Leu Val Arg Ser Gly Phe Asn Pro
            260                 265                 270

Glu Phe Leu Thr Tyr Leu Ser Asn Glu Lys Ser Asn Glu Lys Thr Gln
        275                 280                 285

Phe Glu Val Thr Tyr Thr Arg Asn Gln Asp Ile Leu Lys Asn Arg Pro
    290                 295                 300

Gly Ile His Tyr Ala Pro Pro Ile Leu Glu Lys Asn Lys Asp Gly Gln
305                 310                 315                 320

Arg Leu Ile Val Thr Tyr Glu Val Asp Trp Lys Asn Lys Thr Val Lys
                325                 330                 335

Val Val Asp Lys Tyr Ser Asp Asp Asn Lys Pro Tyr Lys Glu Gly
            340                 345                 350

<210> SEQ ID NO 9
<211> LENGTH: 351
<212> TYPE: PRT
<213> ORGANISM: Staphylococcus aureus
<220> FEATURE:
<221> NAME/KEY: MISC_FEATURE
<222> LOCATION: (342)..(351)
<223> OTHER INFORMATION: Amino acids corresponding to these residues may
      be lacking/deleted.

<400> SEQUENCE: 9

Met Lys Asn Lys Lys Arg Val Leu Ile Ala Ser Ser Leu Ser Cys Ala
1               5                   10                  15

Ile Leu Leu Leu Ser Ala Ala Thr Thr Gln Ala Asn Ser Ala His Lys
                20                  25                  30

Asp Ser Gln Asp Gln Asn Lys Lys Glu His Val Asp Lys Ser Gln Gln
            35                  40                  45

Lys Asp Lys Arg Asn Val Thr Asn Lys Asp Lys Asn Ser Thr Ala Pro
50                  55                  60

Asp Asp Ile Gly Lys Asn Gly Lys Ile Thr Lys Arg Thr Glu Thr Val
65                  70                  75                  80

Tyr Asp Glu Lys Thr Asn Ile Leu Gln Asn Leu Gln Phe Asp Phe Ile
                85                  90                  95

Asp Asp Pro Thr Tyr Asp Lys Asn Val Leu Leu Val Lys Lys Gln Gly
            100                 105                 110

Ser Ile His Ser Asn Leu Lys Phe Glu Ser His Lys Glu Glu Lys Asn
        115                 120                 125

Ser Asn Trp Leu Lys Tyr Pro Ser Glu Tyr His Val Asp Phe Gln Val
    130                 135                 140

Lys Arg Asn Arg Lys Thr Glu Ile Leu Asp Gln Leu Pro Lys Asn Lys
145                 150                 155                 160

Ile Ser Thr Ala Lys Val Asp Ser Thr Phe Ser Tyr Ser Ser Gly Gly
                165                 170                 175

Lys Phe Asp Ser Thr Lys Gly Ile Gly Arg Thr Ser Ser Asn Ser Tyr
            180                 185                 190

Ser Lys Thr Ile Ser Tyr Asn Gln Gln Asn Tyr Asp Thr Ile Ala Ser
        195                 200                 205

Gly Lys Asn Asn Asn Trp His Val His Trp Ser Val Ile Ala Asn Asp
    210                 215                 220

-continued

Leu Lys Tyr Gly Gly Glu Val Lys Asn Arg Asn Asp Glu Leu Leu Phe
225                 230                 235                 240

Tyr Arg Asn Thr Arg Ile Ala Thr Val Glu Asn Pro Glu Leu Ser Phe
            245                 250                 255

Ala Ser Lys Tyr Arg Tyr Pro Ala Leu Val Arg Ser Gly Phe Asn Pro
        260                 265                 270

Glu Phe Leu Thr Tyr Leu Ser Asn Glu Lys Ser Asn Glu Lys Thr Gln
    275                 280                 285

Phe Glu Val Thr Tyr Thr Arg Asn Gln Asp Ile Leu Lys Asn Arg Pro
290                 295                 300

Gly Ile His Tyr Ala Pro Pro Ile Leu Glu Lys Asn Lys Asp Gly Gln
305                 310                 315                 320

Arg Leu Ile Val Thr Tyr Glu Val Asp Trp Lys Asn Lys Thr Val Lys
                325                 330                 335

Val Val Asp Lys Tyr Ser Asp Asp Asn Lys Pro Tyr Lys Glu Gly
            340                 345                 350

<210> SEQ ID NO 10
<211> LENGTH: 351
<212> TYPE: PRT
<213> ORGANISM: Staphylococcus aureus
<220> FEATURE:
<221> NAME/KEY: MISC_FEATURE
<222> LOCATION: (342)..(351)
<223> OTHER INFORMATION: Amino acids corresponding to these residues may
      be lacking/deleted.

<400> SEQUENCE: 10

Met Lys Asn Lys Lys Arg Val Phe Ile Ala Ser Ser Leu Ser Cys Ala
1               5                   10                  15

Leu Leu Leu Leu Ser Ala Ala Asn Thr Glu Ala Asn Ser Ala Asn Lys
            20                  25                  30

Asp Ser Gln Asp Gln Thr Lys Lys Glu His Val Asp Lys Ala Gln Gln
        35                  40                  45

Lys Glu Lys Arg Asn Val Asn Asp Lys Asp Lys Asn Thr Pro Gly Pro
    50                  55                  60

Asp Asp Ile Gly Lys Asn Gly Lys Val Thr Lys Arg Thr Val Ser Glu
65                  70                  75                  80

Tyr Asp Lys Glu Thr Asn Ile Leu Gln Asn Leu Gln Phe Asp Phe Ile
                85                  90                  95

Asp Asp Pro Thr Tyr Asp Lys Asn Val Leu Leu Val Lys Lys Gln Gly
            100                 105                 110

Ser Ile His Ser Asn Leu Lys Phe Glu Ser His Arg Asn Glu Thr Asn
        115                 120                 125

Ala Ser Trp Leu Lys Tyr Pro Ser Glu Tyr His Val Asp Phe Gln Val
    130                 135                 140

Gln Arg Asn Pro Lys Thr Glu Ile Leu Asp Gln Leu Pro Lys Asn Lys
145                 150                 155                 160

Ile Ser Thr Ala Lys Val Asp Ser Thr Phe Ser Tyr Ser Leu Gly Gly
                165                 170                 175

Lys Phe Asp Ser Thr Lys Gly Ile Gly Arg Thr Ser Ser Asn Ser Tyr
            180                 185                 190

Ser Lys Ser Ile Ser Tyr Asn Gln Gln Asn Tyr Asp Thr Ile Ala Ser
        195                 200                 205

Gly Lys Asn Asn Asn Arg His Val His Trp Ser Val Val Ala Asn Asp
    210                 215                 220

```
Leu Lys Tyr Gly Asn Glu Ile Lys Asn Arg Asn Asp Glu Phe Leu Phe
225                 230                 235                 240

Tyr Arg Asn Thr Arg Leu Ser Thr Val Glu Asn Pro Glu Leu Ser Phe
                245                 250                 255

Ala Ser Lys Tyr Arg Tyr Pro Ala Leu Val Arg Ser Gly Phe Asn Pro
            260                 265                 270

Glu Phe Leu Thr Tyr Ile Ser Asn Glu Lys Thr Asn Asp Lys Thr Arg
        275                 280                 285

Phe Glu Val Thr Tyr Thr Arg Asn Gln Asp Ile Leu Lys Asn Lys Pro
    290                 295                 300

Gly Ile His Tyr Gly Gln Pro Ile Leu Glu Gln Asn Lys Asp Gly Gln
305                 310                 315                 320

Arg Phe Ile Val Val Tyr Glu Val Asp Trp Lys Asn Lys Thr Val Lys
                325                 330                 335

Val Val Glu Lys Tyr Ser Asp Gln Asn Lys Pro Tyr Lys Glu Gly
                340                 345                 350
```

<210> SEQ ID NO 11
<211> LENGTH: 351
<212> TYPE: PRT
<213> ORGANISM: Staphylococcus aureus
<220> FEATURE:
<221> NAME/KEY: MISC_FEATURE
<222> LOCATION: (342)..(351)
<223> OTHER INFORMATION: Amino acids corresponding to these residues may
      be lacking/deleted.

<400> SEQUENCE: 11

```
Met Lys Asn Lys Lys Arg Val Phe Ile Ala Ser Ser Leu Ser Cys Ala
1               5                   10                  15

Leu Leu Leu Leu Ser Ala Ala Asn Thr Glu Ala Asn Ser Ala Asn Lys
                20                  25                  30

Asp Ser Gln Asp Gln Thr Lys Lys Glu His Val Asp Lys Ala Gln Gln
            35                  40                  45

Lys Glu Lys Arg Asn Val Asn Asp Lys Asp Lys Asn Thr Pro Gly Pro
50                  55                  60

Asp Asp Ile Gly Lys Asn Gly Lys Val Thr Lys Arg Thr Glu Thr Val
65                  70                  75                  80

Tyr Asp Glu Lys Thr Asn Ile Leu Gln Asn Leu Gln Phe Asp Phe Ile
                85                  90                  95

Asp Asp Pro Thr Tyr Asp Lys Asn Val Leu Leu Val Lys Lys Gln Gly
            100                 105                 110

Ser Ile His Ser Asn Leu Lys Phe Glu Ser His Lys Glu Glu Asn Asn
        115                 120                 125

Ser Ser Trp Leu Lys Tyr Pro Ser Glu Tyr His Val Asp Phe Gln Val
    130                 135                 140

Lys Ser Asn Arg Lys Thr Glu Ile Leu Asp Gln Leu Pro Lys Asn Lys
145                 150                 155                 160

Ile Ser Thr Ala Lys Val Asp Ser Thr Phe Ser Tyr Asn Ser Gly Gly
                165                 170                 175

Lys Phe Asp Ser Val Lys Gly Val Gly Arg Thr Ser Ser Asn Ser Tyr
            180                 185                 190

Ser Lys Thr Ile Ser Tyr Asn Gln Gln Asn Tyr Asp Thr Ile Ala Ser
        195                 200                 205

Gly Lys Asn Asn Asn Trp His Val His Trp Ser Val Val Ala Asn Asp
    210                 215                 220
```

```
Leu Lys Tyr Gly Gly Glu Val Lys Asn Arg Asn Asp Phe Leu Phe
225                 230                 235                 240

Tyr Arg Asn Thr Arg Leu Ser Thr Val Glu Asn Pro Glu Leu Ser Phe
            245                 250                 255

Ala Ser Lys Tyr Arg Tyr Pro Ala Leu Val Arg Ser Gly Phe Asn Pro
            260                 265                 270

Glu Phe Leu Thr Tyr Leu Ser Asn Glu Lys Ser Asn Glu Lys Thr Gln
            275                 280                 285

Phe Glu Val Thr Tyr Thr Arg Asn Gln Asp Val Leu Lys Asn Lys Pro
            290                 295                 300

Gly Ile His Tyr Ala Pro Pro Ile Leu Glu Lys Asn Lys Asp Gly Gln
305                 310                 315                 320

Arg Leu Ile Val Thr Tyr Glu Val Asp Trp Lys Asn Lys Thr Val Lys
                325                 330                 335

Val Ile Asp Lys Tyr Ser Asp Glu Asn Lys Pro Tyr Lys Glu Gly
            340                 345                 350
```

<210> SEQ ID NO 12
<211> LENGTH: 351
<212> TYPE: PRT
<213> ORGANISM: Staphylococcus aureus
<220> FEATURE:
<221> NAME/KEY: MISC_FEATURE
<222> LOCATION: (342)..(351)
<223> OTHER INFORMATION: Amino acids corresponding to these residues may be lacking/deleted.

<400> SEQUENCE: 12

```
Met Lys Asn Lys Lys Arg Val Phe Ile Ala Ser Ser Leu Ser Cys Val
1               5                   10                  15

Leu Leu Leu Leu Ser Ala Ala Asn Thr Glu Ala Asn Ser Ala Asn Lys
                20                  25                  30

Asp Ser Gln Asp Gln Thr Lys Lys Glu His Val Asp Lys Ala Gln Gln
            35                  40                  45

Lys Glu Lys Arg Asn Val Asn Asp Lys Asp Lys Asn Thr Pro Gly Pro
50                  55                  60

Asp Asp Ile Gly Lys Asn Gly Lys Val Thr Lys Arg Thr Val Ser Glu
65                  70                  75                  80

Tyr Asp Lys Glu Thr Asn Ile Leu Gln Asn Leu Gln Phe Asp Phe Ile
            85                  90                  95

Asp Asp Pro Thr Tyr Asp Lys Asn Val Leu Leu Val Lys Lys Gln Gly
            100                 105                 110

Ser Ile His Ser Asn Leu Lys Phe Glu Ser His Arg Asn Glu Thr Asn
            115                 120                 125

Ala Ser Trp Leu Lys Tyr Pro Ser Glu Tyr His Val Asp Phe Gln Val
            130                 135                 140

Gln Arg Asn Pro Lys Thr Glu Ile Leu Asp Gln Leu Pro Lys Asn Lys
145                 150                 155                 160

Ile Ser Thr Ala Lys Val Asp Ser Thr Phe Ser Tyr Ser Leu Gly Gly
                165                 170                 175

Lys Phe Asp Ser Thr Lys Gly Ile Gly Arg Thr Ser Ser Asn Ser Tyr
            180                 185                 190

Ser Lys Ser Ile Ser Tyr Asn Gln Gln Asn Tyr Asp Thr Ile Ala Ser
            195                 200                 205

Gly Lys Asn Asn Asn Arg His Val His Trp Ser Val Val Ala Asn Asp
210                 215                 220
```

```
Leu Lys Tyr Gly Asn Glu Ile Lys Asn Arg Asn Asp Glu Phe Leu Phe
225                 230                 235                 240

Tyr Arg Asn Thr Arg Leu Ser Thr Val Glu Asn Pro Glu Leu Ser Phe
                245                 250                 255

Ala Ser Lys Tyr Arg Tyr Pro Ala Leu Val Arg Ser Gly Phe Asn Pro
            260                 265                 270

Glu Phe Leu Thr Tyr Ile Ser Asn Glu Lys Ser Asn Glu Lys Thr Arg
        275                 280                 285

Phe Glu Val Thr Tyr Thr Arg Asn Gln Asp Ile Leu Lys Asn Lys Pro
290                 295                 300

Gly Ile His Tyr Gly Gln Pro Ile Leu Glu Gln Asn Lys Asp Gly Gln
305                 310                 315                 320

Arg Phe Ile Val Val Tyr Glu Val Asp Trp Lys Asn Lys Thr Val Lys
                325                 330                 335

Val Val Glu Lys Tyr Ser Asp Gln Asn Lys Pro Tyr Lys Glu Gly
                340                 345                 350

<210> SEQ ID NO 13
<211> LENGTH: 351
<212> TYPE: PRT
<213> ORGANISM: Staphylococcus aureus
<220> FEATURE:
<221> NAME/KEY: MISC_FEATURE
<222> LOCATION: (342)..(351)
<223> OTHER INFORMATION: Amino acids corresponding to these residues may
      be lacking/deleted.

<400> SEQUENCE: 13

Met Lys Asn Lys Lys Arg Val Phe Ile Ala Ser Ser Leu Ser Cys Ala
1               5                   10                  15

Leu Leu Leu Leu Ser Ala Ala Asn Thr Glu Ala Asn Ser Ala Asn Lys
                20                  25                  30

Asp Ser Gln Asp Gln Thr Lys Lys Glu His Val Asp Lys Ala Gln Gln
            35                  40                  45

Lys Glu Lys Arg Asn Val Asn Asp Lys Asp Lys Asn Thr Pro Gly Pro
        50                  55                  60

Asp Asp Ile Gly Lys Asn Gly Lys Val Thr Lys Arg Thr Glu Thr Val
65              70                  75                  80

Tyr Asp Glu Lys Thr Asn Ile Leu Gln Asn Leu Gln Phe Asp Phe Ile
                85                  90                  95

Asp Asp Pro Thr Tyr Asp Lys Asn Ile Leu Leu Val Lys Lys Gln Gly
            100                 105                 110

Ser Ile His Ser Asn Leu Lys Phe Glu Ser His Lys Glu Glu Asn Asn
        115                 120                 125

Ser Ser Trp Leu Lys Tyr Pro Ser Glu Tyr His Val Asp Phe Gln Val
    130                 135                 140

Lys Arg Asn Arg Lys Thr Glu Ile Leu Asp Gln Leu Pro Lys Asn Lys
145                 150                 155                 160

Ile Ser Thr Ala Lys Val Asp Ser Thr Phe Ser Tyr Asn Ser Gly Gly
                165                 170                 175

Lys Phe Asp Ser Val Lys Gly Val Gly Arg Thr Ser Ser Asn Ser Tyr
            180                 185                 190

Ser Lys Thr Ile Ser Tyr Asn Gln Gln Asn Tyr Asp Thr Ile Ala Ser
        195                 200                 205

Gly Lys Asn Asn Asn Trp His Val His Trp Ser Val Val Ala Asn Asp
    210                 215                 220
```

```
Leu Lys Tyr Gly Gly Glu Val Lys Asn Arg Asn Asp Glu Phe Leu Phe
225                 230                 235                 240

Tyr Arg Thr Thr Arg Leu Ser Thr Val Glu Asn Pro Glu Leu Ser Phe
                245                 250                 255

Ala Ser Lys Tyr Arg Tyr Pro Ala Leu Val Arg Ser Gly Phe Asn Pro
            260                 265                 270

Glu Phe Leu Thr Tyr Leu Ser Asn Glu Lys Ser Asn Glu Lys Thr Gln
        275                 280                 285

Phe Glu Val Thr Tyr Thr Arg Asn Gln Asp Ile Leu Lys Asn Lys Pro
    290                 295                 300

Gly Ile His Tyr Ala Pro Pro Ile Leu Glu Lys Asn Lys Asp Gly Gln
305                 310                 315                 320

Arg Leu Ile Val Thr Tyr Glu Val Asp Trp Lys Asn Lys Thr Val Lys
                325                 330                 335

Val Ile Asp Lys Tyr Ser Asp Asp Asn Lys Pro Tyr Lys Glu Gly
            340                 345                 350

<210> SEQ ID NO 14
<211> LENGTH: 351
<212> TYPE: PRT
<213> ORGANISM: Staphylococcus aureus
<220> FEATURE:
<221> NAME/KEY: MISC_FEATURE
<222> LOCATION: (342)..(351)
<223> OTHER INFORMATION: Amino acids corresponding to these residues may
      be lacking/deleted.

<400> SEQUENCE: 14

Met Lys Asn Lys Lys Arg Val Leu Ile Ala Ser Ser Leu Ser Cys Ala
1               5                   10                  15

Ile Leu Leu Leu Ser Ala Ala Thr Thr Gln Ala Asn Ser Ala His Lys
            20                  25                  30

Asp Ser Gln Asp Gln Asn Lys Lys Glu His Val Asp Lys Ser Gln Gln
        35                  40                  45

Lys Asp Lys Arg Asn Val Thr Asn Lys Asp Lys Asn Ser Thr Val Pro
50                  55                  60

Asp Asp Ile Gly Lys Asn Gly Lys Ile Thr Lys Arg Thr Glu Thr Val
65                  70                  75                  80

Tyr Asp Glu Lys Thr Asn Ile Leu Gln Asn Leu Gln Phe Asp Phe Ile
                85                  90                  95

Asp Asp Pro Thr Tyr Asp Lys Asn Val Leu Leu Val Lys Lys Gln Gly
            100                 105                 110

Ser Ile His Ser Asn Leu Lys Phe Glu Ser His Lys Glu Glu Lys Asn
        115                 120                 125

Ser Asn Trp Leu Lys Tyr Pro Ser Glu Tyr His Val Asp Phe Gln Val
    130                 135                 140

Lys Arg Asn Arg Lys Thr Glu Ile Leu Asp Gln Leu Pro Lys Asn Lys
145                 150                 155                 160

Ile Ser Thr Ala Lys Val Asp Ser Thr Phe Ser Tyr Ser Ser Gly Gly
                165                 170                 175

Lys Phe Asp Ser Thr Lys Gly Ile Gly Arg Thr Ser Ser Asn Ser Tyr
            180                 185                 190

Ser Lys Thr Ile Ser Tyr Asn Gln Gln Asn Tyr Asp Thr Ile Ala Ser
        195                 200                 205

Gly Lys Asn Asn Asn Trp His Val His Trp Ser Val Ile Ala Asn Asp
    210                 215                 220
```

Leu Lys Tyr Gly Gly Glu Val Lys Asn Arg Asn Asp Glu Leu Leu Phe
225                 230                 235                 240

Tyr Arg Asn Thr Arg Ile Ala Thr Val Glu Asn Pro Glu Leu Ser Phe
                245                 250                 255

Ala Ser Lys Tyr Arg Tyr Pro Ala Leu Val Arg Ser Gly Phe Asn Pro
            260                 265                 270

Glu Phe Leu Thr Tyr Leu Ser Asn Glu Lys Ser Asn Glu Lys Thr Gln
        275                 280                 285

Phe Glu Val Thr Tyr Thr Arg Asn Gln Asp Ile Leu Lys Asn Arg Pro
290                 295                 300

Gly Ile His Tyr Ala Pro Ser Ile Leu Glu Lys Asn Lys Asp Gly Gln
305                 310                 315                 320

Arg Leu Ile Val Thr Tyr Glu Val Asp Trp Lys Asn Lys Thr Val Lys
                325                 330                 335

Val Val Asp Lys Tyr Ser Asp Asp Asn Lys Pro Tyr Lys Glu Gly
            340                 345                 350

<210> SEQ ID NO 15
<211> LENGTH: 338
<212> TYPE: PRT
<213> ORGANISM: Staphylococcus aureus

<400> SEQUENCE: 15

Met Ile Lys Gln Leu Cys Lys Asn Ile Thr Ile Cys Ser Leu Ala Leu
1               5                   10                  15

Ser Thr Ala Leu Thr Val Phe Pro Ala Thr Ser Tyr Ala Lys Ile Asn
            20                  25                  30

Ser Glu Ile Lys Gln Val Ser Glu Lys Asn Leu Asp Gly Asp Thr Lys
        35                  40                  45

Met Tyr Thr Arg Thr Ala Thr Thr Ser Asp Ser Gln Lys Asn Ile Thr
50                  55                  60

Gln Ser Leu Gln Phe Asn Phe Leu Thr Glu Pro Asn Tyr Asp Lys Glu
65                  70                  75                  80

Thr Val Phe Ile Lys Ala Lys Gly Thr Ile Gly Ser Gly Leu Arg Ile
                85                  90                  95

Leu Asp Pro Asn Gly Tyr Trp Asn Ser Thr Leu Arg Trp Pro Gly Ser
            100                 105                 110

Tyr Ser Val Ser Ile Gln Asn Val Asp Asp Asn Asn Thr Asn Val
        115                 120                 125

Thr Asp Phe Ala Pro Lys Asn Gln Asp Glu Ser Arg Glu Val Lys Tyr
    130                 135                 140

Thr Tyr Gly Tyr Lys Thr Gly Gly Asp Phe Ser Ile Asn Arg Gly Gly
145                 150                 155                 160

Leu Thr Gly Asn Ile Thr Lys Glu Ser Asn Tyr Ser Glu Thr Ile Ser
                165                 170                 175

Tyr Gln Gln Pro Ser Tyr Arg Thr Leu Leu Asp Gln Ser Thr Ser His
            180                 185                 190

Lys Gly Val Gly Trp Lys Val Glu Ala His Leu Ile Asn Asn Met Gly
        195                 200                 205

His Asp His Thr Arg Gln Leu Thr Asn Asp Ser Asp Asn Arg Thr Lys
    210                 215                 220

Ser Glu Ile Phe Ser Leu Thr Arg Asn Gly Asn Leu Trp Ala Lys Asp
225                 230                 235                 240

Asn Phe Thr Pro Lys Asn Lys Met Pro Val Thr Val Ser Glu Gly Phe

```
                        245                 250                 255
Asn Pro Glu Phe Leu Ala Val Met Ser His Asp Lys Asp Lys Gly
            260                 265                 270

Lys Ser Gln Phe Val Val His Tyr Lys Arg Ser Met Asp Glu Phe Lys
        275                 280                 285

Ile Asp Trp Asn Arg His Gly Phe Trp Gly Tyr Trp Ser Gly Glu Asn
290                 295                 300

His Val Asp Lys Lys Glu Glu Lys Leu Ser Ala Leu Tyr Glu Val Asp
305                 310                 315                 320

Trp Lys Thr His Asn Val Lys Phe Val Lys Val Leu Asn Asp Asn Glu
                325                 330                 335

Lys Lys

<210> SEQ ID NO 16
<211> LENGTH: 339
<212> TYPE: PRT
<213> ORGANISM: Staphylococcus aureus

<400> SEQUENCE: 16

Met Ile Lys Gln Val Cys Lys Asn Ile Thr Ile Cys Ser Leu Ala Leu
1               5                   10                  15

Ser Thr Ala Leu Thr Val Phe Pro Ala Ser Ser Tyr Ala Glu Ile Lys
            20                  25                  30

Ser Lys Ile Thr Thr Val Ser Glu Lys Asn Leu Asp Gly Asp Thr Lys
        35                  40                  45

Met Tyr Thr Arg Thr Ala Thr Thr Ser Asp Thr Glu Lys Lys Ile Ser
50                  55                  60

Gln Ser Leu Gln Phe Asn Phe Leu Thr Glu Pro Asn Tyr Asp Lys Glu
65                  70                  75                  80

Thr Val Phe Ile Lys Ala Lys Gly Thr Ile Gly Ser Gly Leu Lys Ile
                85                  90                  95

Leu Asn Pro Asn Gly Tyr Trp Asn Ser Thr Leu Arg Trp Pro Gly Ser
            100                 105                 110

Tyr Ser Val Ser Ile Gln Asn Val Asp Asp Asn Asn Ser Thr Asn
        115                 120                 125

Val Thr Asp Phe Ala Pro Lys Asn Gln Asp Glu Ser Arg Glu Val Lys
130                 135                 140

Tyr Thr Tyr Gly Tyr Lys Thr Gly Gly Asp Phe Ser Ile Asn Arg Gly
145                 150                 155                 160

Gly Leu Thr Gly Asn Ile Thr Lys Glu Lys Asn Tyr Ser Glu Thr Ile
                165                 170                 175

Ser Tyr Gln Gln Pro Ser Tyr Arg Thr Leu Ile Asp Gln Pro Thr Thr
            180                 185                 190

Asn Lys Gly Val Ala Trp Lys Val Glu Ala His Ser Ile Asn Asn Met
        195                 200                 205

Gly His Asp His Thr Arg Gln Leu Thr Asn Asp Ser Asp Asp Arg Val
210                 215                 220

Lys Ser Glu Ile Phe Ser Leu Thr Arg Asn Gly Asn Leu Trp Ala Lys
225                 230                 235                 240

Asp Asn Phe Thr Pro Lys Asn Lys Met Pro Val Thr Val Ser Glu Gly
                245                 250                 255

Phe Asn Pro Glu Phe Leu Ala Val Met Ser His Asp Lys Asn Asp Lys
            260                 265                 270

Gly Lys Ser Arg Phe Ile Val His Tyr Lys Arg Ser Met Asp Asp Phe
```

```
                    275                 280                 285
Lys Leu Asp Trp Asn Lys His Gly Phe Trp Gly Tyr Trp Ser Gly Glu
        290                 295                 300

Asn His Val Asp Gln Lys Glu Glu Lys Leu Ser Ala Leu Tyr Glu Val
305                 310                 315                 320

Asp Trp Lys Thr His Asp Val Lys Leu Ile Lys Thr Phe Asn Asp Lys
                325                 330                 335

Glu Lys Lys

<210> SEQ ID NO 17
<211> LENGTH: 290
<212> TYPE: PRT
<213> ORGANISM: Staphylococcus aureus

<400> SEQUENCE: 17

Met Tyr Thr Arg Thr Ala Thr Thr Ser Asp Ser Gln Lys Asn Ile Thr
1               5                   10                  15

Gln Ser Leu Gln Phe Asn Phe Leu Thr Glu Pro Asn Tyr Asp Lys Glu
            20                  25                  30

Thr Val Phe Ile Lys Ala Lys Gly Thr Ile Gly Ser Gly Leu Arg Ile
        35                  40                  45

Leu Asp Pro Asn Gly Tyr Trp Asn Ser Thr Leu Arg Trp Pro Gly Ser
    50                  55                  60

Tyr Ser Val Ser Ile Gln Asn Val Asp Asp Asn Asn Thr Asn Val
65                  70                  75                  80

Thr Asp Phe Ala Pro Lys Asn Gln Asp Glu Ser Arg Glu Val Lys Tyr
                85                  90                  95

Thr Tyr Gly Tyr Lys Thr Gly Gly Asp Phe Ser Ile Asn Arg Gly Gly
            100                 105                 110

Leu Thr Gly Asn Ile Thr Lys Glu Ser Asn Tyr Ser Glu Thr Ile Ser
        115                 120                 125

Tyr Gln Gln Pro Ser Tyr Arg Thr Leu Leu Asp Gln Ser Thr Ser His
    130                 135                 140

Lys Gly Val Gly Trp Lys Val Glu Ala His Leu Ile Asn Asn Met Gly
145                 150                 155                 160

His Asp His Thr Arg Gln Leu Thr Asn Asp Ser Asp Asn Arg Thr Lys
                165                 170                 175

Ser Glu Ile Phe Ser Leu Thr Arg Asn Gly Asn Leu Trp Ala Lys Asp
            180                 185                 190

Asn Phe Thr Pro Lys Asp Lys Met Pro Val Thr Val Ser Glu Gly Phe
        195                 200                 205

Asn Pro Glu Phe Leu Ala Val Met Ser His Asp Lys Lys Asp Lys Gly
    210                 215                 220

Lys Ser Gln Phe Val Val His Tyr Lys Arg Ser Met Asp Glu Phe Lys
225                 230                 235                 240

Ile Asp Trp Asn Arg His Gly Phe Trp Gly Tyr Trp Ser Gly Glu Asn
                245                 250                 255

His Val Asp Lys Lys Glu Glu Lys Leu Ser Ala Leu Tyr Glu Val Asp
            260                 265                 270

Trp Lys Thr His Asn Val Lys Phe Val Lys Val Leu Asn Asp Asn Glu
        275                 280                 285

Lys Lys
    290
```

<210> SEQ ID NO 18
<211> LENGTH: 338
<212> TYPE: PRT
<213> ORGANISM: Staphylococcus aureus

<400> SEQUENCE: 18

Met Ile Lys Gln Val Cys Lys Asn Ile Thr Ile Cys Ser Leu Ala Leu
1               5                   10                  15

Ser Thr Ala Leu Thr Ile Phe Pro Ala Ser Ser Tyr Ala Lys Ile Asn
            20                  25                  30

Ser Glu Ile Lys Gln Val Ser Glu Lys Asn Leu Asp Gly Glu Thr Lys
        35                  40                  45

Met Tyr Thr Arg Thr Ala Thr Thr Ser Asp Ser Gln Lys Asn Ile Thr
    50                  55                  60

Gln Ser Leu Gln Phe Asn Phe Leu Thr Glu Lys Asn Tyr Asp Lys Glu
65                  70                  75                  80

Thr Val Phe Ile Lys Ala Lys Gly Thr Ile Gly Ser Gly Leu Arg Ile
                85                  90                  95

Leu Glu Pro Asn Gly Tyr Trp Asn Ser Thr Leu Arg Trp Pro Gly Ser
            100                 105                 110

Tyr Ser Val Ser Ile Gln Asn Val Asp Asp Asn Asn Thr Asn Val
        115                 120                 125

Thr Asp Phe Ala Pro Lys Asn Gln Asp Glu Ser Arg Glu Val Lys Tyr
    130                 135                 140

Thr Tyr Gly Tyr Lys Thr Gly Gly Asp Phe Ser Ile Asn Gln Gly Gly
145                 150                 155                 160

Leu Thr Gly Asn Ile Thr Lys Glu Ser Asn Tyr Ser Glu Thr Ile Ser
                165                 170                 175

Tyr Gln Gln Pro Ser Tyr Arg Thr Leu Ile Asp Gln Pro Thr Thr Asn
            180                 185                 190

Lys Gly Val Ala Trp Lys Val Glu Ala His Leu Ile Asn Asn Met Gly
        195                 200                 205

His Asp His Thr Arg Gln Leu Thr Asn Asp Ser Asp Arg Val Lys
    210                 215                 220

Ser Glu Ile Phe Ser Leu Thr Arg Asn Gly Asn Leu Trp Ala Lys Asp
225                 230                 235                 240

Asn Phe Thr Pro Lys Asn Lys Met Pro Val Thr Val Ser Glu Gly Phe
                245                 250                 255

Asn Pro Glu Phe Leu Ala Val Met Ser His Asp Lys Asp Glu Gly
            260                 265                 270

Lys Ser Lys Phe Val Val His Tyr Lys Arg Ser Met Asp Glu Phe Lys
        275                 280                 285

Ile Asp Trp Asn Lys His Gly Phe Trp Gly Tyr Trp Ser Gly Glu Asn
    290                 295                 300

His Val Asp Lys Lys Glu Glu Lys Leu Ser Ala Leu Tyr Glu Val Asp
305                 310                 315                 320

Trp Lys Thr His Asn Val Lys Phe Ile Lys Val Leu Asn Asp Lys Glu
                325                 330                 335

Lys Lys

<210> SEQ ID NO 19
<211> LENGTH: 339
<212> TYPE: PRT
<213> ORGANISM: Staphylococcus aureus

<400> SEQUENCE: 19

Met Ile Lys Gln Val Cys Lys Asn Ile Thr Ile Cys Ser Leu Ala Leu
1               5                   10                  15

Ser Thr Ala Leu Thr Val Phe Pro Ala Ser Ser Tyr Ala Glu Ile Lys
            20                  25                  30

Ser Lys Ile Thr Thr Val Ser Glu Lys Asn Leu Asp Gly Asp Thr Lys
            35                  40                  45

Met Tyr Thr Arg Thr Ala Thr Thr Ser Asp Thr Glu Lys Lys Ile Ser
50                  55                  60

Gln Ser Leu Gln Phe Asn Phe Leu Thr Glu Pro Asn Tyr Asp Lys Glu
65                  70                  75                  80

Thr Val Phe Ile Lys Ala Lys Gly Thr Ile Gly Ser Gly Leu Lys Ile
            85                  90                  95

Leu Asn Pro Asn Gly Tyr Trp Asn Ser Thr Leu Thr Trp Pro Gly Ser
            100                 105                 110

Tyr Ser Val Ser Ile Gln Asn Val Asp Asp Asn Asn Ser Thr Asn
            115                 120                 125

Val Thr Asp Phe Ala Pro Lys Asn Gln Asp Glu Ser Arg Glu Val Lys
130                 135                 140

Tyr Thr Tyr Gly Tyr Lys Thr Gly Gly Asp Phe Ser Ile Asn Arg Gly
145                 150                 155                 160

Gly Leu Thr Gly Asn Ile Thr Lys Glu Lys Asn Tyr Ser Glu Thr Ile
                165                 170                 175

Ser Tyr Gln Gln Pro Ser Tyr Arg Thr Leu Ile Asp Gln Pro Thr Thr
                180                 185                 190

Asn Lys Gly Val Ala Trp Lys Val Glu Ala His Ser Ile Asn Asn Met
            195                 200                 205

Gly His Asp His Thr Arg Gln Leu Thr Asn Asp Ser Asp Asp Arg Val
210                 215                 220

Lys Ser Glu Ile Phe Ser Leu Thr Arg Asn Gly Asn Leu Trp Ala Lys
225                 230                 235                 240

Asp Asn Phe Thr Pro Lys Asn Lys Met Pro Val Thr Val Ser Glu Gly
                245                 250                 255

Phe Asn Pro Glu Phe Leu Ala Val Met Ser His Asp Lys Asn Asp Lys
            260                 265                 270

Gly Lys Ser Arg Phe Ile Val His Tyr Lys Arg Ser Met Asp Asp Phe
            275                 280                 285

Lys Leu Asp Trp Asn Lys His Gly Phe Trp Gly Tyr Trp Ser Gly Glu
            290                 295                 300

Asn His Val Asp Gln Lys Glu Glu Lys Leu Ser Ala Leu Tyr Glu Val
305                 310                 315                 320

Asp Trp Lys Thr His Asp Val Lys Leu Ile Lys Thr Ile Asn Asp Lys
            325                 330                 335

Glu Gln Lys

<210> SEQ ID NO 20
<211> LENGTH: 338
<212> TYPE: PRT
<213> ORGANISM: Staphylococcus aureus

<400> SEQUENCE: 20

Met Ile Lys Gln Leu Cys Lys Asn Ile Thr Ile Cys Thr Leu Ala Leu
1               5                   10                  15

Ser Thr Thr Phe Thr Val Leu Pro Ala Thr Ser Phe Ala Lys Ile Asn
            20                  25                  30

```
Ser Glu Ile Lys Gln Val Ser Glu Lys Asn Leu Asp Gly Asp Thr Lys
            35                  40                  45

Met Tyr Thr Arg Thr Ala Thr Thr Ser Asp Ser Gln Lys Asn Ile Thr
 50                  55                  60

Gln Ser Leu Gln Phe Asn Phe Leu Thr Glu Pro Asn Tyr Asp Lys Glu
 65                  70                  75                  80

Thr Val Phe Ile Lys Ala Lys Gly Thr Ile Gly Ser Gly Leu Arg Ile
                 85                  90                  95

Leu Asp Pro Asn Gly Tyr Trp Asn Ser Thr Leu Arg Trp Pro Gly Ser
                100                 105                 110

Tyr Ser Val Ser Ile Gln Asn Val Asp Asn Asn Thr Asn Val
                115                 120                 125

Thr Asp Phe Ala Pro Lys Asn Gln Asp Glu Ser Arg Glu Val Lys Tyr
            130                 135                 140

Thr Tyr Gly Tyr Lys Thr Gly Gly Asp Phe Ser Ile Asn Arg Gly Gly
145                 150                 155                 160

Leu Thr Gly Asn Ile Thr Lys Glu Ser Asn Tyr Ser Glu Thr Ile Ser
                165                 170                 175

Tyr Gln Gln Pro Ser Tyr Arg Thr Leu Leu Asp Gln Ser Thr Ser His
                180                 185                 190

Lys Gly Val Gly Trp Lys Val Glu Ala His Leu Ile Asn Asn Met Gly
            195                 200                 205

His Asp His Thr Arg Gln Leu Thr Asn Asp Ser Asp Asn Arg Thr Lys
            210                 215                 220

Ser Glu Ile Phe Ser Leu Thr Arg Asn Gly Asn Leu Trp Ala Lys Asp
225                 230                 235                 240

Asn Phe Thr Pro Lys Asp Lys Met Pro Val Thr Val Ser Glu Gly Phe
                245                 250                 255

Asn Pro Glu Phe Leu Ala Val Met Ser His Asp Lys Asp Lys Gly
                260                 265                 270

Lys Ser Gln Phe Val Val His Tyr Lys Arg Ser Met Asp Glu Phe Lys
            275                 280                 285

Ile Asp Trp Asn Arg His Gly Phe Trp Gly Tyr Trp Ser Gly Glu Asn
            290                 295                 300

His Val Asp Glu Lys Glu Glu Lys Leu Ser Ala Leu Tyr Glu Val Asp
305                 310                 315                 320

Trp Lys Thr His Asn Val Lys Phe Val Lys Val Leu Asn Asp Asn Glu
                325                 330                 335

Lys Lys

<210> SEQ ID NO 21
<211> LENGTH: 339
<212> TYPE: PRT
<213> ORGANISM: Staphylococcus aureus

<400> SEQUENCE: 21

Met Ile Lys Gln Val Cys Lys Asn Ile Thr Ile Cys Ser Leu Ala Leu
 1                   5                  10                  15

Ser Thr Ala Leu Thr Val Phe Pro Ala Ser Ser Tyr Ala Glu Ile Lys
                20                  25                  30

Ser Lys Ile Thr Thr Val Ser Glu Lys Asn Leu Asp Gly Asp Thr Lys
            35                  40                  45

Met Tyr Thr Arg Thr Ala Thr Thr Ser Asp Thr Glu Lys Lys Ile Ser
 50                  55                  60
```

-continued

Gln Ser Leu Gln Phe Asn Phe Leu Thr Glu Pro Asn Tyr Asp Lys Glu
 65                  70                  75                  80

Thr Val Phe Ile Lys Ala Lys Gly Thr Ile Gly Ser Gly Leu Lys Ile
             85                  90                  95

Leu Asn Pro Asn Gly Tyr Trp Asn Ser Thr Leu Arg Trp Pro Gly Ser
            100                 105                 110

Tyr Ser Val Ser Ile Gln Asn Val Asp Asp Asn Asn Ser Thr Asn
            115                 120                 125

Val Thr Asp Phe Ala Pro Lys Asn Gln Asp Glu Ser Arg Glu Val Lys
        130                 135                 140

Tyr Thr Tyr Gly Tyr Lys Thr Gly Gly Asp Phe Ser Ile Asn Arg Gly
145                 150                 155                 160

Gly Leu Thr Gly Asn Ile Thr Lys Glu Lys Asn Tyr Ser Glu Thr Ile
                165                 170                 175

Ser Tyr Gln Gln Pro Ser Tyr Arg Thr Leu Ile Asp Gln Pro Thr Thr
                180                 185                 190

Asn Lys Gly Val Ala Trp Lys Val Glu Ala His Ser Ile Asn Asn Met
            195                 200                 205

Gly His Asp His Thr Arg Gln Leu Thr Asn Asp Ser Asp Asp Arg Val
        210                 215                 220

Lys Ser Glu Ile Phe Ser Leu Thr Arg Asn Gly Asn Leu Trp Ala Lys
225                 230                 235                 240

Asp Asn Phe Thr Pro Lys Asn Lys Met Pro Val Thr Val Ser Glu Gly
                245                 250                 255

Phe Asn Pro Glu Phe Leu Ala Val Met Ser His Asp Lys Asn Asp Lys
            260                 265                 270

Gly Lys Ser Arg Phe Ile Val His Tyr Lys Arg Ser Met Asp Asp Phe
        275                 280                 285

Lys Leu Asp Trp Asn Lys His Gly Phe Trp Gly Tyr Trp Ser Gly Glu
            290                 295                 300

Asn His Val Asp Gln Lys Glu Glu Lys Leu Ser Ala Leu Tyr Glu Val
305                 310                 315                 320

Asp Trp Lys Thr His Asp Val Lys Leu Ile Lys Thr Ile Asn Asp Lys
                325                 330                 335

Glu Gln Lys

<210> SEQ ID NO 22
<211> LENGTH: 338
<212> TYPE: PRT
<213> ORGANISM: Staphylococcus aureus

<400> SEQUENCE: 22

Met Ile Lys Gln Leu Tyr Lys Asn Ile Thr Ile Cys Ser Leu Ala Ile
 1               5                  10                  15

Ser Thr Ala Leu Thr Val Phe Pro Ala Thr Ser Tyr Ala Lys Ile Asn
             20                  25                  30

Ser Glu Ile Lys Ala Val Ser Glu Lys Asn Leu Asp Gly Asp Thr Lys
         35                  40                  45

Met Tyr Thr Arg Thr Ala Thr Thr Ser Asp Ser Gln Lys Asn Ile Thr
     50                  55                  60

Gln Ser Leu Gln Phe Asn Phe Leu Thr Glu Pro Asn Tyr Asp Lys Glu
 65                  70                  75                  80

Thr Val Phe Ile Lys Ala Lys Gly Thr Ile Gly Ser Gly Leu Arg Ile
             85                  90                  95

```
Leu Asp Pro Asn Gly Tyr Trp Asn Ser Thr Leu Arg Trp Pro Gly Ser
            100                 105                 110

Tyr Ser Val Ser Ile Gln Asn Val Asp Asp Asn Asn Thr Asn Val
            115                 120                 125

Thr Asp Phe Ala Pro Lys Asn Gln Asp Glu Ser Arg Glu Val Lys Tyr
            130                 135                 140

Thr Tyr Gly Tyr Lys Thr Gly Gly Asp Phe Ser Ile Asn Arg Gly Gly
145                 150                 155                 160

Leu Thr Gly Asn Ile Thr Lys Glu Ser Asn Tyr Ser Glu Thr Ile Ser
                165                 170                 175

Tyr Gln Gln Pro Ser Tyr Arg Thr Leu Leu Asp Gln Ser Thr Ser His
            180                 185                 190

Lys Gly Val Gly Trp Lys Val Glu Ala His Leu Ile Asn Asn Met Gly
            195                 200                 205

His Asp His Thr Arg Gln Leu Thr Asn Asp Ser Asp Asn Arg Thr Lys
            210                 215                 220

Ser Glu Ile Phe Ser Leu Thr Arg Asn Gly Asn Leu Trp Ala Lys Asp
225                 230                 235                 240

Asn Phe Thr Pro Lys Asp Lys Met Pro Val Thr Val Ser Glu Gly Phe
                245                 250                 255

Asn Pro Glu Phe Leu Ala Val Met Ser His Asp Lys Lys Asp Lys Gly
            260                 265                 270

Lys Ser Gln Phe Val Val His Tyr Lys Arg Ser Met Asp Glu Phe Lys
            275                 280                 285

Ile Asp Trp Asn Arg His Gly Phe Trp Gly Tyr Trp Ser Gly Glu Asn
            290                 295                 300

His Val Asp Lys Lys Glu Glu Lys Leu Ser Ala Leu Tyr Glu Val Asp
305                 310                 315                 320

Trp Lys Thr His Asp Val Lys Phe Val Lys Val Leu Asn Asp Asn Glu
                325                 330                 335

Lys Lys

<210> SEQ ID NO 23
<211> LENGTH: 338
<212> TYPE: PRT
<213> ORGANISM: Staphylococcus aureus

<400> SEQUENCE: 23

Met Ile Lys Gln Leu Tyr Lys Asn Ile Thr Ile Cys Thr Leu Ala Leu
1               5                   10                  15

Ser Thr Thr Phe Thr Val Leu Pro Ala Thr Ser Tyr Ala Lys Ile Asn
            20                  25                  30

Ser Glu Ile Lys Ala Val Ser Glu Lys Asn Leu Asp Gly Asp Thr Lys
            35                  40                  45

Met Tyr Thr Arg Thr Ala Thr Thr Ser Asp Ser Gln Lys Asn Ile Thr
        50                  55                  60

Gln Ser Leu Gln Phe Asn Phe Leu Thr Glu Pro Asn Tyr Asp Lys Glu
65                  70                  75                  80

Thr Val Phe Ile Lys Ala Lys Gly Thr Ile Gly Ser Gly Leu Arg Ile
                85                  90                  95

Leu Asp Pro Asn Gly Tyr Trp Asn Ser Thr Leu Arg Trp Pro Gly Ser
            100                 105                 110

Tyr Ser Val Ser Ile Gln Asn Val Asp Asp Asn Asn Thr Asn Val
            115                 120                 125
```

Thr Asp Phe Ala Pro Lys Asn Gln Asp Glu Ser Arg Glu Val Lys Tyr
            130                 135                 140

Thr Tyr Gly Tyr Lys Thr Gly Gly Asp Phe Ser Ile Asn Arg Gly Gly
145                 150                 155                 160

Leu Thr Gly Asn Ile Thr Lys Glu Ser Asn Tyr Ser Glu Thr Ile Ser
                165                 170                 175

Tyr Gln Gln Pro Ser Tyr Arg Thr Leu Leu Asp Gln Ser Thr Ser His
            180                 185                 190

Lys Gly Val Gly Trp Lys Val Glu Ala His Leu Ile Asn Asn Met Gly
        195                 200                 205

His Asp His Thr Arg Gln Leu Thr Asn Asp Ser Asp Asn Arg Thr Lys
210                 215                 220

Ser Glu Ile Phe Ser Leu Thr Arg Asn Gly Asn Leu Trp Ala Lys Asp
225                 230                 235                 240

Asn Phe Thr Pro Lys Asn Lys Met Pro Val Thr Val Ser Glu Gly Phe
                245                 250                 255

Asn Pro Glu Phe Leu Ala Val Met Ser His Asp Lys Lys Asp Glu Gly
            260                 265                 270

Lys Ser Lys Phe Val Val His Tyr Lys Arg Ser Met Asp Glu Phe Lys
        275                 280                 285

Ile Asp Trp Asn Arg His Gly Phe Trp Gly Tyr Trp Ser Gly Glu Asn
290                 295                 300

His Val Asp Lys Lys Glu Glu Lys Leu Ser Ala Leu Tyr Glu Val Asp
305                 310                 315                 320

Trp Lys Thr His Asn Val Lys Phe Val Lys Val Leu Asn Asp Asn Glu
                325                 330                 335

Lys Lys

<210> SEQ ID NO 24
<211> LENGTH: 338
<212> TYPE: PRT
<213> ORGANISM: Staphylococcus aureus

<400> SEQUENCE: 24

Met Ile Lys Gln Leu Tyr Lys Asn Ile Thr Ile Cys Ser Leu Thr Ile
1               5                   10                  15

Ser Thr Ala Leu Thr Val Phe Pro Ala Thr Ser Tyr Ala Lys Ile Asn
            20                  25                  30

Ser Glu Ile Lys Ala Val Ser Glu Lys Asn Leu Asp Gly Asp Thr Lys
        35                  40                  45

Met Tyr Thr Arg Thr Ala Thr Thr Ser Asp Ser Gln Lys Asn Ile Thr
50                  55                  60

Gln Ser Leu Gln Phe Asn Phe Leu Thr Glu Pro Asn Tyr Asp Lys Glu
65                  70                  75                  80

Thr Val Phe Ile Lys Ala Lys Gly Thr Ile Gly Ser Gly Leu Arg Ile
                85                  90                  95

Leu Asp Pro Asn Gly Tyr Trp Asn Ser Thr Leu Arg Trp Pro Gly Ser
            100                 105                 110

Tyr Ser Val Ser Ile Gln Asn Val Asp Asp Asn Asn Thr Asn Val
        115                 120                 125

Thr Asp Phe Ala Pro Lys Asn Gln Asp Glu Ser Arg Glu Val Lys Tyr
130                 135                 140

Thr Tyr Gly Tyr Lys Thr Gly Gly Asp Phe Ser Ile Asn Arg Gly Gly
145                 150                 155                 160

-continued

Leu Pro Gly Asn Ile Thr Lys Glu Ser Asn Tyr Ser Glu Thr Ile Ser
                165                 170                 175

Tyr Gln Gln Pro Ser Tyr Arg Thr Leu Leu Asp Gln Ser Thr Ser His
            180                 185                 190

Lys Gly Val Gly Trp Lys Val Glu Ala His Leu Ile Asn Asn Met Gly
        195                 200                 205

His Asp His Thr Arg Gln Leu Thr Asn Asp Ser Asp Asn Arg Thr Lys
    210                 215                 220

Ser Glu Ile Phe Ser Leu Thr Arg Asn Gly Asn Leu Trp Ala Lys Asp
225                 230                 235                 240

Asn Phe Thr Pro Lys Asn Lys Met Pro Val Thr Val Ser Glu Gly Phe
                245                 250                 255

Asn Pro Glu Phe Leu Ala Val Met Ser His Asp Lys Lys Asp Glu Gly
            260                 265                 270

Lys Ser Lys Phe Val Val His Tyr Lys Arg Ser Met Asp Glu Phe Lys
        275                 280                 285

Ile Asp Trp Asn Arg His Gly Phe Trp Gly Tyr Trp Ser Gly Glu Asn
    290                 295                 300

His Val Asp Lys Lys Glu Glu Lys Leu Ser Ala Leu Tyr Glu Val Asp
305                 310                 315                 320

Trp Lys Thr His Asp Val Lys Phe Val Lys Val Leu Asn Asp Asn Glu
                325                 330                 335

Lys Lys

<210> SEQ ID NO 25
<211> LENGTH: 338
<212> TYPE: PRT
<213> ORGANISM: Staphylococcus aureus

<400> SEQUENCE: 25

Met Ile Lys Gln Leu Cys Lys Asn Ile Thr Ile Cys Thr Leu Ala Leu
1               5                   10                  15

Ser Thr Thr Phe Thr Val Leu Pro Ala Thr Ser Phe Ala Lys Ile Asn
                20                  25                  30

Ser Glu Ile Lys Gln Val Ser Glu Lys Asn Leu Asp Gly Asp Thr Lys
            35                  40                  45

Met Tyr Thr Arg Thr Ala Thr Thr Ser Asp Ser Gln Lys Asn Ile Thr
        50                  55                  60

Gln Ser Leu Gln Phe Asn Phe Leu Thr Glu Pro Asn Tyr Asp Lys Glu
65                  70                  75                  80

Thr Val Phe Ile Lys Ala Lys Gly Thr Ile Gly Ser Gly Leu Arg Ile
                85                  90                  95

Leu Asp Pro Asn Gly Tyr Trp Asn Ser Thr Leu Arg Trp Pro Gly Ser
            100                 105                 110

Tyr Ser Val Ser Ile Gln Asn Val Asp Asp Asn Asn Thr Asn Val
        115                 120                 125

Thr Asp Phe Ala Pro Lys Asn Gln Asp Glu Ser Arg Glu Val Lys Tyr
    130                 135                 140

Thr Tyr Gly Tyr Lys Thr Gly Gly Asp Phe Ser Ile Asn Arg Gly Gly
145                 150                 155                 160

Leu Thr Gly Asn Ile Thr Lys Glu Ser Asn Tyr Ser Glu Thr Ile Ser
                165                 170                 175

Tyr Gln Gln Pro Ser Tyr Arg Thr Leu Leu Asp Gln Ser Thr Ser His
            180                 185                 190

```
Lys Gly Val Gly Trp Lys Val Glu Ala His Leu Ile Asn Asn Met Gly
            195                 200                 205

His Asp His Thr Arg Gln Leu Thr Asn Asp Ser Asp Asn Arg Thr Lys
    210                 215                 220

Ser Glu Ile Phe Ser Leu Thr Arg Asn Gly Asn Leu Trp Ala Lys Asp
225                 230                 235                 240

Asn Phe Thr Pro Lys Asn Lys Met Pro Val Thr Val Ser Glu Gly Phe
                245                 250                 255

Asn Pro Glu Phe Leu Ala Val Met Ser His Asp Lys Lys Asp Glu Gly
            260                 265                 270

Lys Ser Lys Phe Val Val His Tyr Lys Arg Ser Met Asp Glu Phe Lys
        275                 280                 285

Ile Asp Trp Asn Arg His Gly Phe Trp Gly Tyr Trp Ser Gly Glu Asn
    290                 295                 300

His Val Asp Lys Lys Glu Glu Lys Leu Ser Ala Leu Tyr Glu Val Asp
305                 310                 315                 320

Trp Lys Thr His Asn Val Lys Phe Val Lys Val Leu Asn Asp Asn Glu
                325                 330                 335

Lys Lys

<210> SEQ ID NO 26
<211> LENGTH: 338
<212> TYPE: PRT
<213> ORGANISM: Staphylococcus aureus

<400> SEQUENCE: 26

Met Ile Lys Gln Leu Cys Lys Asn Ile Thr Ile Cys Thr Leu Ala Leu
1               5                   10                  15

Ser Thr Thr Phe Thr Val Leu Pro Ala Thr Ser Phe Ala Lys Ile Asn
            20                  25                  30

Ser Glu Ile Lys Gln Val Ser Glu Lys Asn Leu Asp Gly Asp Thr Lys
        35                  40                  45

Met Tyr Thr Arg Thr Ala Thr Thr Ser Asp Ser Gln Lys Asn Ile Thr
    50                  55                  60

Gln Ser Leu Gln Phe Asn Phe Leu Thr Glu Pro Asn Tyr Asp Lys Glu
65                  70                  75                  80

Thr Val Phe Ile Lys Ala Lys Gly Thr Ile Gly Ser Gly Leu Arg Ile
                85                  90                  95

Leu Asp Pro Asn Gly Tyr Trp Asn Ser Thr Leu Arg Trp Pro Gly Ser
            100                 105                 110

Tyr Ser Val Ser Ile Gln Asn Val Asp Asp Asn Asn Thr Asn Val
        115                 120                 125

Thr Asp Phe Ala Pro Lys Asn Gln Asp Glu Ser Arg Glu Val Lys Tyr
    130                 135                 140

Thr Tyr Gly Tyr Lys Thr Gly Gly Asp Phe Ser Ile Asn Arg Gly Gly
145                 150                 155                 160

Leu Thr Gly Asn Ile Thr Lys Glu Ser Asn Tyr Ser Glu Thr Ile Ser
                165                 170                 175

Tyr Gln Gln Pro Ser Tyr Arg Thr Leu Leu Asp Gln Ser Thr Ser His
            180                 185                 190

Lys Gly Val Gly Trp Lys Val Glu Ala His Leu Ile Asn Asn Met Gly
        195                 200                 205

His Asp His Thr Arg Gln Leu Thr Asn Asp Ser Asp Asn Arg Thr Lys
    210                 215                 220
```

```
Ser Glu Ile Phe Ser Leu Thr Arg Asn Gly Asn Leu Trp Ala Lys Asp
225                 230                 235                 240

Asn Phe Thr Pro Lys Asp Lys Met Pro Val Thr Val Ser Glu Gly Phe
                245                 250                 255

Asn Pro Glu Phe Leu Ala Val Met Ser His Asp Lys Lys Asp Lys Gly
            260                 265                 270

Lys Ser Gln Phe Val Val His Tyr Lys Arg Ser Met Asp Glu Phe Lys
        275                 280                 285

Ile Asp Trp Asn Arg His Gly Phe Trp Gly Tyr Trp Ser Gly Glu Asn
    290                 295                 300

His Val Asp Lys Lys Glu Lys Leu Ser Ala Leu Tyr Glu Val Asp
305                 310                 315                 320

Trp Lys Thr His Asn Val Lys Phe Val Lys Val Leu Asn Asp Asn Glu
                325                 330                 335

Lys Lys

<210> SEQ ID NO 27
<211> LENGTH: 338
<212> TYPE: PRT
<213> ORGANISM: Staphylococcus aureus

<400> SEQUENCE: 27

Met Ile Lys Gln Leu Cys Lys Asn Ile Thr Ile Cys Thr Leu Ala Leu
1               5                   10                  15

Ser Thr Thr Phe Thr Val Leu Pro Ala Thr Ser Phe Ala Lys Ile Asn
                20                  25                  30

Ser Glu Ile Lys Gln Val Ser Glu Lys Asn Leu Asp Gly Asp Thr Lys
            35                  40                  45

Met Tyr Thr Arg Thr Ala Thr Thr Ser Asp Ser Gln Lys Asn Ile Thr
    50                  55                  60

Gln Ser Leu Gln Phe Asn Phe Leu Thr Glu Pro Asn Tyr Asp Lys Glu
65                  70                  75                  80

Thr Val Phe Ile Lys Ala Lys Gly Thr Ile Gly Ser Gly Leu Arg Ile
                85                  90                  95

Leu Asp Pro Asn Gly Tyr Trp Asn Ser Thr Leu Arg Trp Pro Gly Ser
                100                 105                 110

Tyr Ser Val Ser Ile Gln Asn Val Asp Asp Asn Asn Thr Asn Val
            115                 120                 125

Thr Asp Phe Ala Pro Lys Asn Gln Asp Glu Ser Arg Glu Val Lys Tyr
    130                 135                 140

Thr Tyr Gly Tyr Lys Thr Gly Gly Asp Phe Ser Ile Asn Arg Gly Gly
145                 150                 155                 160

Leu Thr Gly Asn Ile Thr Lys Glu Ser Asn Tyr Ser Glu Thr Ile Ser
                165                 170                 175

Tyr Gln Gln Pro Ser Tyr Arg Thr Leu Leu Asp Gln Ser Thr Ser His
            180                 185                 190

Lys Gly Val Gly Trp Lys Val Glu Ala His Leu Ile Asn Asn Met Gly
        195                 200                 205

His Asp His Thr Arg Gln Leu Thr Asn Asp Ser Asp Asn Arg Thr Lys
    210                 215                 220

Ser Glu Ile Phe Ser Leu Thr Arg Asn Gly Asn Leu Trp Ala Lys Asp
225                 230                 235                 240

Asn Phe Thr Pro Lys Asp Lys Met Pro Val Thr Val Ser Glu Gly Phe
                245                 250                 255
```

```
Asn Pro Glu Phe Leu Ala Val Met Ser His Asp Lys Asp Lys Gly
            260                 265                 270

Lys Ser Gln Phe Val Val His Tyr Lys Arg Ser Met Asp Glu Phe Lys
                275                 280                 285

Ile Asp Trp Asn Arg His Gly Phe Trp Gly Tyr Trp Ser Gly Glu Asn
290                 295                 300

His Val Asp Lys Lys Glu Glu Lys Leu Ser Ala Leu Tyr Glu Val Asp
305                 310                 315                 320

Trp Lys Thr His Asn Val Lys Phe Val Lys Val Leu Asn Asp Asn Glu
                325                 330                 335

Lys Lys

<210> SEQ ID NO 28
<211> LENGTH: 1056
<212> TYPE: DNA
<213> ORGANISM: Staphylococcus aureus

<400> SEQUENCE: 28
atgaaaaata aaaacgtgt tttaatagcg tcatcattat catgtgcaat tttattgtta      60
tcagcagcaa cgactcaagc aaattcagct cataaagact ctcaagacca aaataagaaa    120
gaacatgttg ataagtctca acaaaaagac aaacgtaatg ttactaataa agataaaaat    180
tcaacagcac cggatgatat tgggaaaaac ggtaaaatca caaaacgaac tgaaacagta    240
tatgatgaga aaacaaatat actccaaaat ttacaattcg actttatcga tgatccaact    300
tatgacaaga atgtattact tgttaaaaaa caaggctcaa ttcattcaaa tttaaagttt    360
gaatctcata agaagaaaa aaattcaaat tggttaaagt atccaagtga gtaccatgta    420
gattttcaag taaaagaaa tcgtaaaact gaaatattag accaattgcc gaaaaataaa    480
atttcaactg caaagtaga cagtacattt tcatatagct caggtggtaa attcgattca    540
acaaaaggta ttggacgaac ttcatcaaat agctactcca aaacgattag ttataatcag    600
caaaattatg acacaattgc cagcggtaaa aataataact ggcatgtaca ctggtcagtt    660
attgcgaatg acttgaagta tggtggagaa gtgaaaaata gaaatgatga attattattc    720
tatagaaata cgagaattgc tactgtagaa aaccctgaac taagctttgc ttcaaaatat    780
agatacccag cattagtaag aagtggcttt aatccagaat ttttaactta tttatctaat    840
gaaaagtcaa atgagaaaac gcaatttgaa gtaacataca cacgaaatca agatattttg    900
aaaaacagac ctggaataca ttatgcacct ccaattttag aaaaaaataa agatggtcaa    960
agattaattg tcacttatga agttgattgg aaaaataaaa cagttaaagt cgttgataaa   1020
tattctgatg acaataaacc ttataaagaa ggataa                              1056

<210> SEQ ID NO 29
<211> LENGTH: 1017
<212> TYPE: DNA
<213> ORGANISM: Staphylococcus aureus

<400> SEQUENCE: 29
atgattaaac aactatgtaa aaatatcaca atttgtacgt tagcactatc gactactttc      60
actgtattac cagctacttc atttgcaaag attaattctg aaatcaaaca gtttctgag    120 aagaatcttg atggtgatac taaaatgtat acacgtacag ctacaacaag tgatagtcaa    180
aaaaatatta ctcaaagctt acaatttaat ttccttaactg aacctaatta tgataaagaa   240 acagtatttta ttaaagcaaa aggtacaatt ggtagtggtt tgagaatttt agacccaaat   300
```

```
ggttattgga atagtacatt aagatggcct ggatcttatt cagtttcaat tcaaaatgtt    360
gatgacaaca acaatacaaa tgtgactgac tttgcaccaa aaaatcagga tgaatcaaga    420
gaagttaaat atacgtatgg ttataaaaca ggtggagatt tttcgattaa tcgtggaggc    480
ttaactggaa atattacaaa agagagtaat tattcagaga cgattagtta tcaacaacca    540
tcatatcgta cattacttga tcaatctacg tcacataaag gtgtaggttg aaagtagaa    600 gcacatttga taaataatat gggacatgac catacgagac aattaactaa tgatagtgat    660
aatagaacta aaagtgaaat tttttcttta acacgaaatg gaaatttatg ggcgaaagat    720
aatttcacac ctaaagacaa aatgcctgta actgtgtctg aagggtttaa tccagaattt    780
ttagctgtta tgtcacatga taaaaaagac aaaggtaaat cacaatttgt tgttcattat    840
aaaagatcaa tggatgagtt taaaatagat tggaatcgcc atggtttctg gggctattgg    900
tctggtgaaa accatgtaga taaaaaagaa gaaaaattat cagcattata tgaagttgat    960
tggaagacac ataatgtgaa gtttgtaaaa gtacttaatg ataatgaaaa gaaataa      1017
```

<210> SEQ ID NO 30  
<211> LENGTH: 36  
<212> TYPE: DNA  
<213> ORGANISM: Artificial Sequence  
<220> FEATURE:  
<223> OTHER INFORMATION: Synthetic Primer

<400> SEQUENCE: 30

```
cccgtcgact tatccttctt tataaggttt attgtc                              36
```

<210> SEQ ID NO 31  
<211> LENGTH: 54  
<212> TYPE: DNA  
<213> ORGANISM: Artificial Sequence  
<220> FEATURE:  
<223> OTHER INFORMATION: Synthetic Primer

<400> SEQUENCE: 31

```
cccgaaggat ttcacatcat catcatcatc acaattcagc tcataaagac tctc          54
```

<210> SEQ ID NO 32  
<211> LENGTH: 58  
<212> TYPE: DNA  
<213> ORGANISM: Artificial Sequence  
<220> FEATURE:  
<223> OTHER INFORMATION: Synthetic Primer

<400> SEQUENCE: 32

```
ccccgaagga tttcacatca tcatcatcat cacaagatta attctgaaat caaacaag      58
```

<210> SEQ ID NO 33  
<211> LENGTH: 38  
<212> TYPE: DNA  
<213> ORGANISM: Artificial Sequence  
<220> FEATURE:  
<223> OTHER INFORMATION: Synthetic Primer

<400> SEQUENCE: 33

```
cccgtcgact tatttctttt cattatcatt aagtactt                            38
```

<210> SEQ ID NO 34  
<211> LENGTH: 35  
<212> TYPE: DNA  
<213> ORGANISM: Artificial Sequence  
<220> FEATURE:

<223> OTHER INFORMATION: Synthetic Primer

<400> SEQUENCE: 34 cccccctcgag aattcagctc ataaagactc tcaag        35

<210> SEQ ID NO 35
<211> LENGTH: 37
<212> TYPE: DNA
<213> ORGANISM: Artificial Sequence
<220> FEATURE:
<223> OTHER INFORMATION: Synthetic Primer

<400> SEQUENCE: 35
ccccggatcc ttatccttct ttataaggtt tattgtc        37

<210> SEQ ID NO 36
<211> LENGTH: 36
<212> TYPE: DNA
<213> ORGANISM: Artificial Sequence
<220> FEATURE:
<223> OTHER INFORMATION: Synthetic Primer

<400> SEQUENCE: 36
ccccggatcc ttaatattta tcaacgactt taactg        36

<210> SEQ ID NO 37
<211> LENGTH: 32
<212> TYPE: DNA
<213> ORGANISM: Artificial Sequence
<220> FEATURE:
<223> OTHER INFORMATION: Synthetic Primer

<400> SEQUENCE: 37 cccccctcgag tcaacagcac cggatgatat tg        32

<210> SEQ ID NO 38
<211> LENGTH: 35
<212> TYPE: DNA
<213> ORGANISM: Artificial Sequence
<220> FEATURE:
<223> OTHER INFORMATION: Synthetic Primer

<400> SEQUENCE: 38 cccccctcgag aagattaatt ctgaaatcaa acaag        35

<210> SEQ ID NO 39
<211> LENGTH: 40
<212> TYPE: DNA
<213> ORGANISM: Artificial Sequence
<220> FEATURE:
<223> OTHER INFORMATION: Synthetic Primer

<400> SEQUENCE: 39
ccccggatcc ttatttcttt tcattatcat taagtactttt        40

<210> SEQ ID NO 40
<211> LENGTH: 33
<212> TYPE: DNA
<213> ORGANISM: Artificial Sequence
<220> FEATURE:
<223> OTHER INFORMATION: Synthetic Primer

<400> SEQUENCE: 40
gggcatatga attcagctca taaagactct caa        33

```
<210> SEQ ID NO 41
<211> LENGTH: 33
<212> TYPE: DNA
<213> ORGANISM: Artificial Sequence
<220> FEATURE:
<223> OTHER INFORMATION: Synthetic Primer

<400> SEQUENCE: 41
cccgtcgact ccttctttat aaggtttatt gtc                                    33

<210> SEQ ID NO 42
<211> LENGTH: 34
<212> TYPE: DNA
<213> ORGANISM: Artificial Sequence
<220> FEATURE:
<223> OTHER INFORMATION: Synthetic Primer

<400> SEQUENCE: 42
gggcatatga agattaattc tgaaatcaaa caag                                   34

<210> SEQ ID NO 43
<211> LENGTH: 35
<212> TYPE: DNA
<213> ORGANISM: Artificial Sequence
<220> FEATURE:
<223> OTHER INFORMATION: Synthetic Primer

<400> SEQUENCE: 43
cccgtcgact ttcttttcat tatcattaag tactt                                  35

<210> SEQ ID NO 44
<211> LENGTH: 279
<212> TYPE: PRT
<213> ORGANISM: Staphylococcus aureus
<220> FEATURE:
<221> NAME/KEY: MISC_FEATURE
<222> LOCATION: (1)..(279)
<223> OTHER INFORMATION: Xaa can be any naturally occuring amino acid

<400> SEQUENCE: 44
```

Xaa Asn Asn Ile Glu Asp Ile Gly Xaa Gly Ala Glu Ile Ile Lys Arg
1               5                   10                  15

Thr Glu Asp Val Xaa Ser Lys Lys Trp Gly Val Thr Gln Asn Ile Gln
            20                  25                  30

Phe Asp Phe Val Lys Asp Lys Tyr Asn Lys Asp Ala Leu Ile Val
        35                  40                  45

Lys Met Gln Gly Phe Ile Xaa Ser Arg Thr Thr Tyr Xaa Xaa Tyr Lys
50                  55                  60

Lys Xaa Xaa His Ile Lys Xaa Met Xaa Trp Pro Phe Gln Tyr Asn Ile
65                  70                  75                  80

Gly Leu Lys Thr Lys Asp Pro Asn Val Xaa Leu Ile Asn Tyr Leu Pro
            85                  90                  95

Lys Asn Lys Ile Xaa Ser Xaa Xaa Val Ser Gln Thr Leu Gly Tyr Asn
            100                 105                 110

Ile Gly Gly Asn Phe Gln Ser Ala Pro Ser Ile Gly Gly Asn Gly Ser
        115                 120                 125

Phe Asn Tyr Ser Lys Thr Ile Ser Tyr Asn Gln Gln Asn Tyr Val Ser
130                 135                 140

Glu Val Glu Lys Gln Asn Ser Lys Ser Val Lys Trp Gly Val Lys Ala
145                 150                 155                 160

Asn Ser Phe Val Thr Pro Xaa Gly Xaa Lys Ser Ala His Asp Xaa Tyr
            165                 170                 175

```
Leu Phe Val Xaa Xaa Lys Pro Xaa Xaa Pro Asn Pro Arg Asp Tyr Phe
                180                 185                 190

Val Pro Asp Asn Xaa Leu Pro Pro Leu Val Gln Ser Gly Glu Asn Pro
            195                 200                 205

Ser Phe Ile Thr Thr Leu Ser His Glu Lys Gly Ser Xaa Asp Thr Ser
    210                 215                 220

Glu Phe Glu Ile Thr Tyr Gly Arg Asn Met Asp Xaa Thr Xaa Ala Thr
225                 230                 235                 240

Xaa Arg Xaa His Tyr Leu Xaa Gly Xaa Arg Lys His Asn Ala Glu Val
                245                 250                 255

Asn Arg Asn Tyr Thr Val Lys Tyr Glu Val Asn Trp Lys Thr His Glu
            260                 265                 270

Ile Lys Val Lys Gly His Asn
        275

<210> SEQ ID NO 45
<211> LENGTH: 280
<212> TYPE: PRT
<213> ORGANISM: Staphylococcus aureus

<400> SEQUENCE: 45

Glu Asn Lys Ile Glu Asp Ile Gly Gln Gly Ala Glu Ile Ile Lys Arg
1               5                   10                  15

Thr Gln Asp Thr Thr Ser Lys Arg Leu Ala Ile Thr Gln Asn Ile Gln
            20                  25                  30

Phe Asp Phe Val Lys Asp Lys Lys Tyr Asn Lys Asp Ala Leu Val Val
            35                  40                  45

Lys Met Gln Gly Phe Ile Ser Ser Arg Thr Thr Tyr Ser Asp Leu Lys
50                  55                  60

Lys Tyr Pro Tyr Ile Lys Arg Met Ile Trp Pro Phe Gln Tyr Asn Ile
65                  70                  75                  80

Ser Leu Lys Thr Lys Asp Ser Asn Val Asp Leu Ile Asn Tyr Leu Pro
                85                  90                  95

Lys Asn Lys Ile Asp Ser Ala Asp Val Ser Gln Lys Leu Gly Tyr Asn
            100                 105                 110

Ile Gly Gly Asn Phe Gln Ser Ala Pro Ser Ile Gly Gly Asn Gly Ser
            115                 120                 125

Phe Asn Tyr Ser Lys Thr Ile Ser Tyr Asn Gln Lys Asn Tyr Val Thr
    130                 135                 140

Glu Val Glu Ser Gln Asn Ser Lys Gly Val Lys Trp Gly Val Lys Ala
145                 150                 155                 160

Asn Ser Phe Val Thr Pro Asn Gly Gln Val Ser Ala Tyr Asp Gln Tyr
                165                 170                 175

Leu Phe Ala Gln Asp Pro Thr Gly Pro Ala Ala Arg Asp Tyr Phe Val
                180                 185                 190

Pro Asp Asn Gln Leu Pro Pro Leu Ile Gln Ser Gly Phe Asn Pro Ser
            195                 200                 205

Phe Ile Thr Thr Leu Ser His Glu Arg Gly Lys Gly Asp Lys Ser Glu
    210                 215                 220

Phe Glu Ile Thr Tyr Gly Arg Asn Met Asp Ala Thr Tyr Ala Tyr Val
225                 230                 235                 240

Thr Arg His Arg Leu Ala Val Asp Arg Lys His Asp Ala Phe Lys Asn
                245                 250                 255

Arg Asn Val Thr Val Lys Tyr Glu Val Asn Trp Lys Thr His Glu Val
```

Lys Ile Lys Ser Ile Thr Pro Lys
            275                 280

<210> SEQ ID NO 46
<211> LENGTH: 286
<212> TYPE: PRT
<213> ORGANISM: Staphylococcus aureus

<400> SEQUENCE: 46

Ala Asn Asp Thr Glu Asp Ile Gly Lys Gly Ser Asp Ile Glu Ile Ile
1               5                   10                  15

Lys Arg Thr Glu Asp Lys Thr Ser Asn Lys Trp Gly Val Thr Gln Asn
            20                  25                  30

Ile Gln Phe Asp Phe Val Lys Asp Lys Tyr Asn Lys Asp Ala Leu
        35                  40                  45

Ile Leu Lys Met Gln Gly Phe Ile Ser Ser Arg Thr Thr Tyr Tyr Asn
50                  55                  60

Tyr Lys Lys Thr Asn His Val Lys Ala Met Arg Trp Pro Phe Gln Tyr
65                  70                  75                  80

Asn Ile Gly Leu Lys Thr Asn Asp Lys Tyr Val Ser Leu Ile Asn Tyr
                85                  90                  95

Leu Pro Lys Asn Lys Ile Glu Ser Thr Asn Val Ser Gln Thr Leu Gly
            100                 105                 110

Tyr Asn Ile Gly Gly Asn Phe Gln Ser Ala Pro Ser Leu Gly Gly Asn
        115                 120                 125

Gly Ser Phe Asn Tyr Ser Lys Ser Ile Ser Tyr Thr Gln Gln Asn Tyr
130                 135                 140

Val Ser Glu Val Glu Gln Gln Asn Ser Lys Ser Val Leu Trp Gly Val
145                 150                 155                 160

Lys Ala Asn Ser Phe Ala Thr Glu Ser Gly Gln Lys Ser Ala Phe Asp
                165                 170                 175

Ser Asp Leu Phe Val Gly Tyr Lys Pro His Ser Lys Asp Pro Arg Asp
            180                 185                 190

Tyr Phe Val Pro Asp Ser Glu Leu Pro Pro Leu Val Gln Ser Gly Phe
        195                 200                 205

Asn Pro Ser Phe Ile Ala Thr Val Ser His Glu Lys Gly Ser Ser Asp
210                 215                 220

Thr Ser Glu Phe Glu Ile Thr Tyr Gly Arg Asn Met Asp Val Thr His
225                 230                 235                 240

Ala Ile Lys Arg Ser Thr His Tyr Gly Asn Ser Tyr Leu Asp Gly His
                245                 250                 255

Arg Val His Asn Ala Phe Val Asn Arg Asn Tyr Thr Val Lys Tyr Glu
            260                 265                 270

Val Asn Trp Lys Thr His Glu Ile Lys Val Lys Gly Gln Asn
        275                 280                 285

<210> SEQ ID NO 47
<211> LENGTH: 283
<212> TYPE: PRT
<213> ORGANISM: Staphylococcus aureus

<400> SEQUENCE: 47

Asn Thr Asn Ile Glu Asn Ile Gly Asp Gly Ala Glu Val Ile Lys Arg
1               5                   10                  15

Thr Glu Asp Val Ser Ser Lys Lys Trp Gly Val Thr Gln Asn Val Gln

```
                20                  25                  30
Phe Asp Phe Val Lys Asp Lys Tyr Asn Lys Asp Ala Leu Ile Val
            35                  40                  45
Lys Met Gln Gly Phe Ile Asn Ser Arg Thr Ser Phe Ser Asp Val Lys
        50                  55                  60
Gly Ser Gly Tyr Glu Leu Thr Lys Arg Met Ile Trp Pro Phe Gln Tyr
65                  70                  75                  80
Asn Ile Gly Leu Thr Thr Lys Asp Pro Asn Val Ser Leu Ile Asn Tyr
                85                  90                  95
Leu Pro Lys Asn Lys Ile Glu Thr Thr Asp Val Gly Gln Thr Leu Gly
            100                 105                 110
Tyr Asn Ile Gly Gly Asn Phe Gln Ser Ala Pro Ser Ile Gly Gly Asn
        115                 120                 125
Gly Ser Phe Asn Tyr Ser Lys Thr Ile Ser Tyr Thr Gln Lys Ser Tyr
    130                 135                 140
Val Ser Glu Val Asp Lys Gln Asn Ser Lys Ser Val Lys Val Gly Val
145                 150                 155                 160
Lys Ala Asn Glu Phe Val Thr Pro Asp Gly Lys Lys Ser Ala His Asp
                165                 170                 175
Arg Tyr Leu Phe Val Gln Ser Pro Asn Gly Pro Thr Gly Ser Ala Arg
            180                 185                 190
Glu Tyr Phe Ala Pro Asp Asn Gln Leu Pro Pro Leu Val Gln Ser Gly
        195                 200                 205
Glu Asn Pro Ser Phe Ile Thr Thr Leu Ser His Glu Lys Gly Ser Ser
    210                 215                 220
Asp Thr Ser Glu Phe Glu Ile Ser Tyr Gly Arg Asn Leu Asp Ile Thr
225                 230                 235                 240
Tyr Ala Thr Leu Phe Pro Arg Thr Gly Ile Tyr Ala Glu Arg Lys His
                245                 250                 255
Asn Ala Phe Val Asn Arg Asn Phe Val Val Arg Tyr Glu Val Asn Trp
            260                 265                 270
Lys Thr His Glu Ile Lys Val Lys Gly His Asn
        275                 280

<210> SEQ ID NO 48
<211> LENGTH: 324
<212> TYPE: PRT
<213> ORGANISM: Staphylococcus aureus

<400> SEQUENCE: 48

Asn Ser Ala His Lys Asp Ser Gln Asp Gln Asn Lys Lys Glu His Val
1               5                   10                  15
Asp Lys Ser Gln Gln Lys Asp Lys Arg Asn Val Thr Asn Lys Asp Lys
            20                  25                  30
Asn Ser Thr Ala Pro Asp Asp Ile Gly Lys Asn Gly Lys Ile Thr Lys
        35                  40                  45
Arg Thr Glu Thr Val Tyr Asp Glu Lys Thr Asn Ile Leu Gln Asn Leu
    50                  55                  60
Gln Phe Asp Phe Ile Asp Asp Pro Thr Tyr Asp Lys Asn Val Leu Leu
65                  70                  75                  80
Val Lys Lys Gln Gly Ser Ile His Ser Asn Leu Lys Phe Glu Ser His
                85                  90                  95
Lys Glu Glu Lys Asn Ser Asn Trp Leu Lys Tyr Pro Ser Glu Tyr His
            100                 105                 110
```

Val Asp Phe Gln Val Lys Arg Asn Arg Lys Thr Glu Ile Leu Asp Gln
115                 120                 125

Leu Pro Lys Asn Lys Ile Ser Thr Ala Lys Val Asp Ser Thr Phe Ser
130                 135                 140

Tyr Ser Ser Gly Gly Lys Phe Asp Ser Thr Lys Gly Ile Gly Arg Thr
145                 150                 155                 160

Ser Ser Asn Ser Tyr Ser Lys Thr Ile Ser Tyr Asn Gln Gln Asn Tyr
                165                 170                 175

Asp Thr Ile Ala Ser Gly Lys Asn Asn Asn Trp His Val His Trp Ser
            180                 185                 190

Val Ile Ala Asn Asp Leu Lys Tyr Gly Gly Glu Val Lys Asn Arg Asn
        195                 200                 205

Asp Glu Leu Leu Phe Tyr Arg Asn Thr Arg Ile Ala Thr Val Glu Asn
210                 215                 220

Pro Glu Leu Ser Phe Ala Ser Lys Tyr Arg Tyr Pro Ala Leu Val Arg
225                 230                 235                 240

Ser Gly Glu Asn Pro Glu Phe Leu Thr Tyr Leu Ser Asn Glu Lys Ser
                245                 250                 255

Asn Glu Lys Thr Gln Phe Glu Val Thr Tyr Thr Arg Asn Gln Asp Ile
            260                 265                 270

Leu Lys Asn Arg Pro Gly Ile His Tyr Ala Pro Pro Ile Leu Glu Lys
        275                 280                 285

Asn Lys Asp Gly Gln Arg Leu Ile Val Thr Tyr Glu Val Asp Trp Lys
    290                 295                 300

Asn Lys Thr Val Lys Val Val Asp Lys Tyr Ser Asp Asp Asn Lys Pro
305                 310                 315                 320

Tyr Lys Glu Gly

<210> SEQ ID NO 49
<211> LENGTH: 284
<212> TYPE: PRT
<213> ORGANISM: Staphylococcus aureus

<400> SEQUENCE: 49

Asp Asn Asn Ile Glu Asn Ile Gly Asp Gly Ala Glu Val Val Lys Arg
1               5                   10                  15

Thr Glu Asp Thr Ser Ser Asp Lys Val Gly Val Thr Gln Asn Ile Gln
            20                  25                  30

Phe Asp Phe Val Lys Asp Lys Lys Tyr Asn Lys Asp Ala Leu Ile Leu
        35                  40                  45

Lys Met Gln Gly Phe Ile Asn Ser Lys Thr Thr Tyr Tyr Asn Tyr Lys
    50                  55                  60

Asn Thr Asp His Ile Lys Ala Met Arg Trp Pro Phe Gln Tyr Asn Ile
65                  70                  75                  80

Gly Leu Lys Thr Asn Asp Pro Asn Val Asp Leu Ile Asn Tyr Leu Pro
                85                  90                  95

Lys Asn Lys Ile Asp Ser Val Asn Val Ser Gln Thr Leu Gly Tyr Asn
            100                 105                 110

Ile Gly Gly Asn Phe Asn Ser Gly Pro Ser Thr Gly Gly Asn Gly Ser
        115                 120                 125

Phe Asn Tyr Ser Lys Thr Ile Ser Tyr Asn Gln Gln Asn Tyr Ile Ser
    130                 135                 140

Glu Val Glu Arg Gln Asn Ser Lys Ser Val Gln Trp Gly Ile Lys Ala
145                 150                 155                 160

-continued

```
Asn Ser Phe Ile Thr Ser Leu Gly Lys Met Ser Gly His Asp Pro Asn
                165                 170                 175

Leu Phe Val Gly Tyr Lys Pro Tyr Ser Gln Asn Pro Arg Asp Tyr Phe
            180                 185                 190

Val Pro Asp Asn Glu Leu Pro Pro Leu Val His Ser Gly Phe Asn Pro
        195                 200                 205

Ser Phe Ile Ala Thr Val Ser His Glu Lys Gly Ser Gly Asp Thr Ser
    210                 215                 220

Glu Phe Glu Ile Thr Tyr Gly Arg Asn Met Asp Val Thr His Ala Thr
225                 230                 235                 240

Arg Arg Thr Thr His Tyr Gly Asn Ser Tyr Leu Glu Gly Ser Arg Ile
                245                 250                 255

His Asn Ala Phe Val Asn Arg Asn Tyr Thr Val Lys Tyr Glu Val Asn
            260                 265                 270

Trp Lys Thr His Glu Ile Lys Val Lys Gly His Asn
        275                 280
```